United States Patent
Mutch et al.

[11] Patent Number: 6,027,498
[45] Date of Patent: Feb. 22, 2000

[54] CONTROL OF LIFE SUPPORT SYSTEMS

[75] Inventors: William Alan C. Mutch; Gerald Robin Lefevre, both of Winnipeg, Canada

[73] Assignee: University of Manitoba, Winnipeg, Canada

[21] Appl. No.: 08/714,116
[22] PCT Filed: Mar. 15, 1995
[86] PCT No.: PCT/CA95/00144
§ 371 Date: Jan. 6, 1997
§ 102(e) Date: Jan. 6, 1997
[87] PCT Pub. No.: WO95/24936
PCT Pub. Date: Sep. 21, 1995

[30] Foreign Application Priority Data
Mar. 15, 1994 [GB] United Kingdom .................. 9405002

[51] Int. Cl.[7] .................................................. A61B 17/36
[52] U.S. Cl. ............................................ 606/16; 128/898
[58] Field of Search .................................. 604/4, 7, 8, 9, 604/19, 27, 28, 30, 31, 66; 600/16, 17, 18; 128/898; 623/3

[56] References Cited

U.S. PATENT DOCUMENTS

| | | | |
|---|---|---|---|
| 4,001,700 | 1/1977 | Cook et al. | 128/204.21 X |
| 4,448,192 | 5/1984 | Stawitcke et al. | 128/204.26 |
| 4,584,996 | 4/1986 | Blum | 128/204.21 |
| 5,129,390 | 7/1992 | Chopin et al. | 128/204.21 |
| 5,316,009 | 5/1994 | Yamada | 128/716 |

FOREIGN PATENT DOCUMENTS

| | | |
|---|---|---|
| 2 624 744 | 6/1989 | France . |
| 2 025 662 | 1/1980 | United Kingdom . |
| WO 93/10844 | 6/1993 | WIPO . |

OTHER PUBLICATIONS

Suki et al. (Nature, vol. 368, Apr. 1994, pp 615–618).
Croughwell et al. (Ann. Thorac. Surg. 1994, 58:1702–1708).
Maeda, K. et al., Asaio Transactions, "Predictive Control by Physical Activity Rate of a Total Artificial Heart During Exercis", vol. 34, No. 3, Jul. 1988, 480–484.
Michael Heymann et al., "Blood Flow Measurements with Radionuclide–labeled Particles", Progress in Cardiovascular Diseases, vol. XX, No. 1 (Jul./Aug.), 1977, pp 55–79.

*Primary Examiner*—Linda C. M. Dvorak
*Assistant Examiner*—Rosiland Kearney
*Attorney, Agent, or Firm*—Sim & McBurney

[57] ABSTRACT

The flow of a biological fluid to an organ is computer controlled so that natural variation of such flow is simulated. Specifically described are control of a blood pump flow output during CPB to mimic normal pulsatile blood flow from the heart and control of a ventilator output To mimic normal breathing of healthy lungs. A pattern of variation over Time of instantaneous flow of a biological fluid to an organ of a mammalian species is established, a variable control parameter for regulation of flow of the biological fluid to the organ is generated in accordance with the pattern, and the flow of biological fluid is to the organ is controlled in accordance with the variable control parameter.

4 Claims, 39 Drawing Sheets

DAS16 'JUMPER BOX'

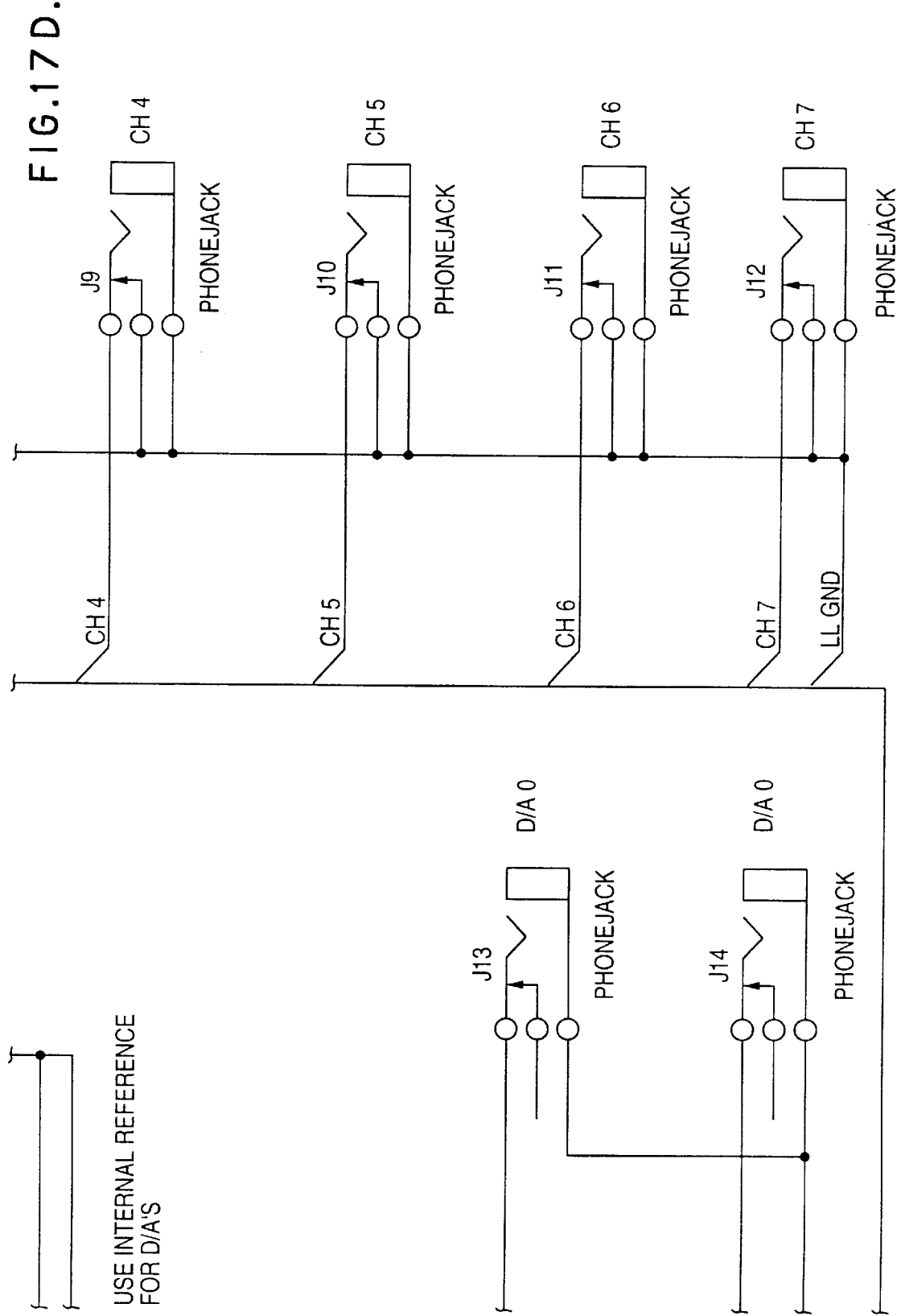

CONTROL OF LIFE SUPPORT SYSTEMS

FIELD OF INVENTION

The present invention relates to medical life support systems, and, in particular, to the control of cardiopulmonary bypass pumps for open heart surgery and mechanical ventilators to lungs.

BACKGROUND TO THE INVENTION

During cardiopulmonary bypass surgery (CPB), the most common operation conducted in North America, the heart is stopped and the blood which normally returns to the right side of the heart passes through a pump and oxygenating system and is returned to the aorta, thereby bypassing the heart and lungs. The flow of blood is essentially non-pulsatile with a low amplitude waveform having monotonous regularity.

Although a common procedure (in excess of 400,000 open heart procedures per annum are conducted in North America) and although tremendous strides have been made so that open heart surgery is safer for patients, the procedure is not without its dangers. Although the vast majority of patients have marked improvement in their cardiac functional status following their procedure, of concern is the potential for damage to other organ systems which can occur due to the need for CPB.

The following consequences have been identified with conventional non-pulsatile CPB, namely metabolic acidosis, interstitial fluid accumulation, elevated systemic vascular resistance, arteriovenous shunting and impaired brain oxygenation. Of greatest concern is the potential for neurologic damage. Increasingly, well conducted prospective trials have demonstrated an alarming rate of post-operative neuropsychologic disturbances following cardiac surgery. Recent studies have shown that up to 60 percent of patients undergoing open heart surgery have neuropsychologic deficits following their operation, so that as many as 240,000 patients per annum may develop neurologic abnormalities following cardiac surgery. These disturbances are subtle but involve higher cognitive functions of the brain.

Mechanical ventilation of the lungs represents one of the major accomplishments of modern medicine and is one of the cornerstones upon which modern surgery and intensive care is based. Despite many major advances, mechanical ventilation is still associated with a number of alterations in respiratory function which causes morbidity and mortality in patients requiring this type of support. Inability to maintain gas exchange remains one of the major limiting factors with regard to life-support of critically ill patients. Even in healthy patients being ventilated during elective surgery, alterations in gas exchange can be demonstrated. These relate to collapse of small airways and alveoli. Prevention of these alterations would likely represent a major advance in management of all patients requiring ventilatory support. Conventional mechanical ventilation is monotonously regular in delivery of set tidal volume and respiratory rate.

The monotonous regularity of pumping of blood during CPB and of set tidal volume and respiratory rate of a mechanical ventilator is in contrast to the intrinsic spontaneously variable rhythms of heart rate, blood pressure and respiration, associated with a normal functioning heart as well as the considerable range of tidal volume and respiratory rate which a healthy individual demonstrates during breathing.

The article "Predictive Control by Physical Activity Rate of a Total Artificial Heart During Exercise" Maeda et al, ASAIO Transactions, vol. 34, No. 3, pages 480–484, describes a control system for a total artificial heart which will increase cardiac output in response to increased metabolic demands associated with exercise. An accelerometer which senses movement produces signals which increase in proportion to increased activity associated with treadmill exercise. Measured changes in cardiac output in an exercised animal with its own heart are correlated with changes in the output of the accelerometer. Similar changes in accelerometer readings are then used to control the output of an implanted total artificial heart in an animal which is exercised to the same degree. Although the cardiac output changes depending on the intensity of the activity, there is no attempt to vary the beat to beat heart rate or beat to beat blood pressures at any given level of exercise.

SUMMARY OF THE INVENTION

In the present invention, the operation of a blood pump and mechanical ventilator are controlled to provide a flow of blood on the one hand and medical gases on the other which is varied in a manner that closely mimics the natural variation action of the heart and lungs and thereby overcomes some of the defects noted above. The invention is not applicable only to these two devices but is applicable to regulation in control of flow of any biological fluid to any organ. Although the existence of such variability in biological fluid flow is known, no one has heretofore taken such variability into account during the application of life support systems.

Blood normally is pumped in a monotonously regular non-pulsatile fashion or low amplitude pulsatile manner.

In one aspect of the present invention, a predetermined pattern of variations over time of instantaneous changes in flow of a biological fluid to an independently-functioning normal organ of a mammalian species first is generated. The mammalian species may be the human to whom the procedure is to be applied, another human or another mammalian species which is a model for a human, such as, a dog or a pig. The generated pattern may be an actual pattern determined from the mammalian species or may be a computer simulation of the known variation in the flow. The generated pattern generally is provided with a sufficient number of determinations as to be representative of normal variation. Depending on the procedure involved, the pattern of variation may be established for the appropriate change in flow. For example, for control of blood pump during CPB, a pattern of variation over time of instantaneous blood pressure and heart rate of an independently-functioning healthy heart is established. For control of a ventilator device, a pattern of variation over time of instantaneous respiratory rate and tidal volume of independently-functional normal lungs is established.

A variable control parameter then is generated for regulation of flow of the biological fluid to an organ during controlled life support conditions in accordance with the pattern. This control parameter is most readily achieved by computer processing of the predetermined pattern of variation. In effecting such computer processing, the individual values of the parameters in the pattern and the peak-to-peak time interval between the individual values are recorded and analyzed. For example, for control of a CPB pump, each of the individual blood pressures for the pattern of instantaneous blood pressure and heart rate and the time interval (heart rate) between each of the individual blood pressures are recorded. For control of a ventilator, each of the individual respiratory rates and tidal volumes for the pattern of instantaneous respiratory rate and tidal volumes and the time interval between each of the individual respiratory rates and tidal volumes are recorded.

The variable control parameter generated in the procedure of the invention depends on the flow of biological fluid being regulated. In the case of the CPB pump, a signal is generated corresponding in value to an individually-determined blood pressure for a period of time corresponding to the heart rate for the difference between the one individually-determined blood pressure and the next individually-determined blood pressure of the pattern. In the case of the ventilator, a signal is generated corresponding in value to an individually-determined respiratory rate and tidal volume.

In the present invention, the next step is to control the flow of biological fluid to the organ during controlled life support conditions in accordance with the variable control parameter. In this way, the flow of biological fluid to the organ is effected in accordance with the pre-established pattern of variation over time and hence mimics the natural flow of the biological fluid to the organ.

The manner of control of the flow of biological fluid to the organ depends on the biological fluid and the organ concerned. For example, in the case of the control of a CPB pump, a control voltage is generated corresponding in magnitude to the generated signal from the variation pattern and the control voltage is applied to the pump to provide an output of blood from the pump to the body during cardiopulmonary bypass of a pressure proportional to the magnitude of the signal for the period of time (peak-to-peak time interval). The steps of generating a signal, generating a control voltage and applying the control voltage to the pump then is repeated for each next individually-determined blood pressure of the pattern. Depending on the duration of the operation and the number of individual determinations in the pattern, it may be necessary to repeat these steps again for the pattern, reading either from the beginning or in the reverse direction. In this way, a pulsatile flow of blood from the pump is provided to the CPB patient which mimics normal pulsatile blood flow from a healthy heart.

Similarly, for the control of ventilating gas from a ventilator, a control voltage is generated corresponding in magnitude to the generated signal from the variable pattern and the control voltage is applied to the ventilator device to provide an output of ventilating gas from the ventilator device of a respiratory rate proportional to the magnitude of the signal. The steps of generating a signal, generating a control voltage and applying the control voltage to the ventilation device are repeated for each next individually-determined respiratory rate of the pattern. In this way, a variable flow of ventilating gas from the ventilator device to the lungs of the body during controlled life support conditions is provided which mimics normal breathing of healthy lungs.

As noted above, the present invention is applicable not only to control of a CPB pump or a mechanical ventilator but also to any other operation or device involving this control of a biological fluid to any organ. For example, the principles of the invention may be used in intra aortic balloon counterpulsation (IABC), the technique used to support patients, usually following CPB, when they are unable to maintain adequate cardiac output, until enough heart function has returned to permit its discontinuation.

The principles of the invention may be employed to improve hemodialysis by introducing variability to the pumping to provide improved diffusion across the dialysis membrane by promoting better mixing of blood and avoidance of areas of relatively stagnant flow and thereby decreasing dialysis time.

In addition, the present invention may be employed with extracorporeal membrane oxygenation (ECMO), which is a modification of CPB in which bypass is instituted to support the patient while giving the lungs a chance to heal. The patient is ventilated while on ECMO and if the therapy is successful, eventually weaned off ECMO and the ventilator. Computer control of the CPB pump in this situation has the potential to enhance organ perfusion, while computer controlled ventilation has the potential to activate lung healing and of improving gas exchange in order to facilitate earlier weaning from ECHO.

The present invention further may be employed in conduction with right and left ventricular assist devices (RVAD and LVAD), which are occasionally used to support patients after CPB when they are unable to maintain adequate output without this type of support. Patients given such support are simultaneously being ventilated. Computer-controlled ventilation and computer-controlled RVAD and LVAD, as provided herein, may improve organ perfusion while computer-controlled ventilation may indirectly influence hemodynamic variability.

Another application of the principles of the present invention is in the perfusion of organs prior to transplantation.

In accordance with another aspect of the present invention, there is provided apparatus for controlling the flow of a biological fluid to an organ, which comprises: means for establishing a predetermined pattern of variations over time of instantaneous changes in flow of a biological fluid to an independently-functioning normal organ of a mammalian species; means for generating a variable control parameter for regulation of flow of the biological fluid to an organ during controlled life support conditions in accordance with the predetermined pattern and means for controlling the flow of the biological fluid to the organ during controlled life support conditions in accordance with the variable control parameter.

When the apparatus provided in accordance with this aspect of the present invention is used in controlling the flow of blood by a pump to a body during cardiopulmonary by-pass wherein said means for establishing a predetermined pattern comprises means for establishing a predetermined pattern of variation over time of instantaneous blood pressure and heart rate of an independently-functioning heart of a mammalian species; said means for generating a variable control parameter comprises means for generating a signal corresponding in value to an individually-determined blood pressure for a period of time corresponding to the heart rate for a difference between such individually-determined blood pressure and the next individually-determined blood pressure of said predetermined pattern and means for generating a control voltage corresponding in magnitude to said signal; and said means for controlling the flow of the biological fluid comprises means for applying said control voltage to said pump to provide an output of blood from said pump to the body during cardiopulmonary bypass of a pressure proportional to the magnitude of the signal for said period of time and means for repeating the steps of generating a signal, generating a control voltage and applying the control voltage to the pump for each next individually-determined blood pressure of said predetermined pattern.

When the apparatus provided in accordance with this aspect of the present invention is used in controlling the flow of ventilating gas from a ventilator device to the lungs of a body during controlled life support conditions wherein said means for establishing a predetermined pattern comprises means for establishing a predetermined pattern of variation over time of instantaneous respiratory rate and tidal volume of the independently-functioning healthy lungs of a mammalian species; said means for generating a variable control parameter comprises means for generating a signal corresponding in value to an individually-determined respiratory rate and tidal volume in said predetermined pattern and means for generating control voltage corresponding in magnitude to said signal; and said means for controlling the flow of biological fluid comprises means for applying the control voltage to the ventilator device to provide an output of ventilating gas from the ventilating device of a respiratory rate proportional to the said signal and means for repeating the steps of generating a signal, generating a control voltage and applying the control voltage to the ventilator device for each next individually-determined respiratory rate of the predetermined pattern.

Figure 12:
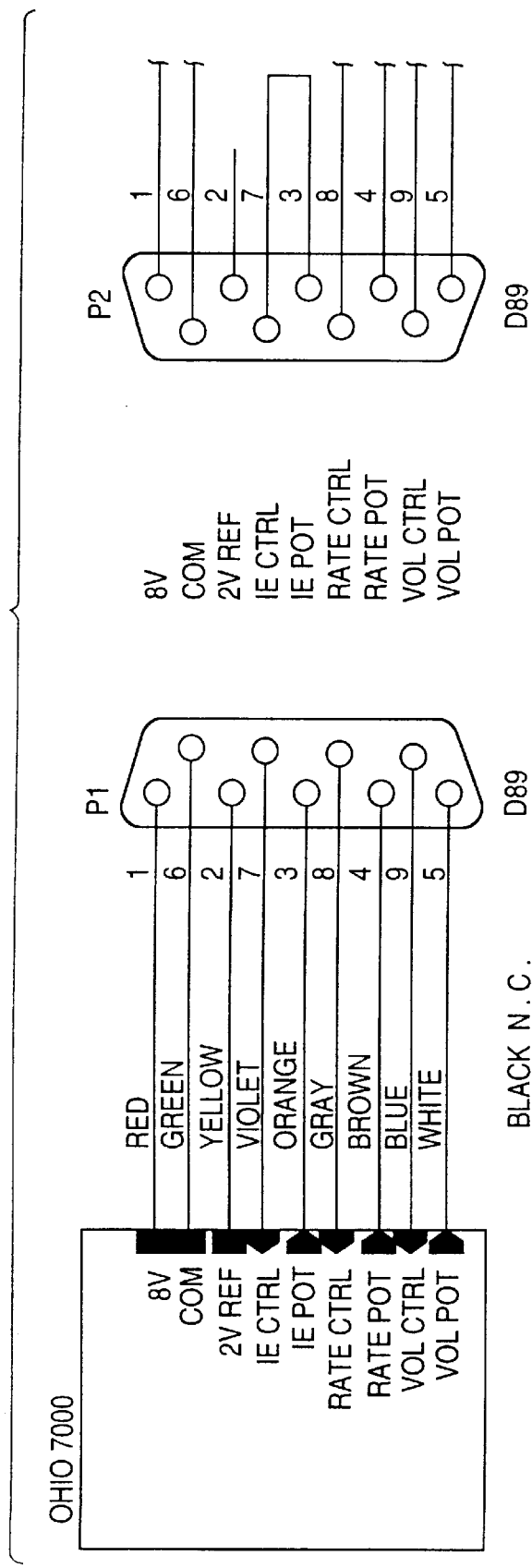
FIGS. 12A to E show the internal wiring harness of the Ohio Interface Unit. Connector 'P1' and module 'Ohio 7000' refer to the cable and modifications added to the Ohio 7000 Ventilator. This Figure shows all physical wiring connections of the electronic modules ('Volume Modulator' and 'Rate Modulator') to the switches and connectors. The Ohio 7000 supplies the power (8 V & COM). Connectors 'P2' and 'P3' are opposite gender. Experimental monitoring jacks ('J1' through 'J4') are for an external data acquisition system. Connector 'P3' interfaces to the Metrabyte model DASH16 A/D and digital to analog (D/A) converter. Switch S1 and S2 provide the ability to cancel 'RATE' or 'VOLUME' modulation individually ('manual' position) at any time.
Figure 12B:
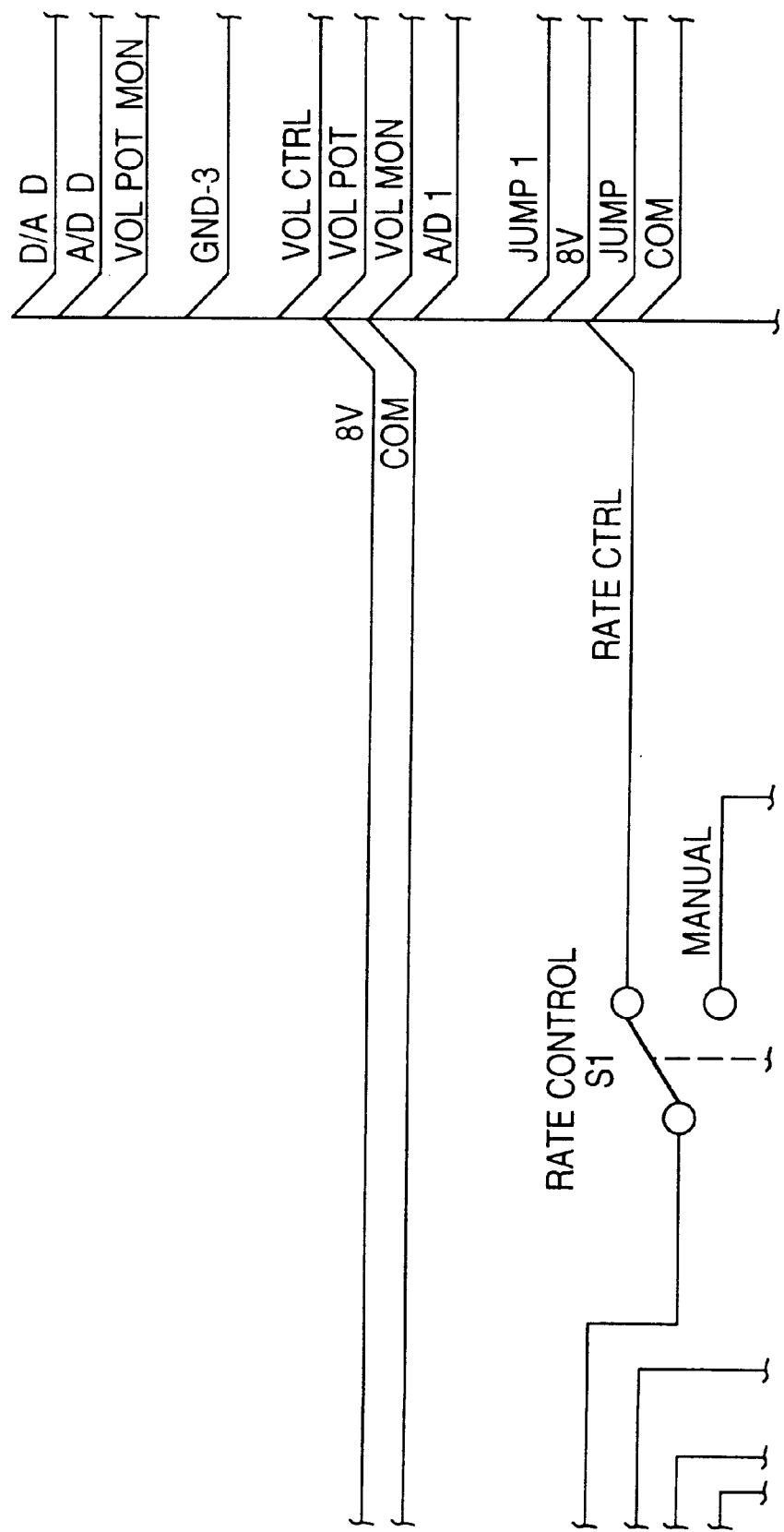
Figure 12C:
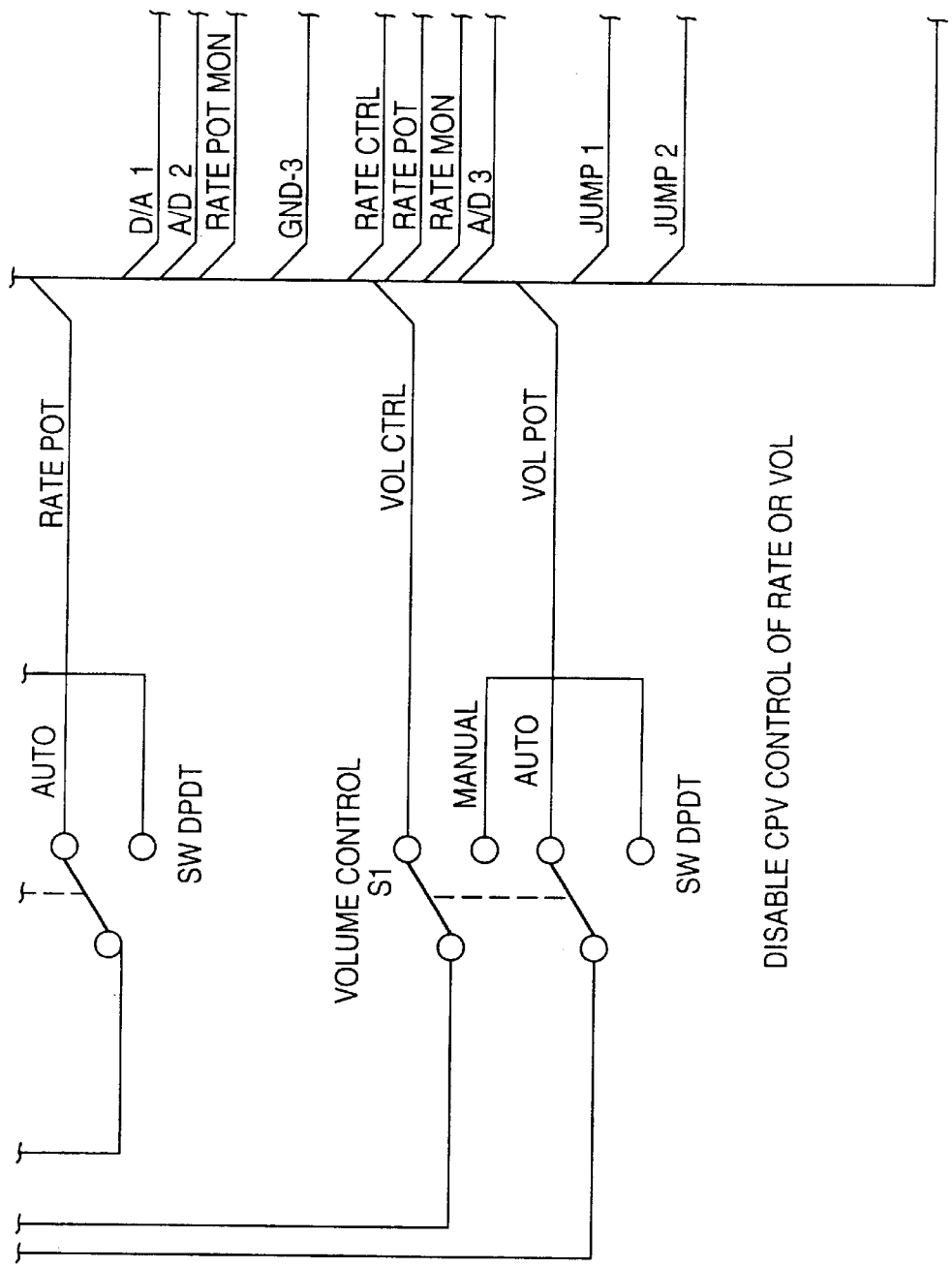
Figure 12D:
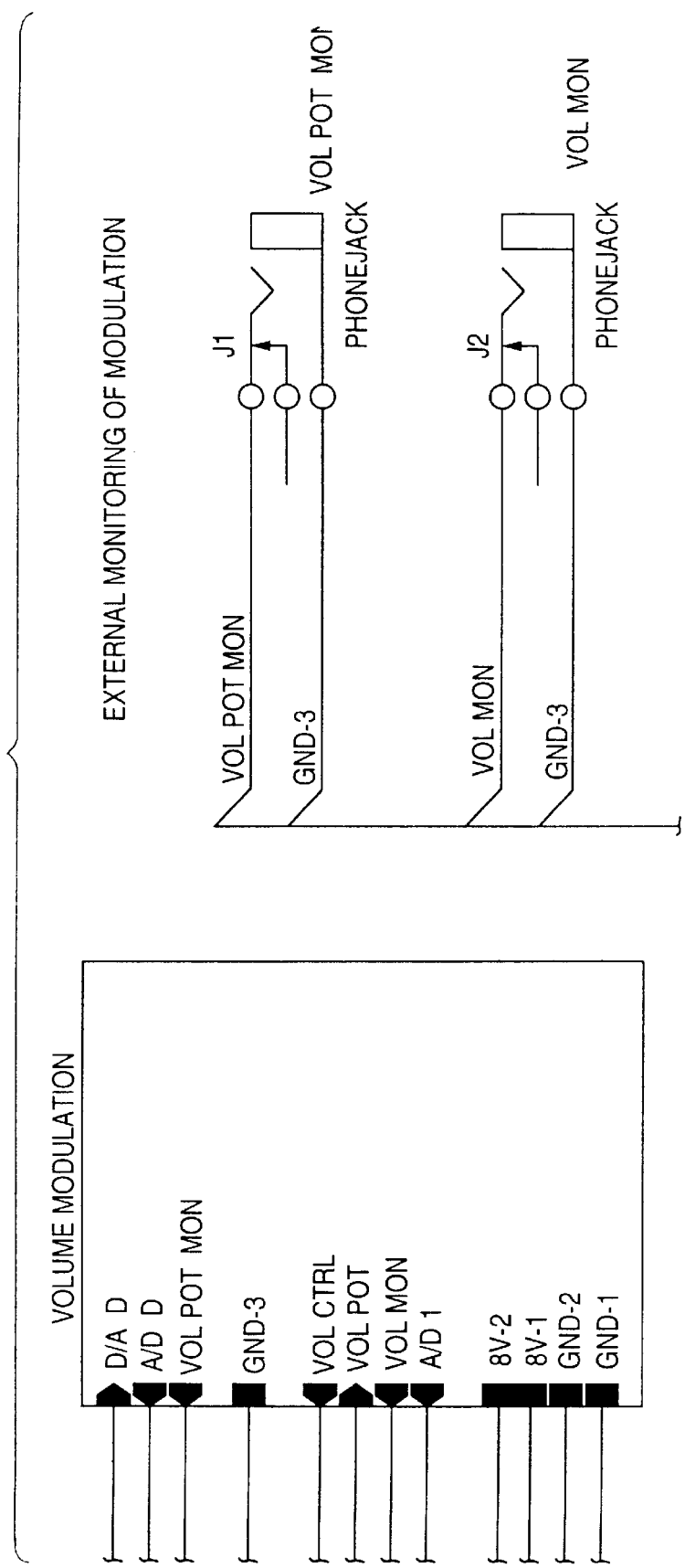
Figure 12E:
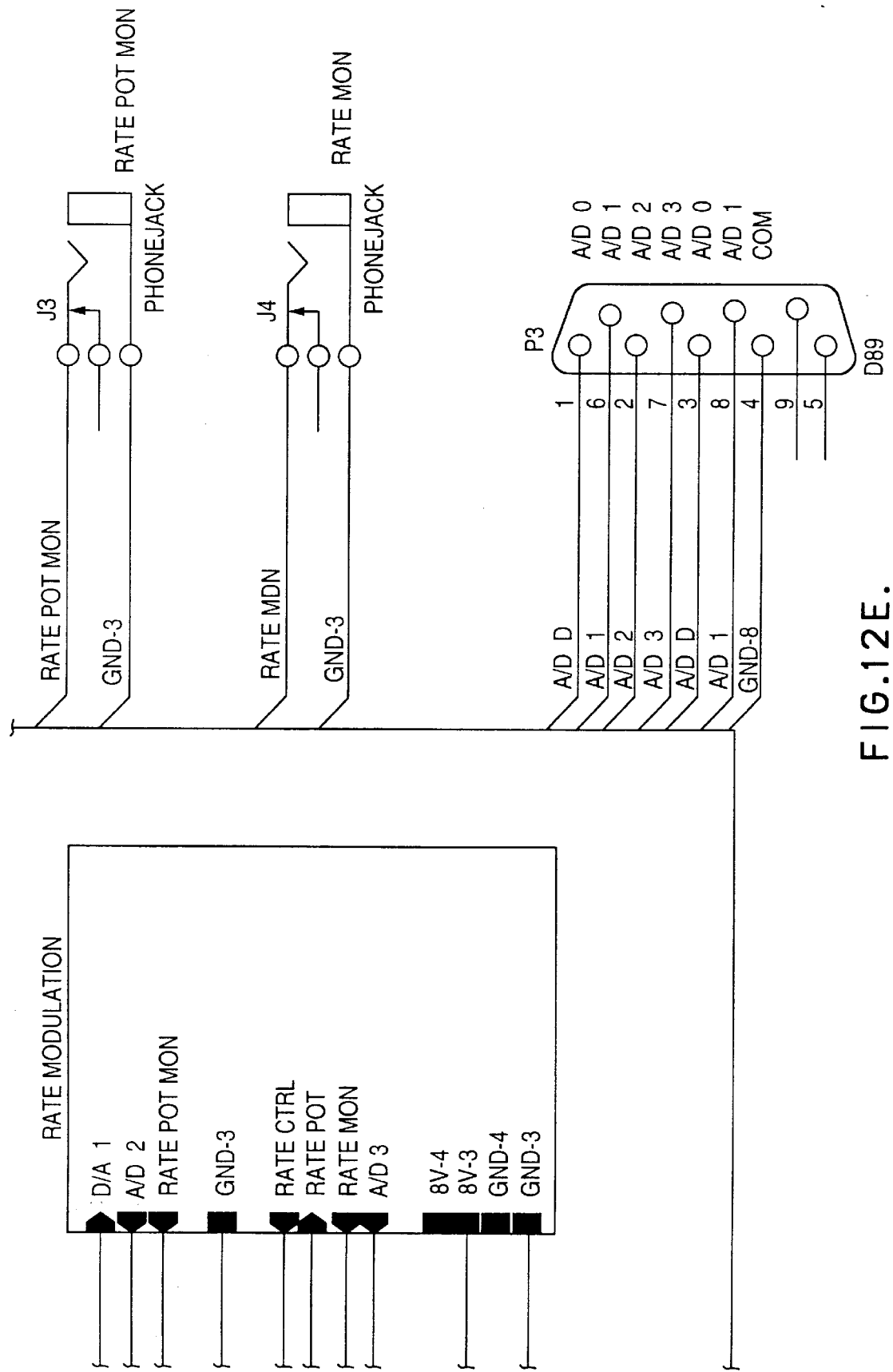
Figure 13A:
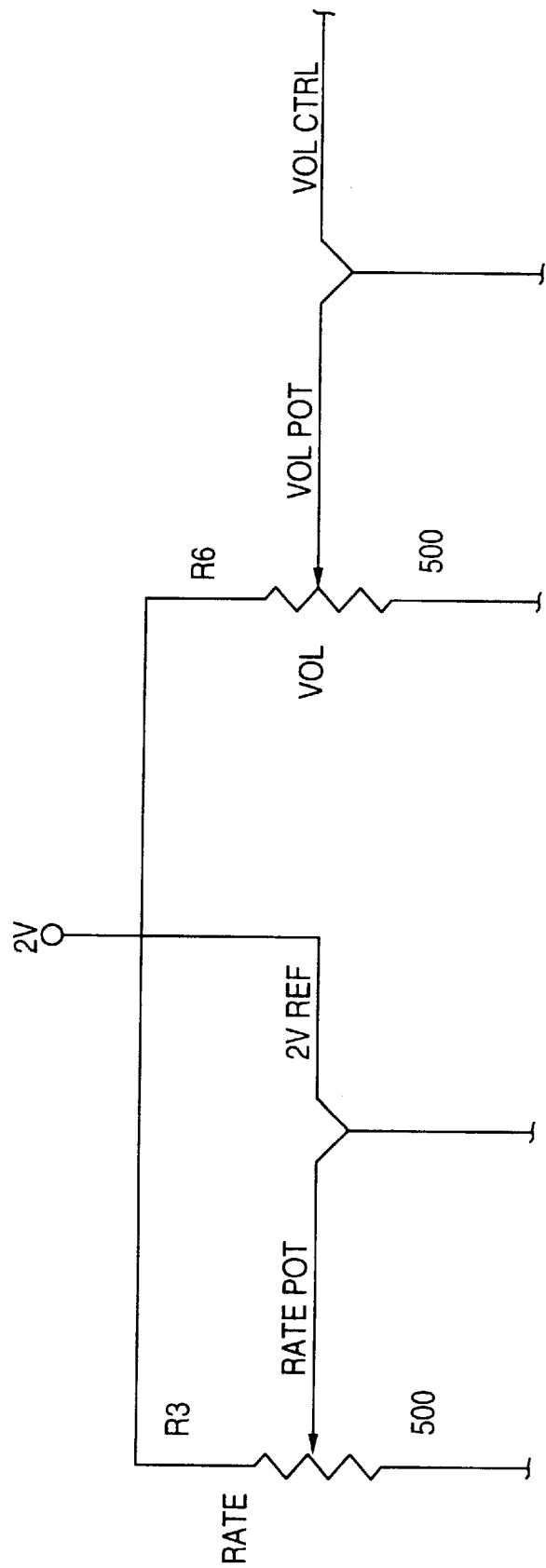
FIGS. 13A to F display an excerpt of the Ohio 7000 Ventilator control circuitry generated with an ohm meter and a photocopy of the service manual. Refer to the 'IE' ratio control R14. The control's wiper was originally connected to amplifier U22B. Modulation of the 'IE' control is introduced by inserting an external summing amplifier between the control and amplifier U22B (pins 3 and 7 of connector P4). Similarly, the 'RATE' and 'VOLUME' controls and their associated amplifiers (U22A and U5D) are routed to P4 pins 4 and 8, and 5 and 9 respectinvely. The 2 volt reference voltage for the 'RATE' and 'VOLUME' controls, as well as 8 volt supply and common are also routed to connector P4.
Figure 13B:
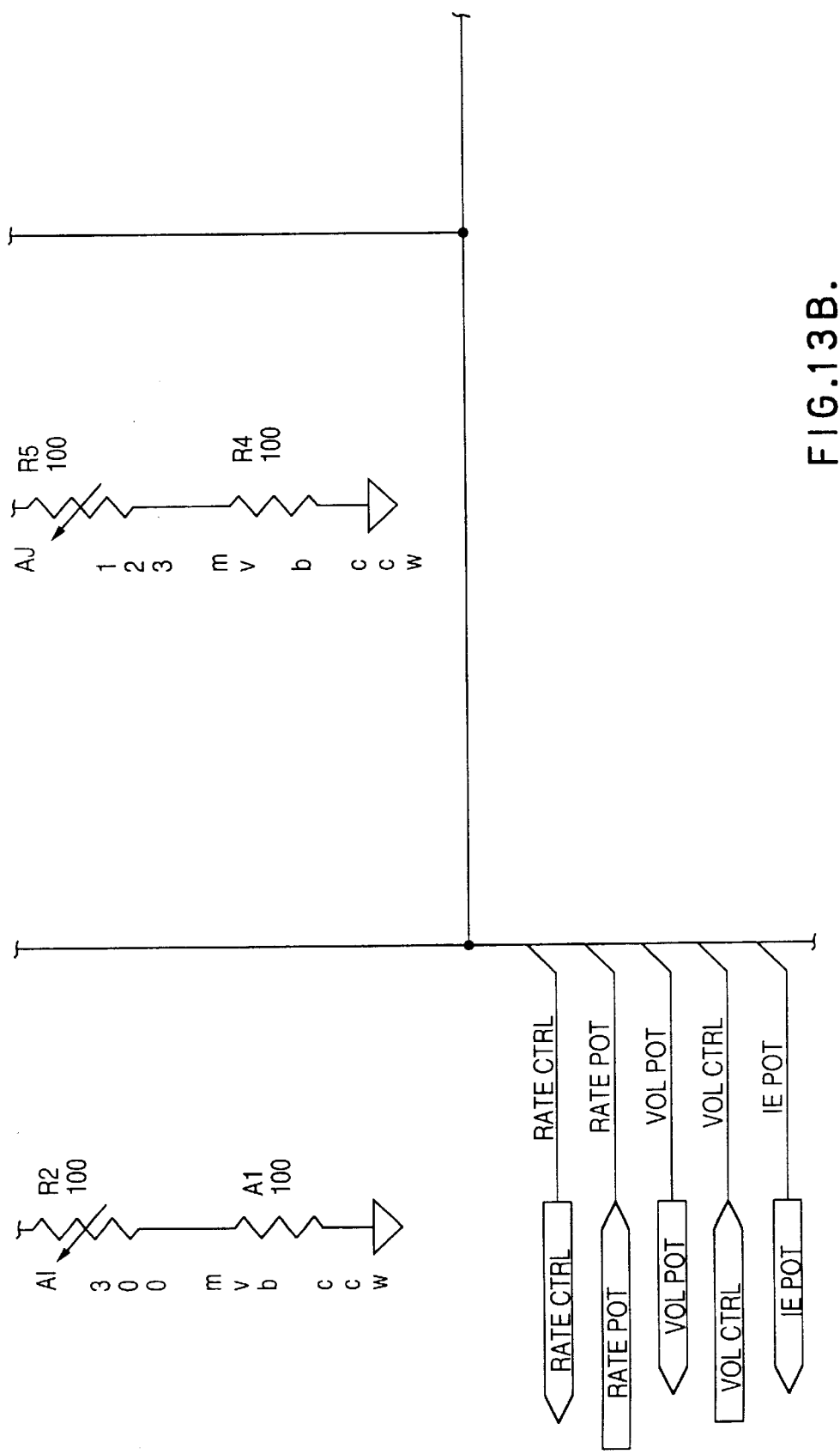
Figure 13C:
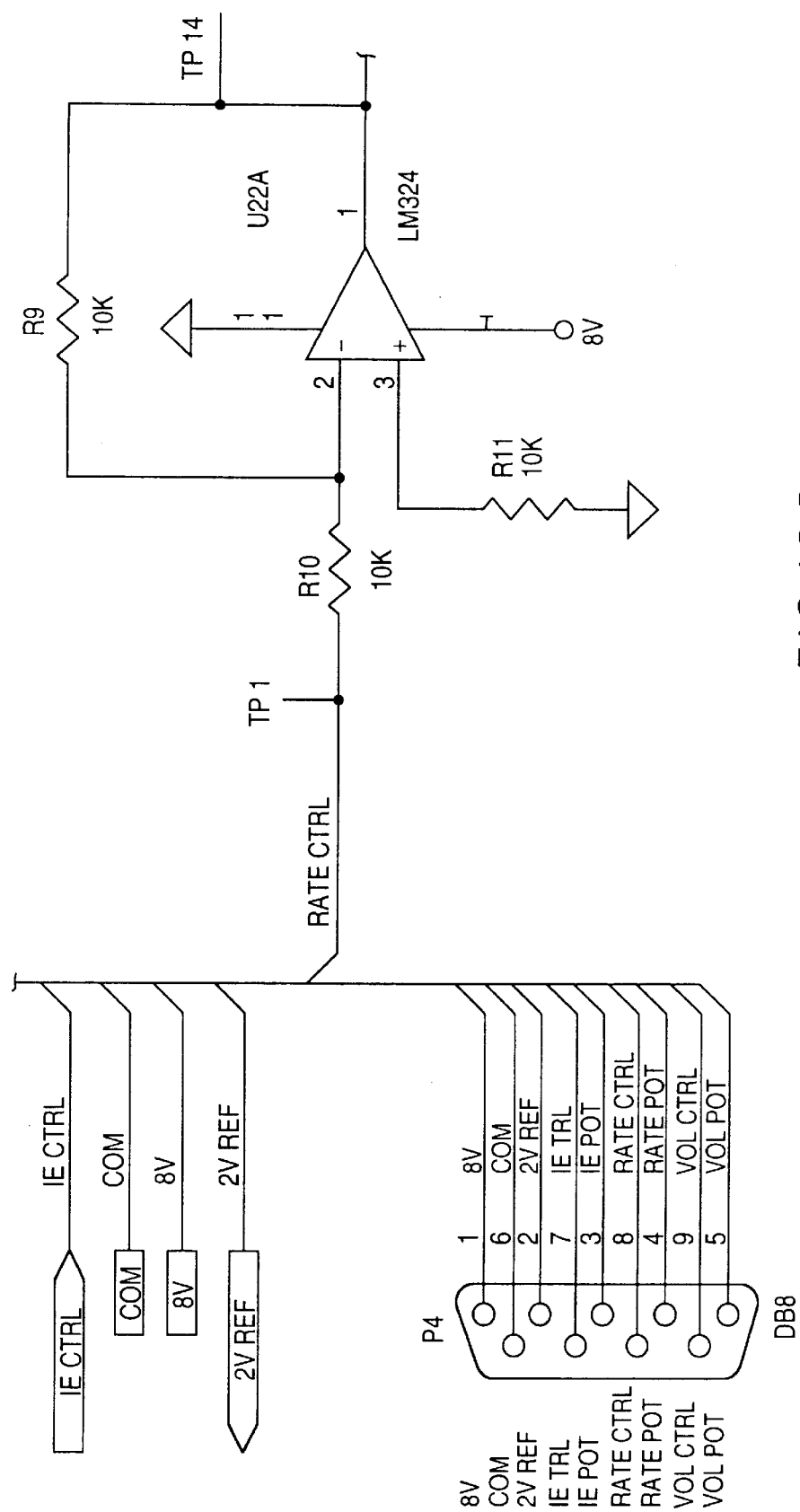
Figure 13D:
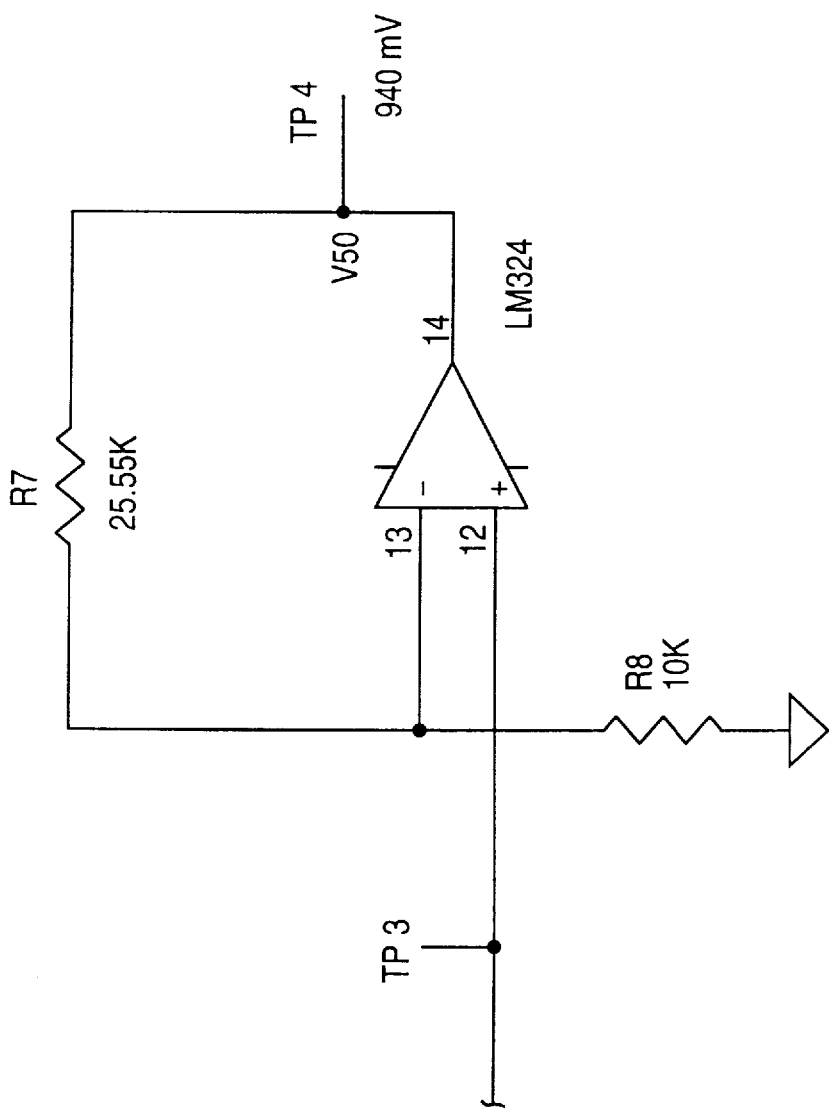
Figure 13E:
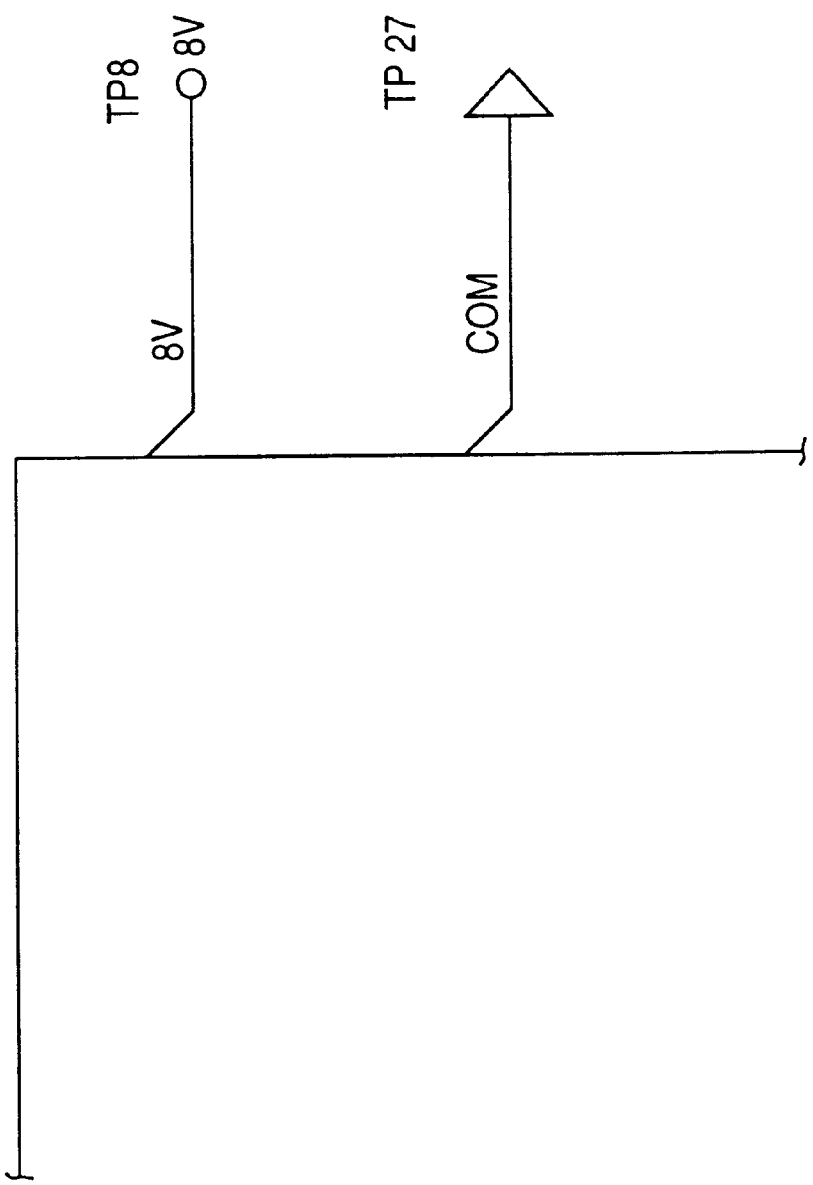
Figure 13F:
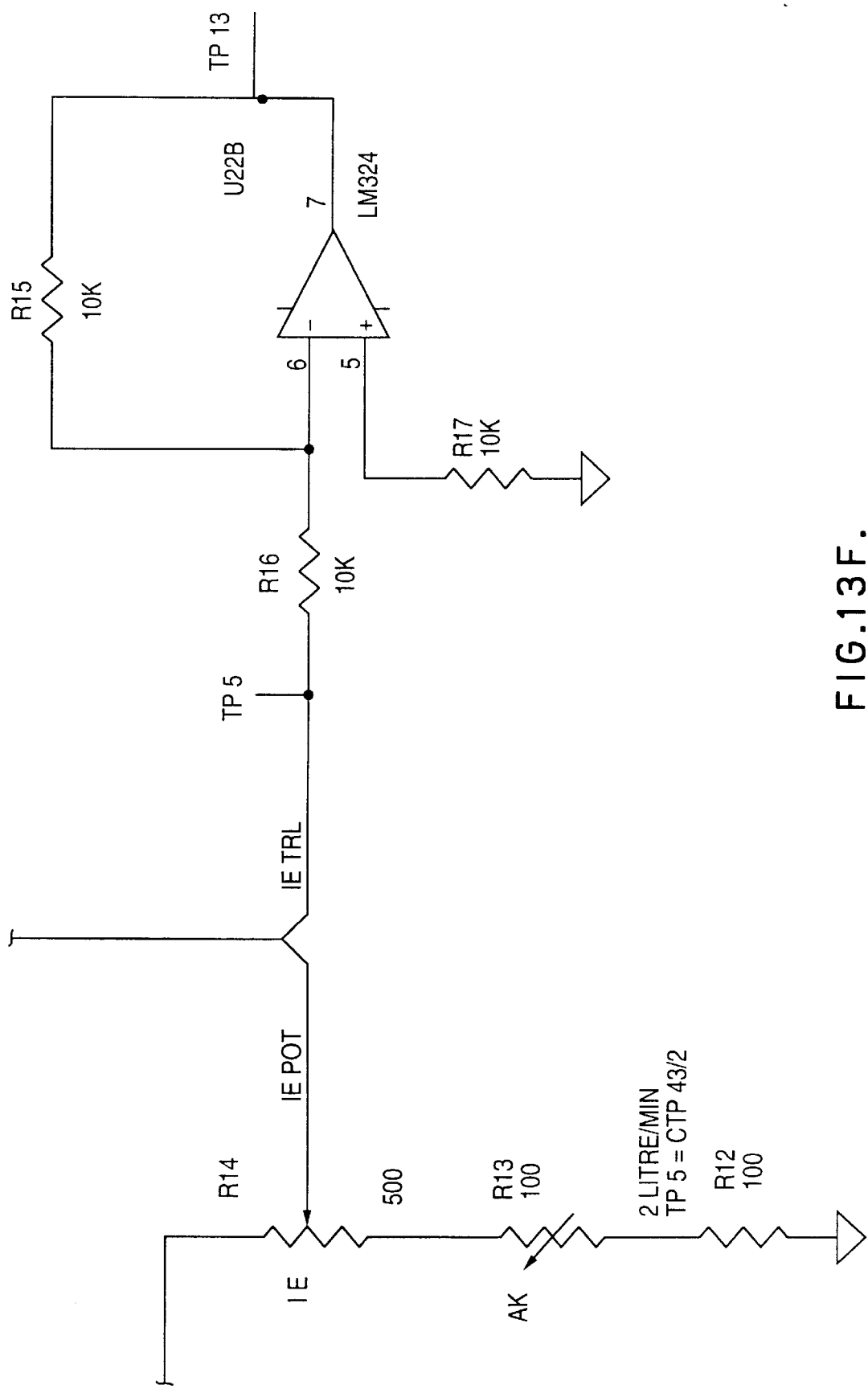
Figure 14A:
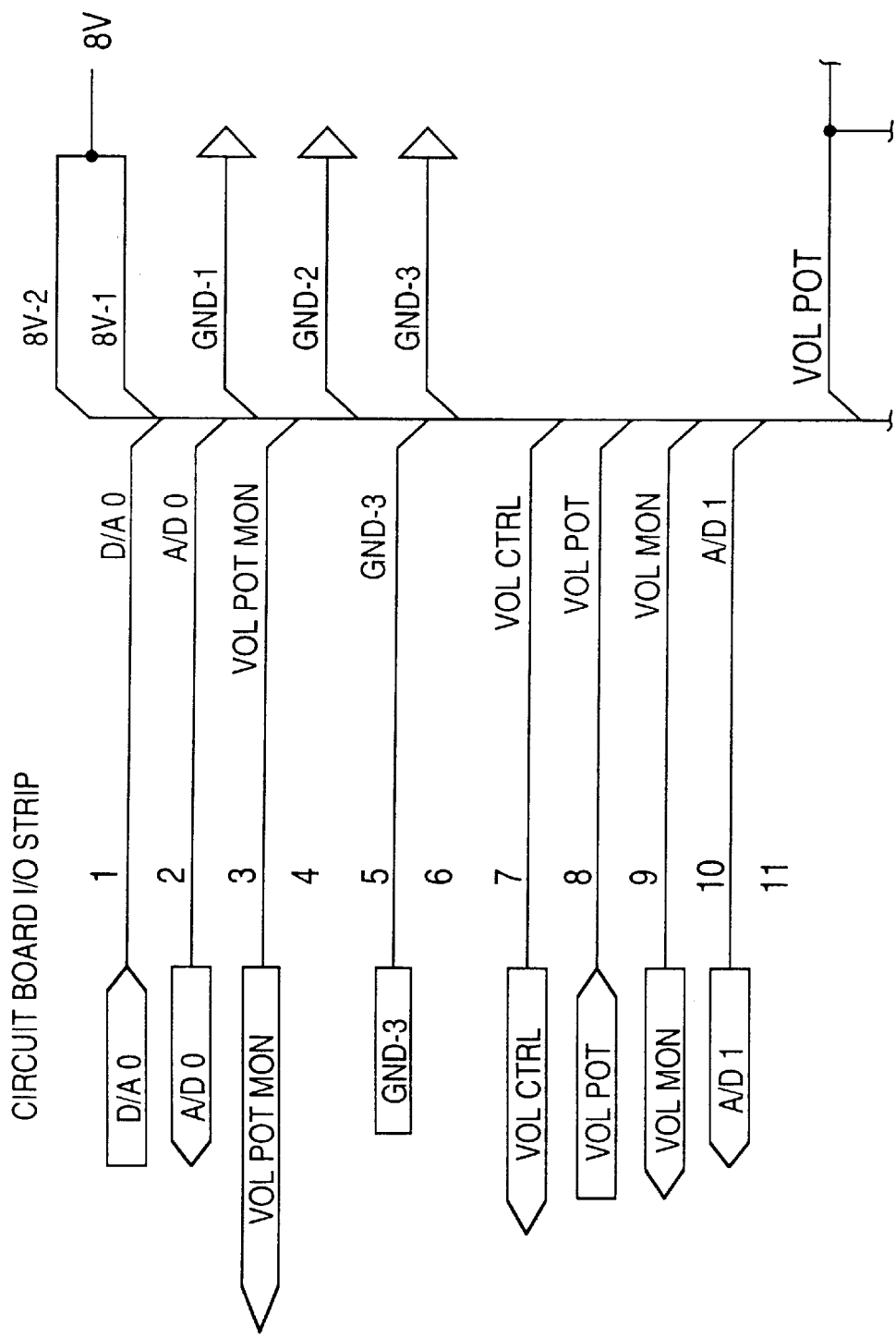
Figure 14B:
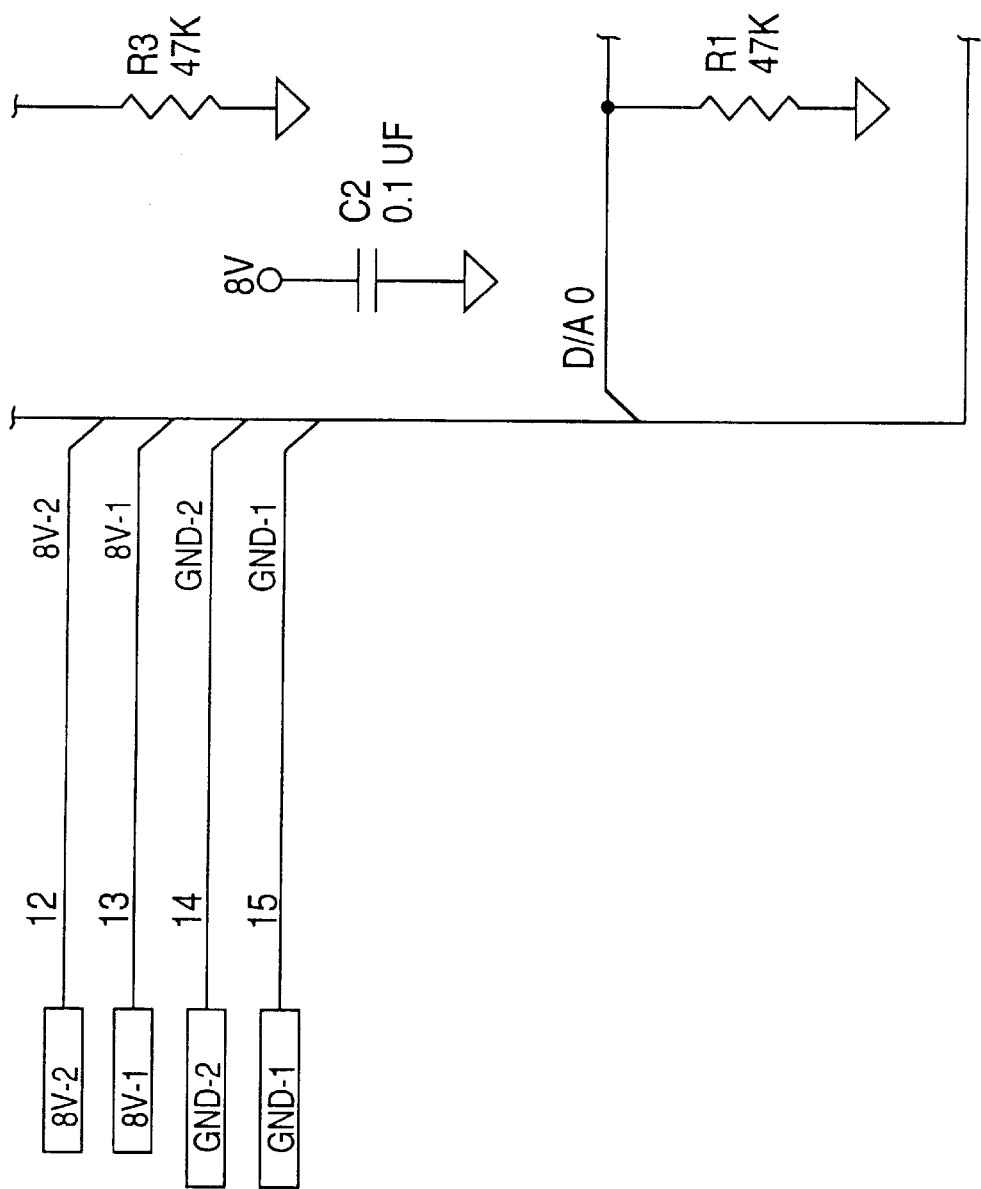
Figure 14C:
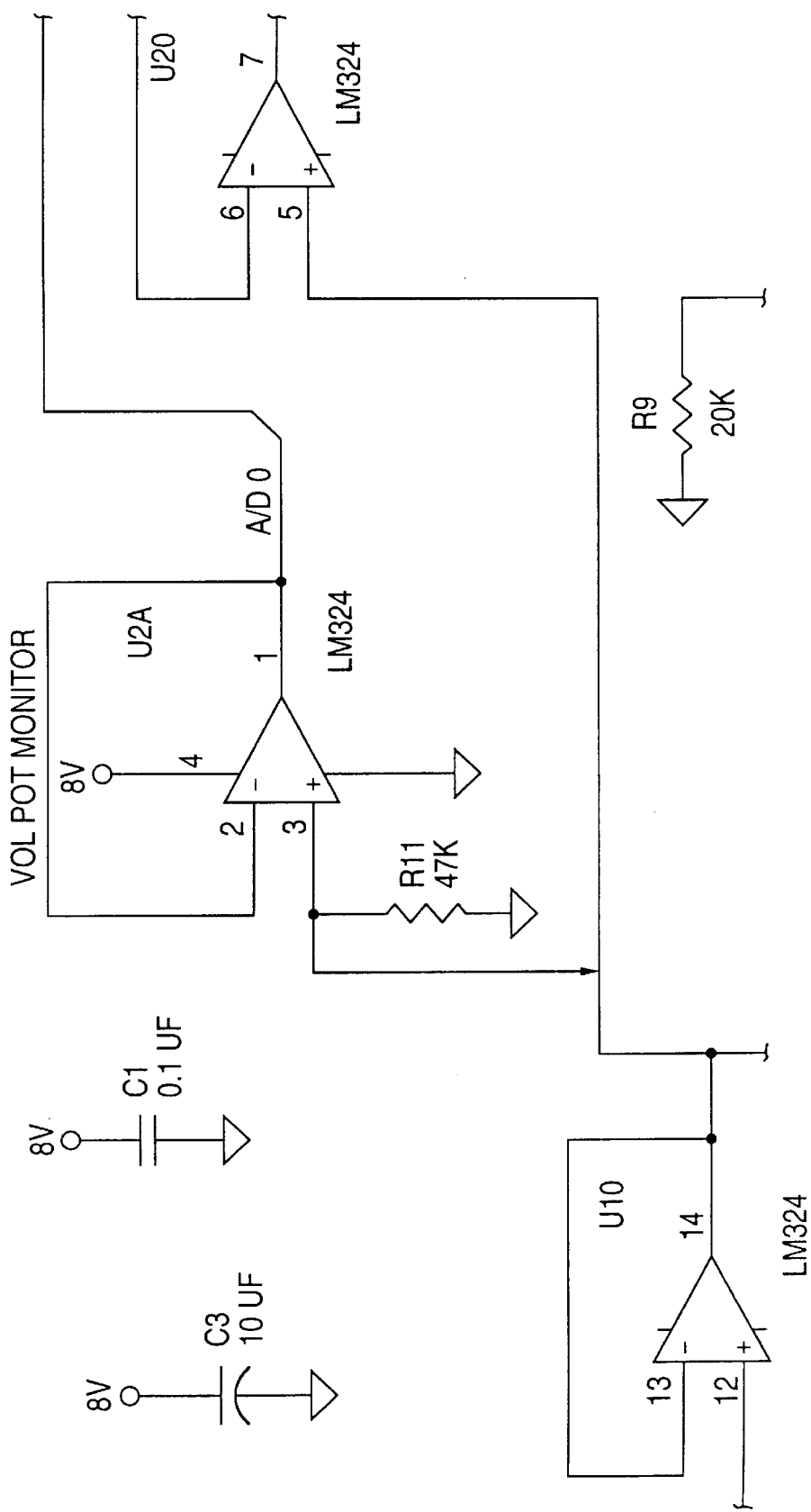
Figure 14D:
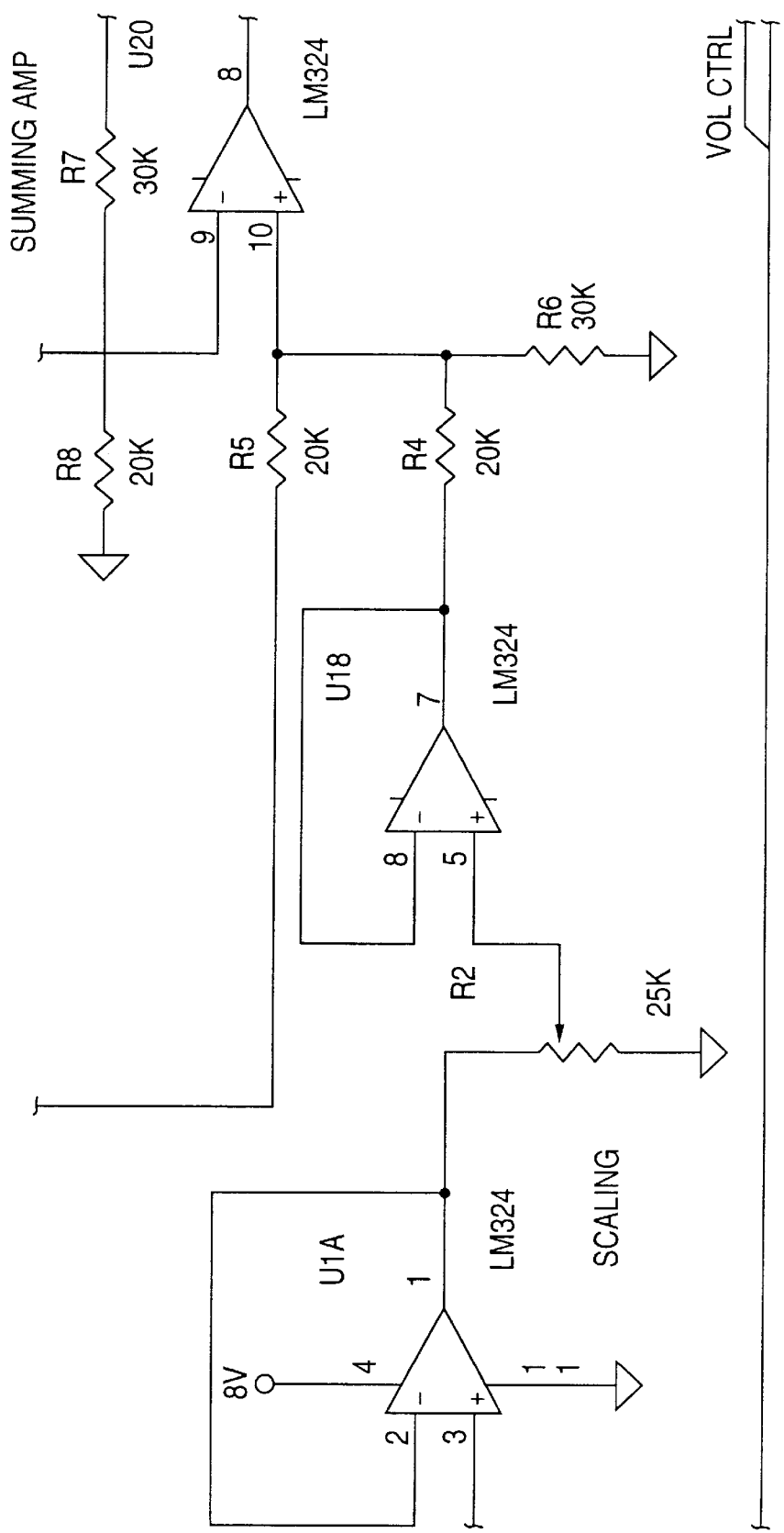
Figure 14E:
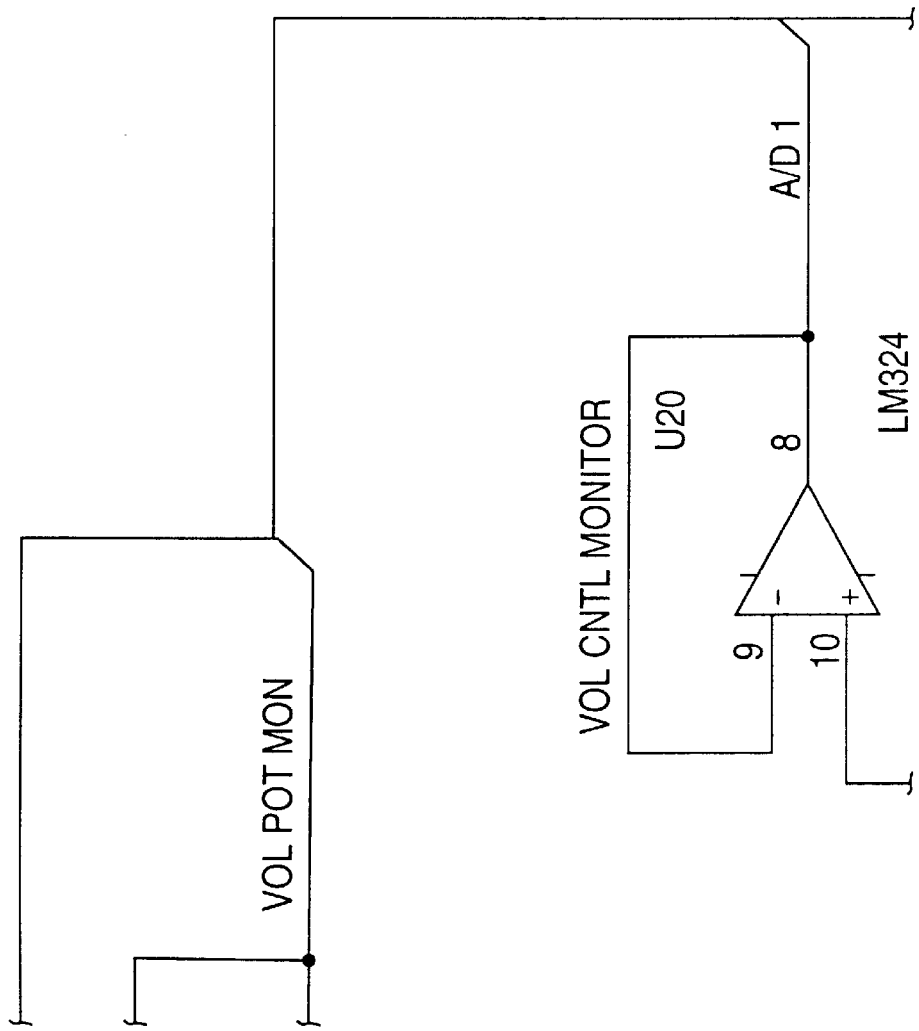
Figure 14F:
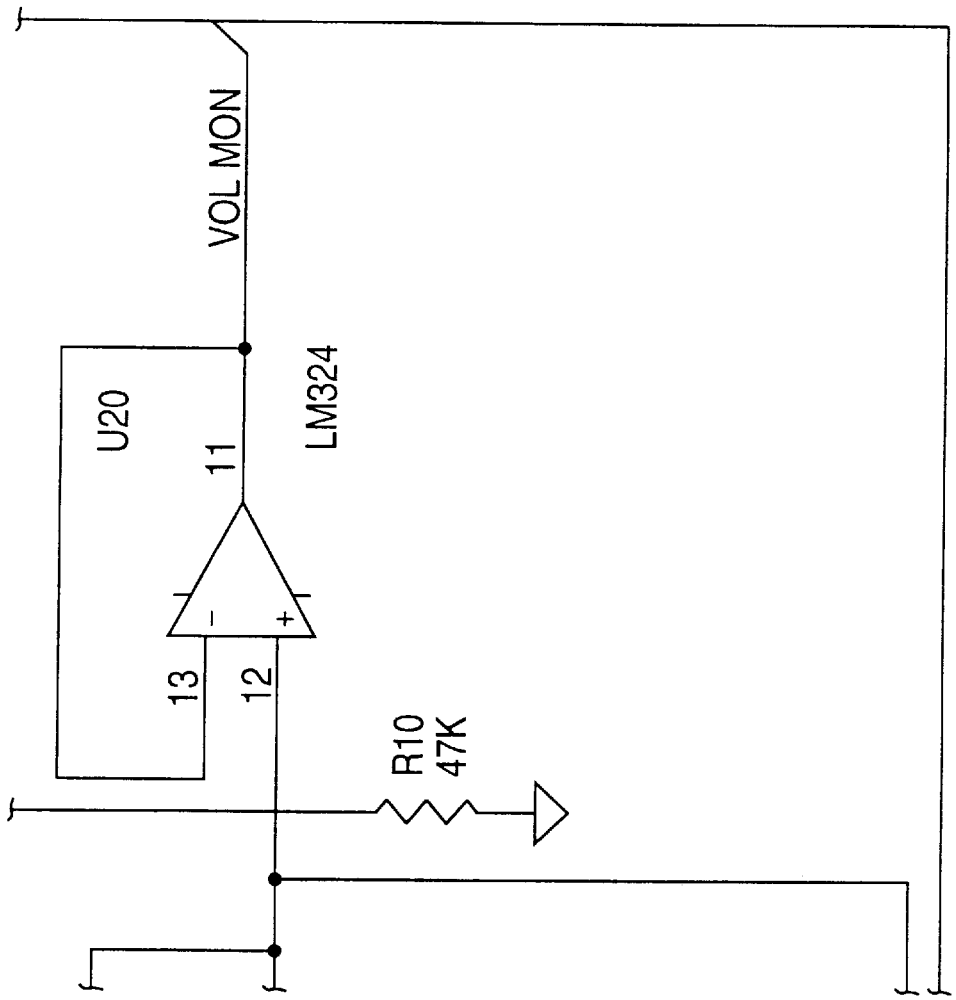
Figure 15A:
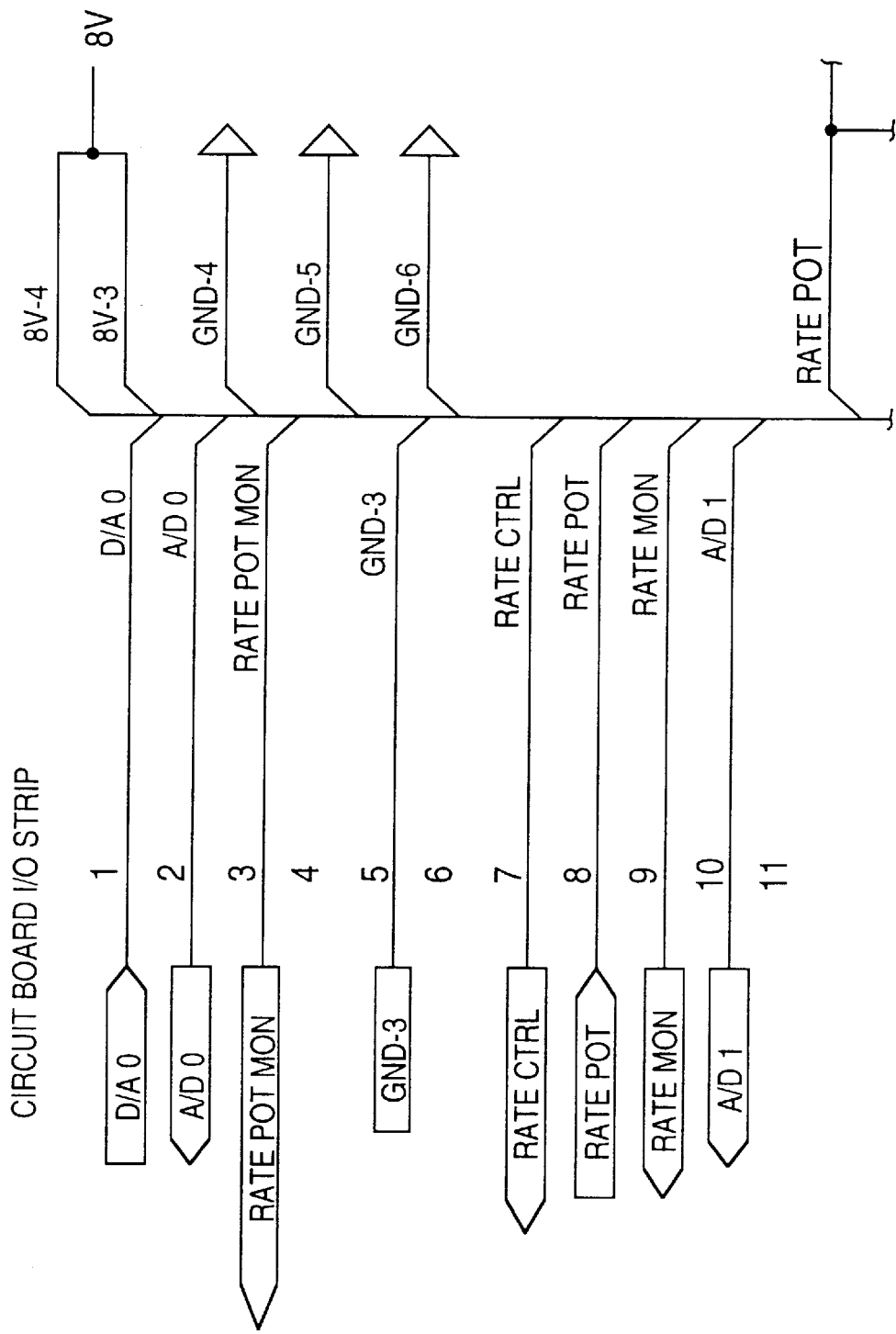
Figure 15B:
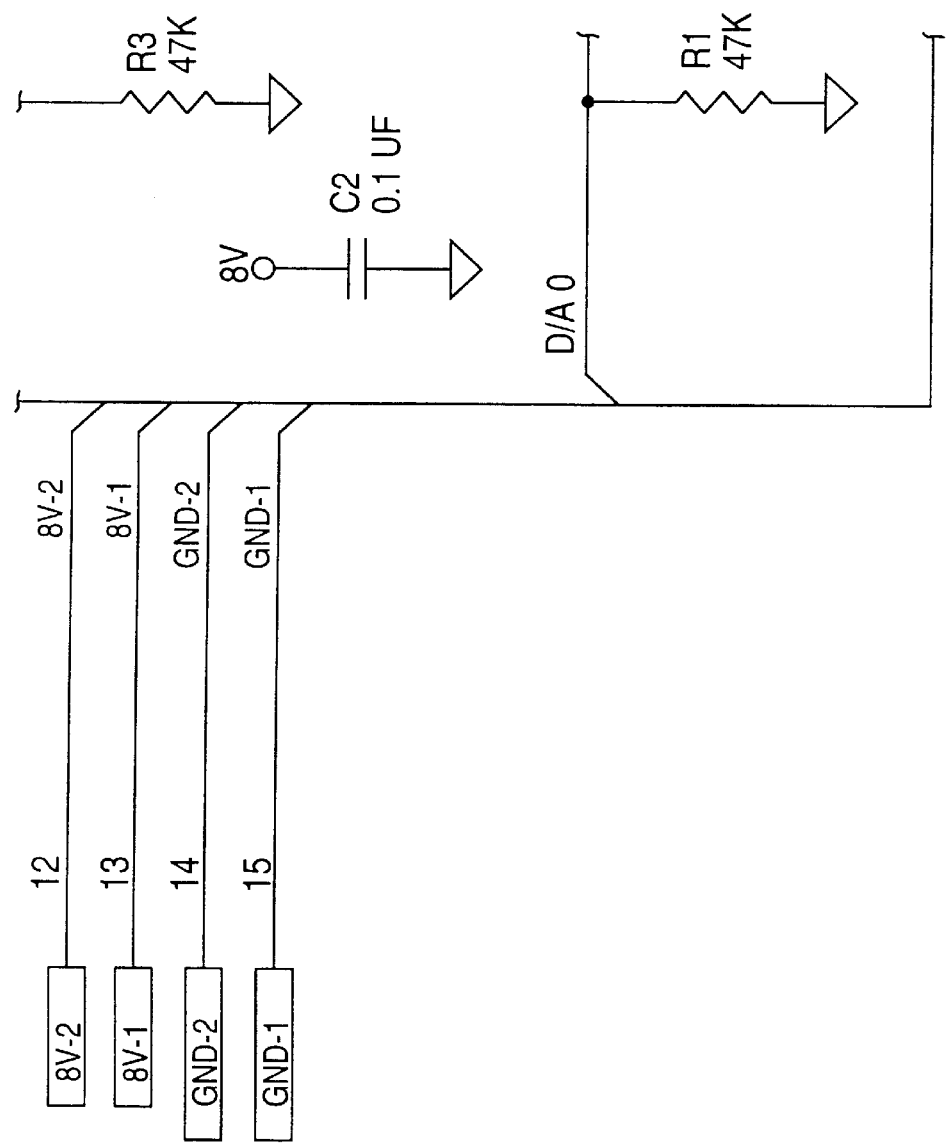
Figure 15C:
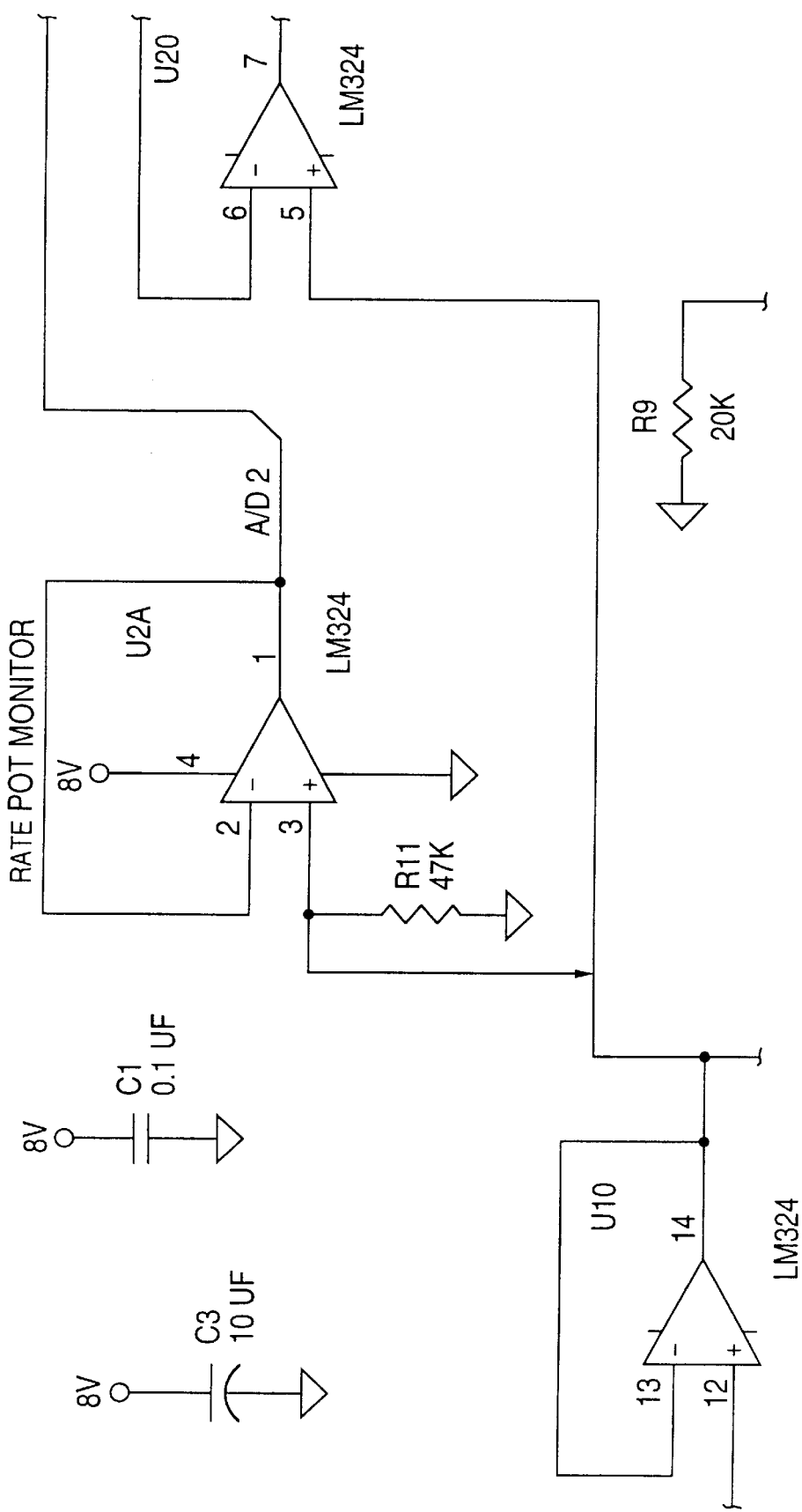
Figure 15D:
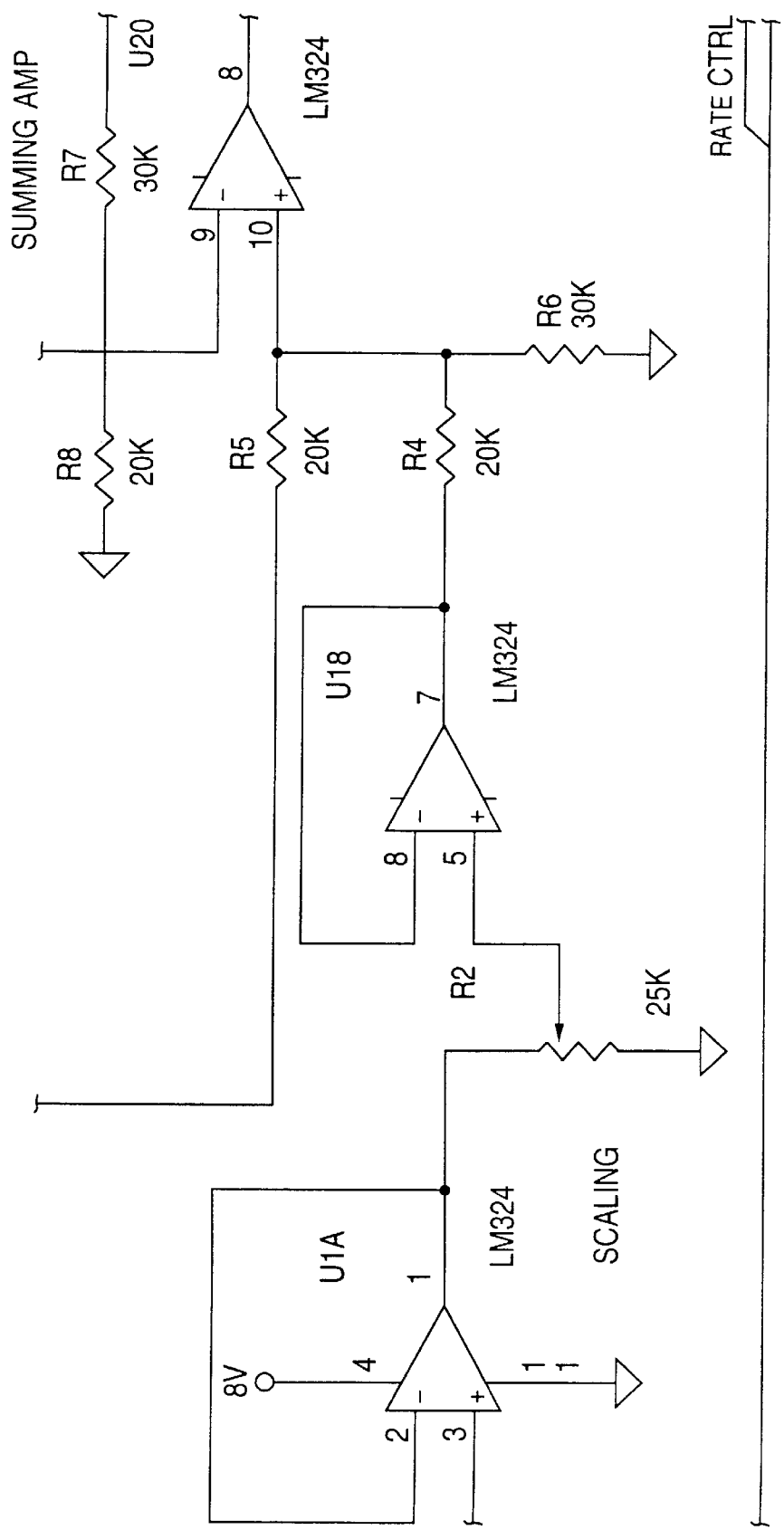
Figure 15E:
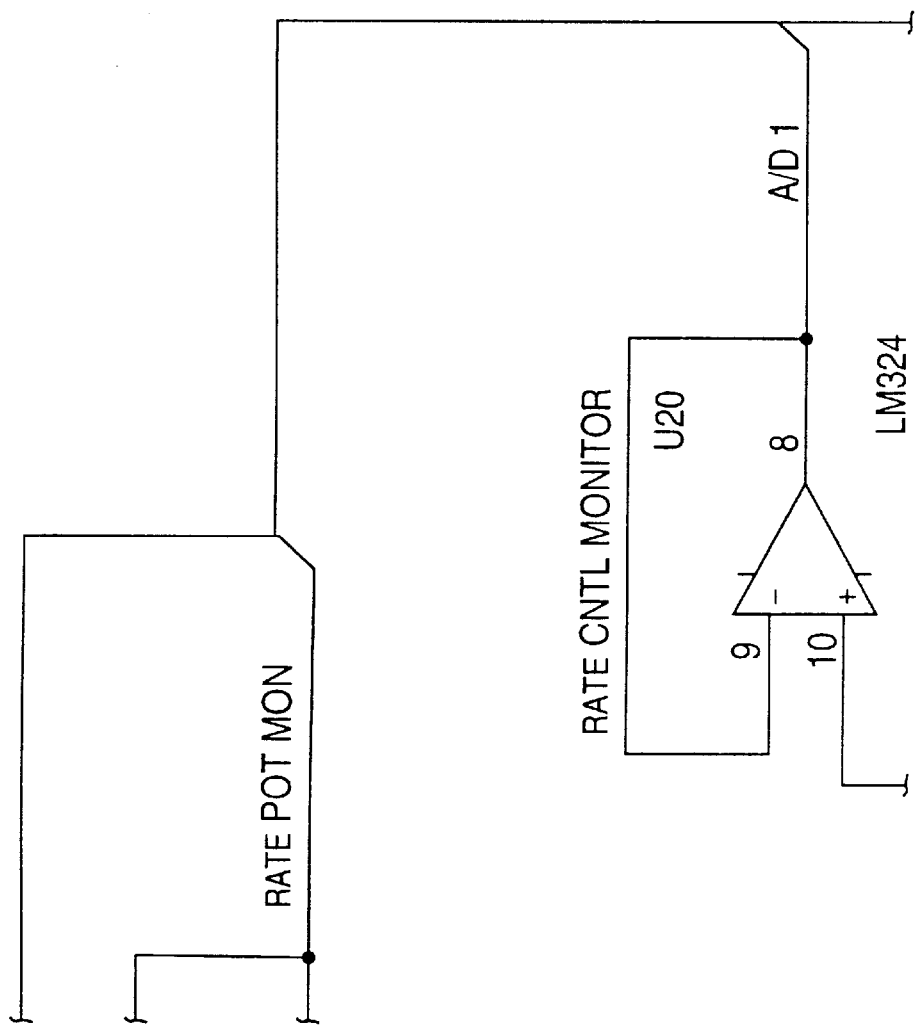
Figure 15F:
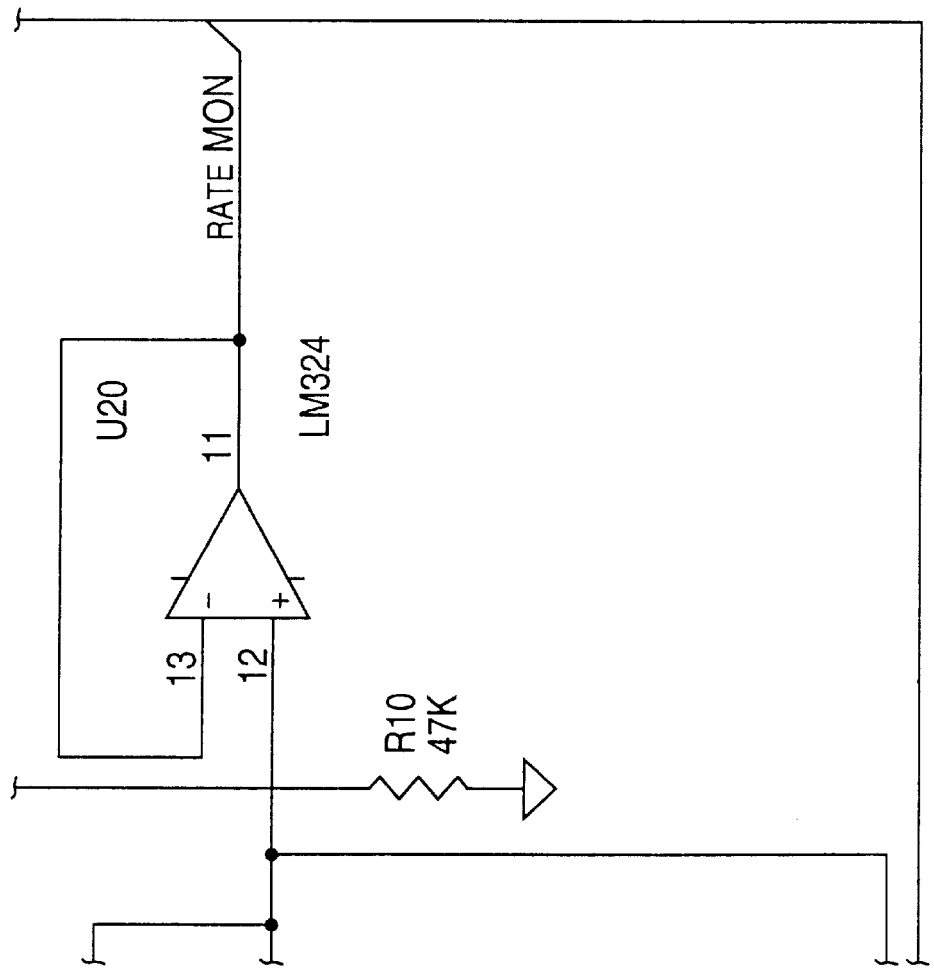
Figure 16:
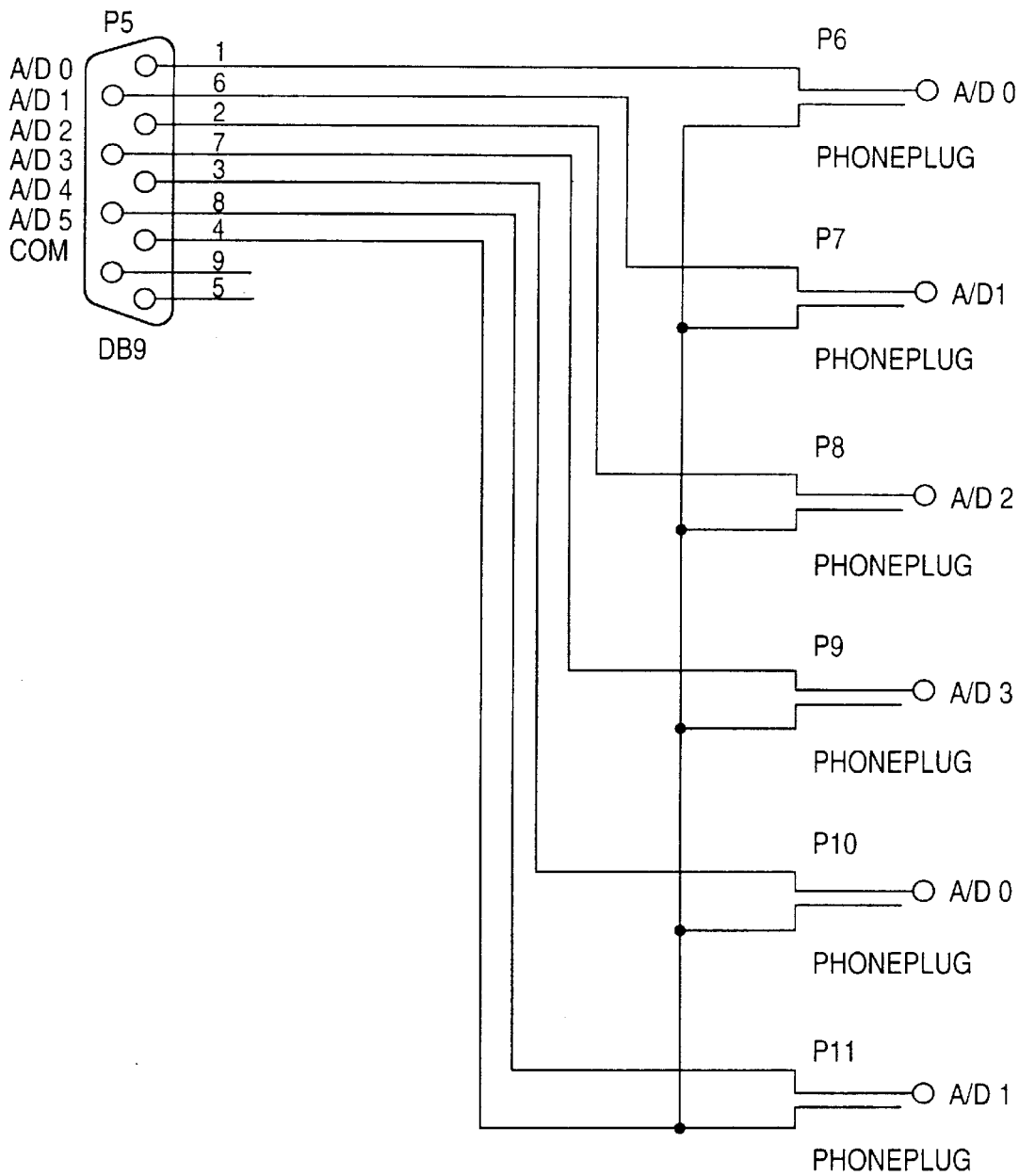
Figure 17:
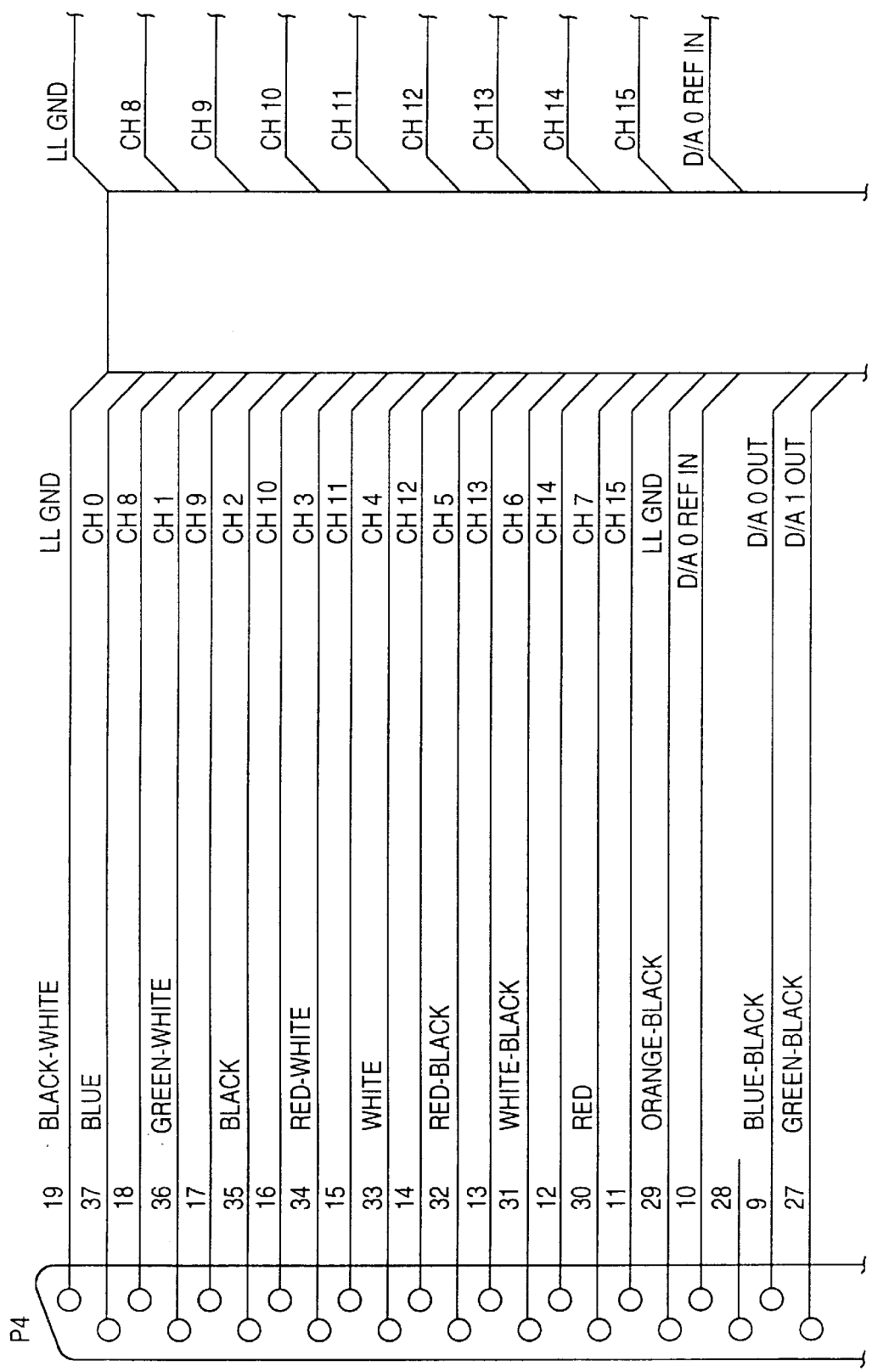
Figure 17B:
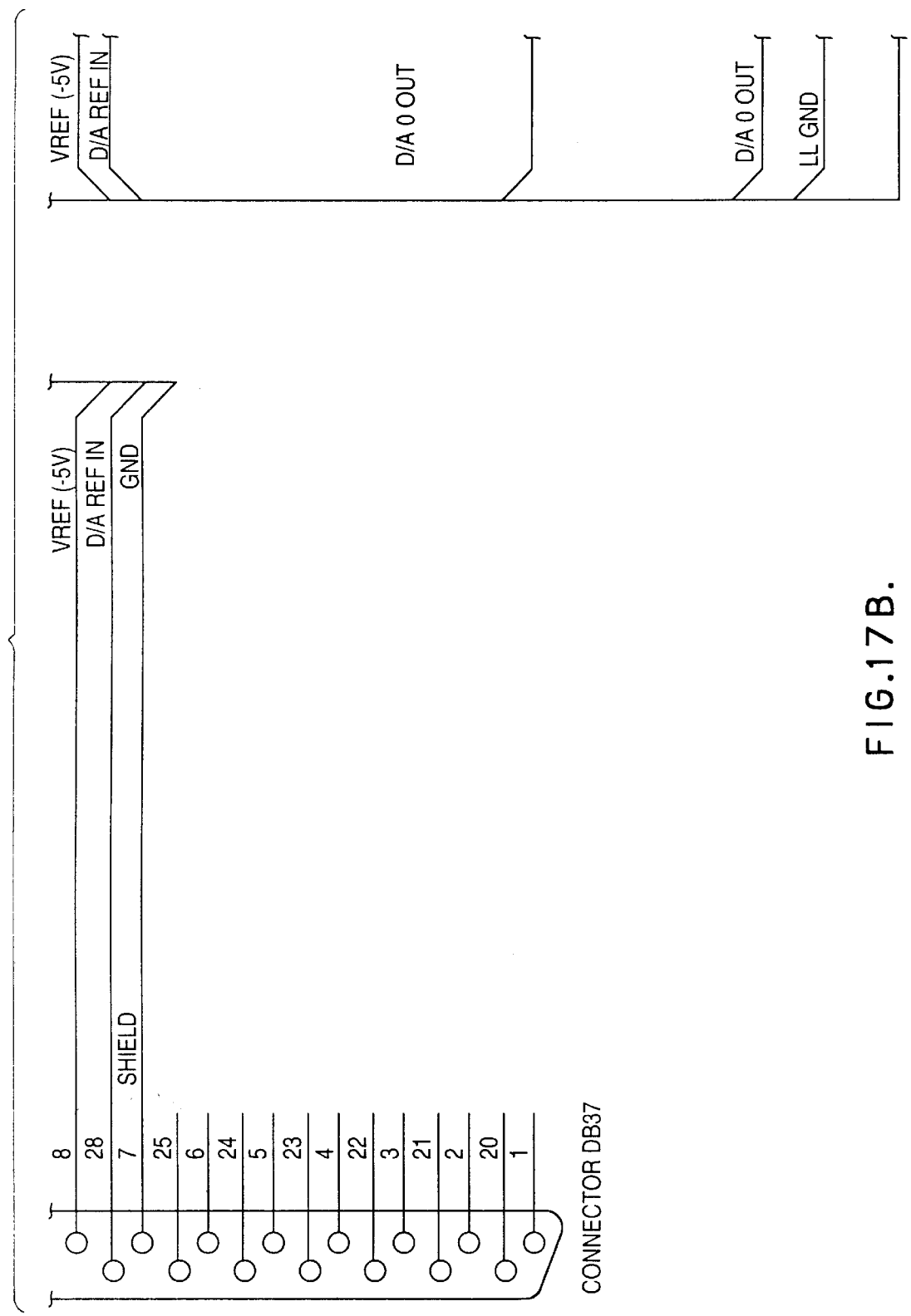
Figure 17C:
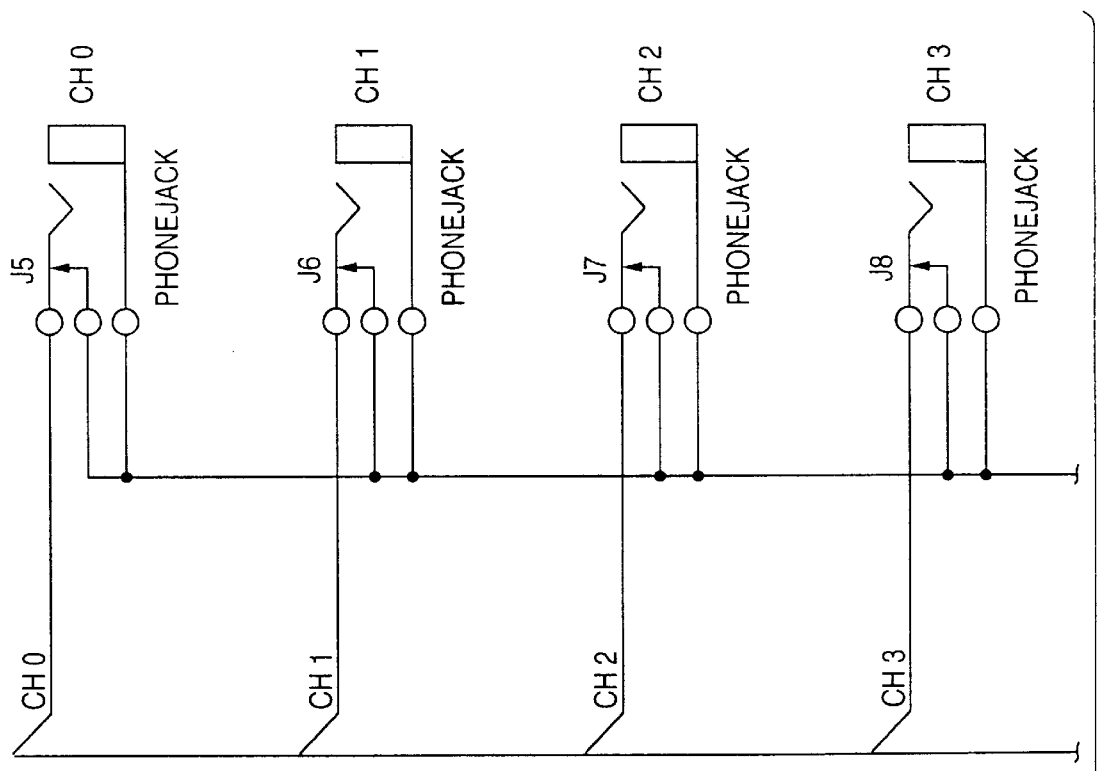

Referring back to connector P2 in FIG. 12: external modulation of 'IE' was disabled (pins 3 and 7 jumpered), and the 2 volt reference (pin 2) was not required.

FIGS. 14A to F and FIGS. 15A to F display the modulation control electronics for 'VOLUME' and 'RATE' respectively. The circuit boards are interchangeable. Referring to FIG. 14, the wiper of the 'VOLUME' control is buffered by amplifier U1D, and coupled to a non-inverting summing amplifier (U1C), whose output is routed back to the 'VOLUME' control's original destination (label 'VOL CTRL' is connected to FIG. 13 amplifier U5D). The 'VOLUME' output at U1D is also routed to the A/D converter channel 0 input (U2A), and the 'VOL POT MONITOR' (U2B), which allows optional monitoring of the Ohio 7000's 'VOLUME' control level before modulation is inserted (J1 on FIG. 2). The modulation reference signal from the D/A converter channel 0 output is buffered and scaled (I1A and U1B) and routed to the other input of the non-inverting summing amplifier (U1C), whose output is also routed to A/D converter channel 1 input (U2C), and to U2D—the 'VOL MONITOR' (J2 on FIG. 12), which allow optional monitoring of 'VOLUME' after modulation is inserted. Since the D/A converter's output is in a range between 0 and 5 volts, the modulation level only increases the 'VOLUME', hence the position of the ventilator's 'VOLUME' control sets the minimum or baseline level of 'VOLUME'.

Figure 6:
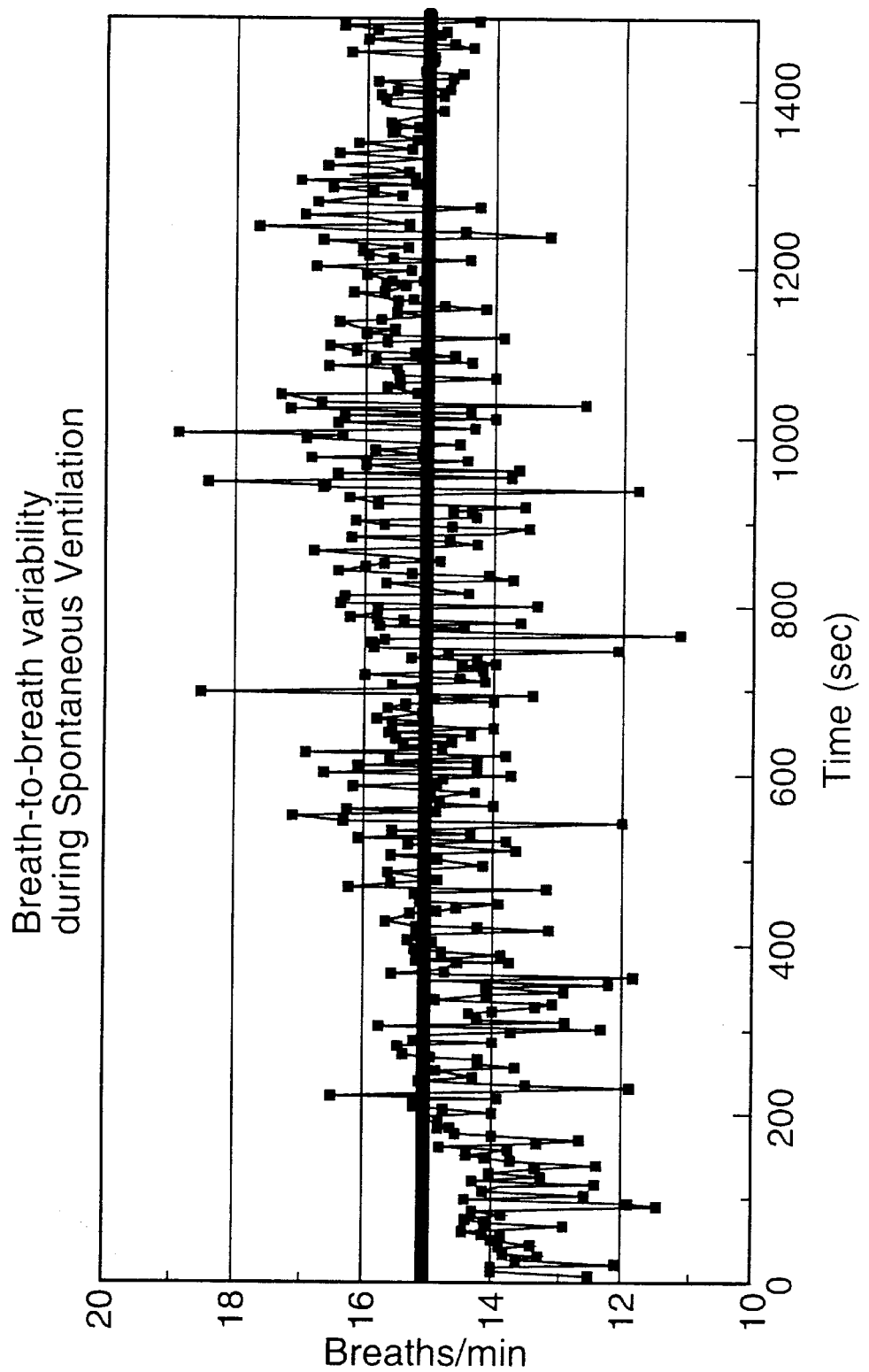
FIG. 6 shows the changes in respiratory rate (breaths/min) over time. Such data is used to create the input file for the ventilator computer controller. These data have a mean rate of 15 breaths/min.
Figure 7:
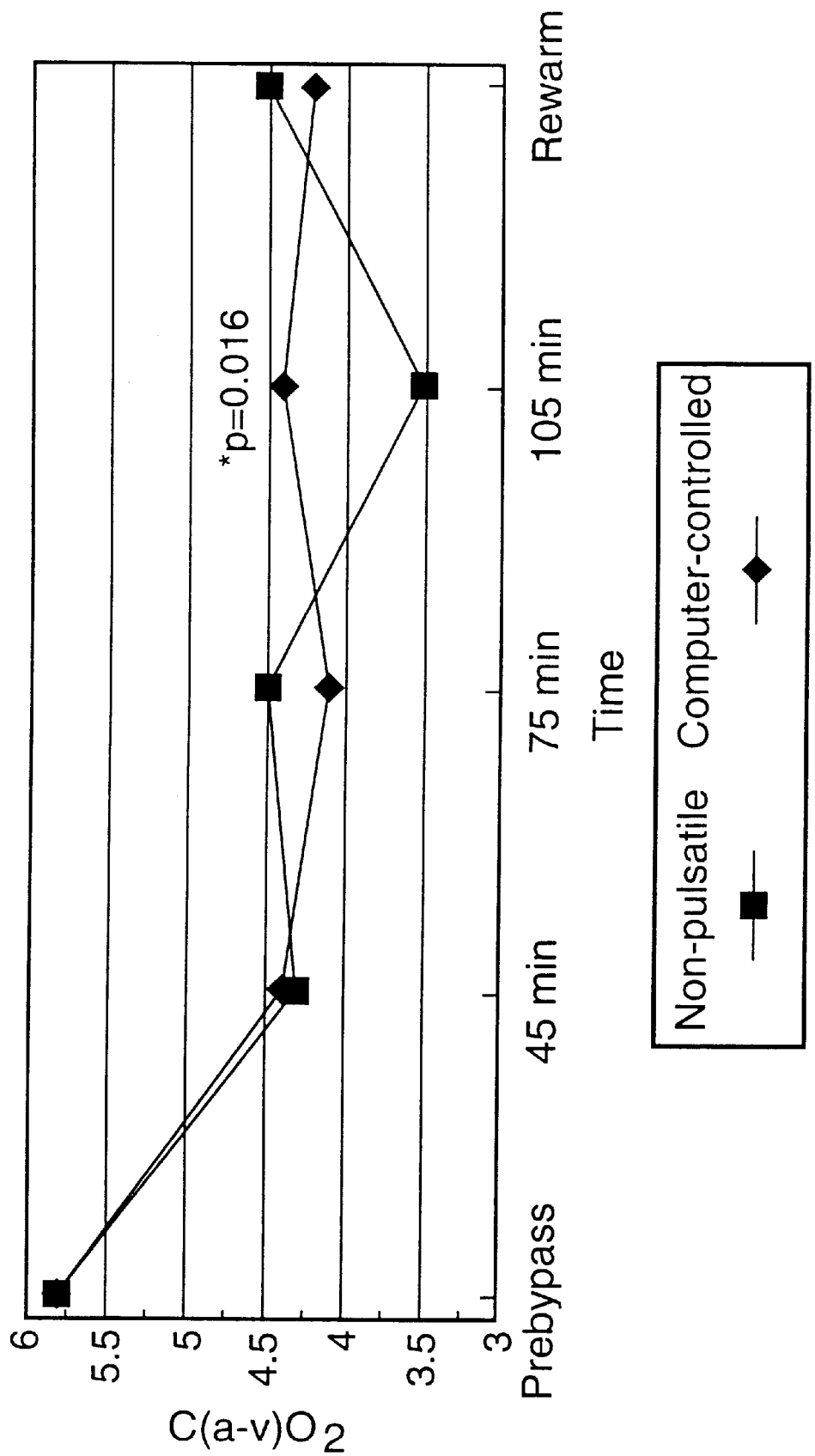
FIG. 7 shows the arterial minus superior sagittal sinus (cerebral venous) oxygen content difference during CPB with computer-controlled and conventional roller pump bypass in dogs (n=6 both groups). The oxygen content difference is stable during conduct of CPB in the computer-controlled group (operation in accordance with the invention). In the control group (conventional roller pump), increased oxygen extraction occurs during the period of rewarming compared to the hypothermic period of CPB immediately before. Such changes in oxygen content difference with rewarming are associated with cognitive impairment following CPB in man.

FIGS. 16 and 17A to D document (FIG. 6) the cable used to interface the Ohio Modulation Unit to the 'DAS16 Jumper Box' (FIG. 7), which is connected to the 37 pin connector on the Metrabyte DASH16 A/D and D/A converter.

DESCRIPTION OF PREFERRED EMBODIMENT

Figure 1:
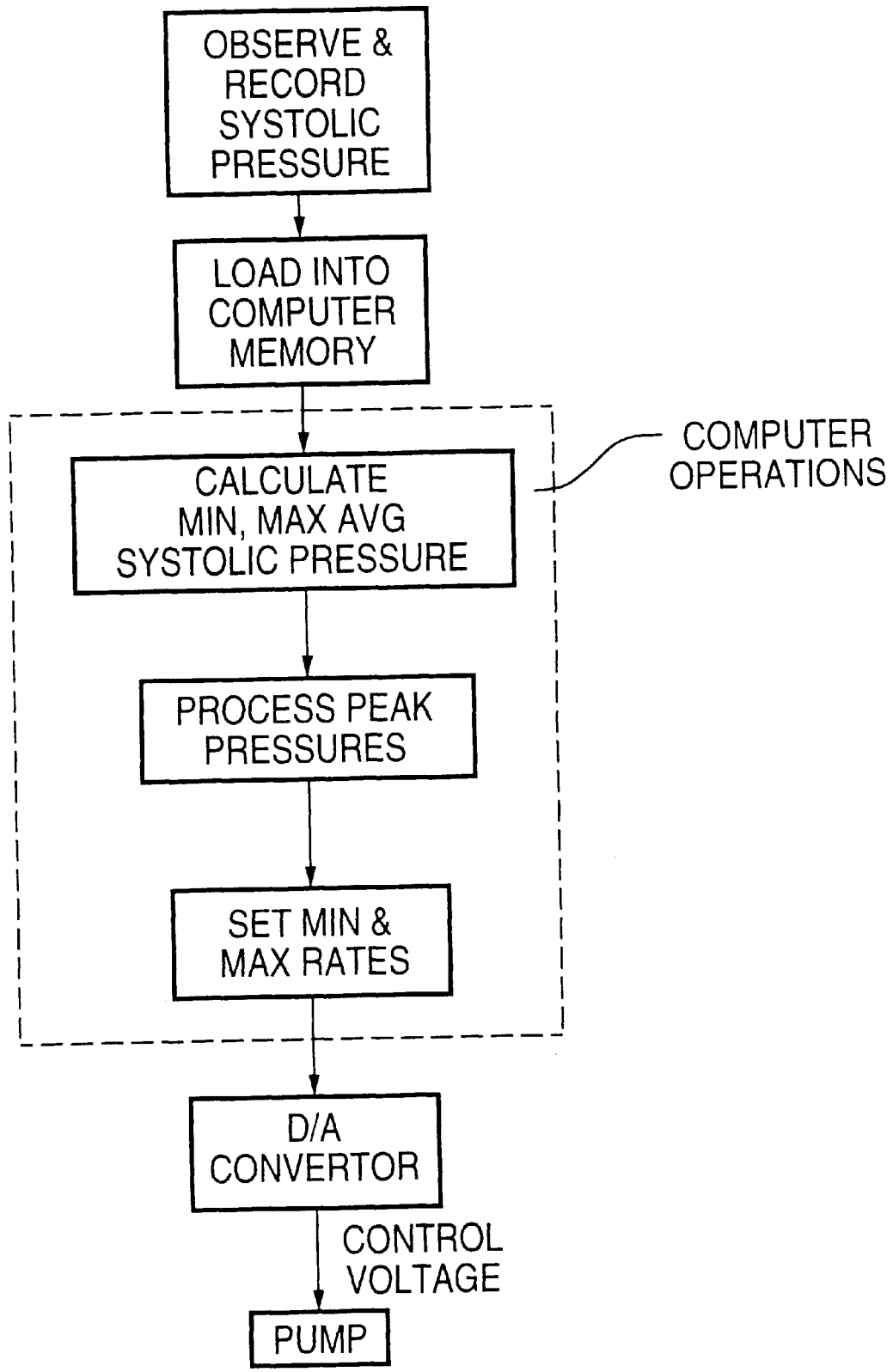
FIG. 1 is a flow diagram showing the various steps of the operation of a CPB pump in accordance with one embodiment of the invention.

In the following description of a preferred embodiment, there is description of the application of the present invention to control of a blood pump. However, it will be understood that the principles described with respect to such blood pump embodiment apply to other devices, including control of ventilators as described elsewhere. The steps involved are shown schematically in FIG. 1.

During a CPB procedure, an electrically-driven pump is used to maintain blood flow, as described above. Generally, a roller pump is employed for this function, in which a pair of diametrically opposed rotating arms engage a flexible tube through which blood is forced by the action of the arms engaging the flexible tube.

Figure 2:
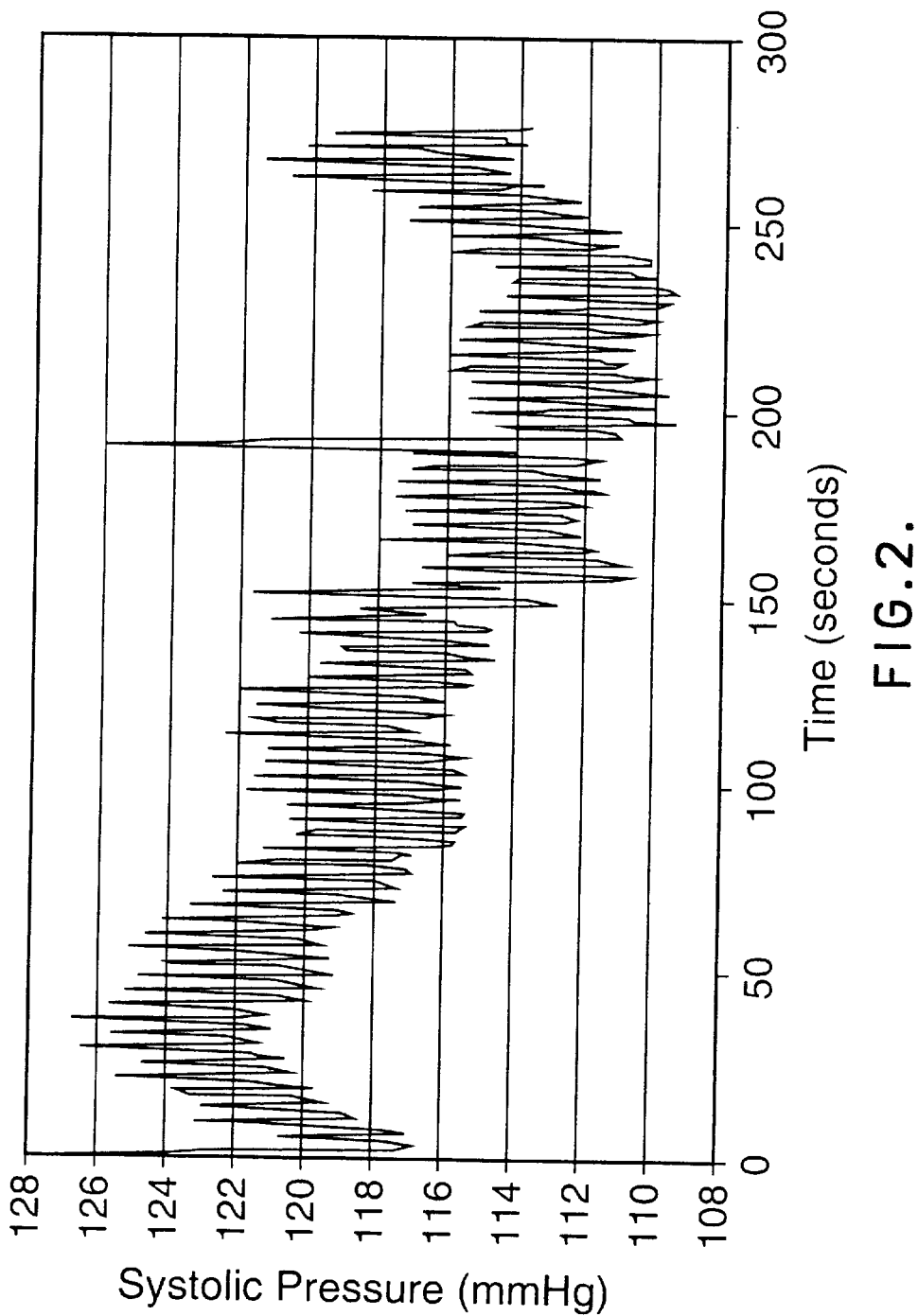
FIG. 2 shows a typical plot of natural variation of systolic blood pressure over time. In this instance, in a dog, data is captured to a data acquisition system from a dog. Following processing, these data are used as an input file for the computer controller used to vary roller pump head revolutions/min based on variability in beat-to-beat intervals and pressure.

An input file for a computer-controller for the pump first is established for the variation of systolic pressure with time for a typical animal, such as a human, a dog or a pig. A typical plot of the gross variation of systolic pressure in mm Hg over time is shown in FIG. 2.

This information, which may contain many thousands of observations of systolic pressure, is loaded into the computer memory and processed by peak height analysis. In this peak height analysis, the maximum, minimum average systolic pressures are determined and may be displayed, the minimum values are removed and the minimum, maximum and average of the remaining peak pressures is recalculated and, if desired, displayed. This information then determines the pulse pressure amplitude and beat-to-beat heart beat variation in the pattern.

Figure 3:
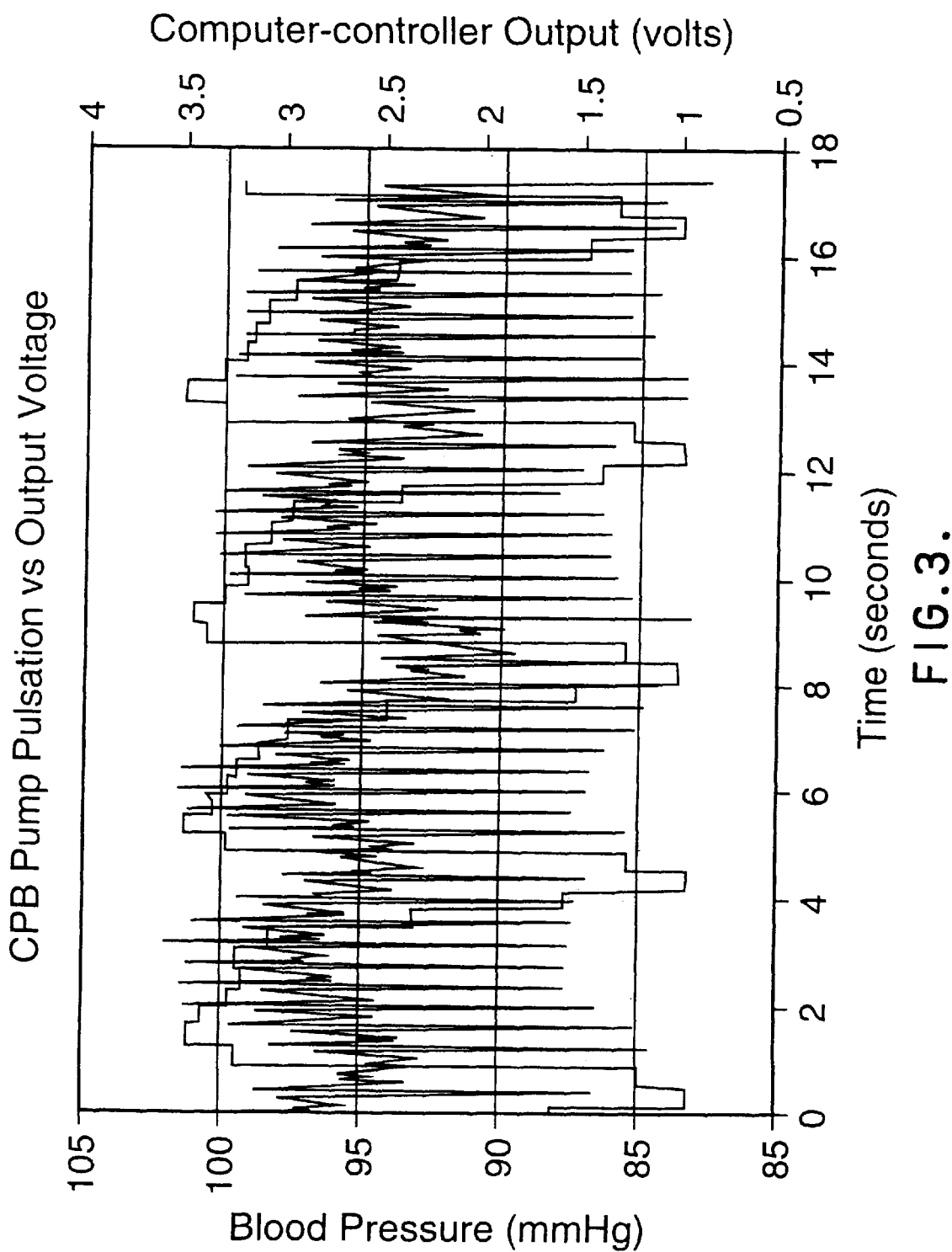
FIG. 3 shows a typical pump pulsation profile for a blood pump controlled in accordance with the invention superimposed upon a plot of peak-to-peak variations in blood pressure derived from a plot similar to that shown in FIG. 2.

The lowest and highest values of the pressure values from the peak-to-peak variation then are established and these values are used to set a minimum and maximum rate for the blood pump, respectively, which then determines the maximum amount of computer modulation. For example, a baseline pressure of 80 mm Hg with a 20 mm Hg variation may be established based on the input file, which then provides a peak pressure ranging from 80 to 100 mm Hg. The computer digital output signal corresponding in magnitude to a peak-to-peak value above the minimum is connected through a digital-to-analog (D/A) converter, which produces an analog voltage control signal to the blood pump to increase the blood pump rate. The computer generates a voltage on the D/A converter proportional to the peak pressure variations for a time proportional to the beat-to-beat interval. The voltage then is used to increase the rpm of the pump from the minimum or baseline setting. The data stored in memory is converted into time steps and relative amplitudes from 0 to 100%. For each time step, the D/A drive is held at the relative level until the next time step occurs. A typical pump pulsation profile superimposed upon a plot of peak-to-peak variations in blood pressure is shown in FIG. 3. As may be seen in FIG. 3, over a period of approximately 18 seconds, the computer-controller output varies between 1 and 3.5 volts. The changes in roller pump speed has resulted in escalations in blood pressure varying between 82 and 102 mm Hg. The data stored in memory is initially scanned in a forward direction for observations 1 to N. As necessary, the data is reverse scanned continuously from observations N−1 to 1 and then forwards from 2 to N. etc. until the program is terminated.

Figure 4:
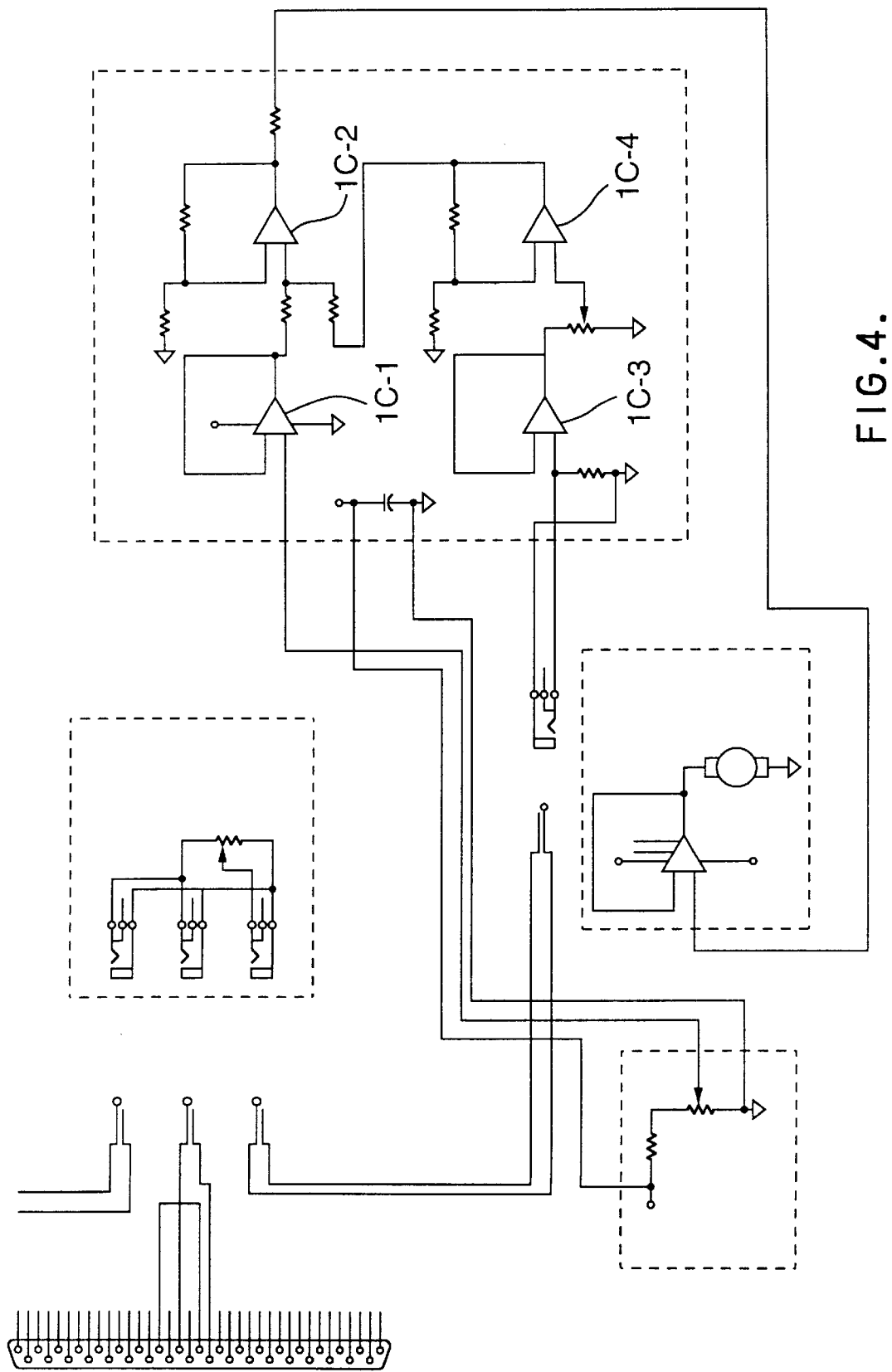
FIG. 4 shows typical circuitry for computer control of a blood pump motor according to the invention.
Figure 5:
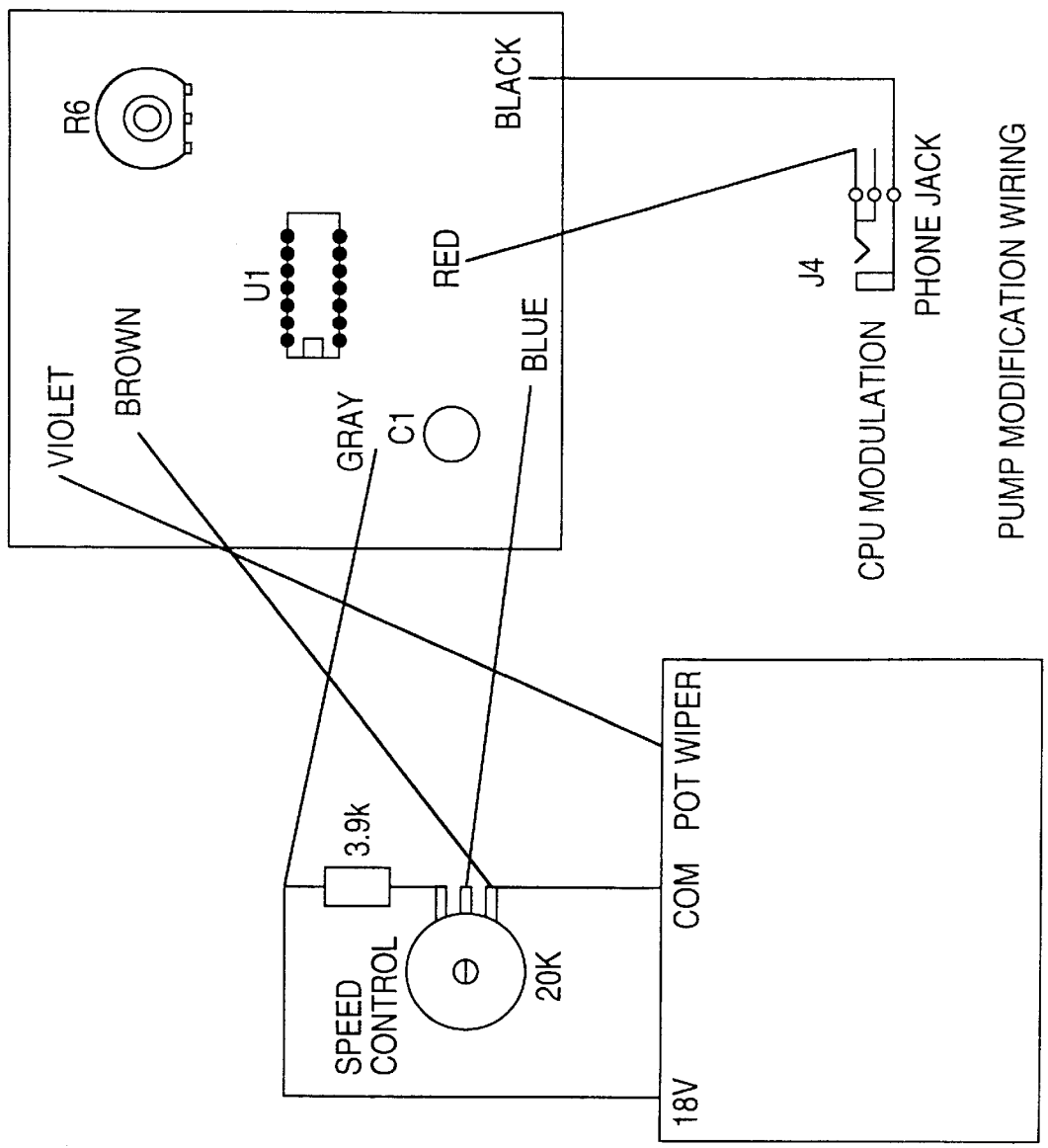
FIG. 5 shows a wiring diagram for a blood pump motor.

Any convenient form of the pump controller may be employed to receive the control signals from the computer and the corresponding voltage signals from the D/A converter. A typical circuitry is shown in FIG. 4 while a wiring diagram appears as FIG. 5. In this circuit, a non-inverting summing amplifier with input buffering is provided, power to operate the amplifier is from the roller pump rate controller. The signal from the original speed control is buffered by a buffer (IC-1), which is applied to one input of a summing amplifier (IC-2). The other input of the summing amplifier is received from the computer modulation signal received from the D/A converter via an external scaling box through buffer IC-3 and amplifier IC-4, which permits an increased voltage range, according to the desired multiple of the amplification, to be applied to the pump servo motor than provided by the D/A converter.

In this way, the roller pump revolutions/min are altered to recreate the pattern of spontaneous biologic variability in the heart function.

The computer operations described above may be effected on any convenient computer hardware programmed in any desired manner to effect the analysis described above to provide the blood pump control voltage. A program which may be employed, named Purfus, has the listing appearing in Table 1 below.

A configuration file, named Purfus Cfg, is necessary for the operation of Purfus program. This file contains a number corresponding to the base address of the D/A converter card:

| Decimal | Hex |
|---------|-------|
| 768 | 300 H |
| 784 | 310 H |
| 800 | 320 H |

Computer control of a ventilator to apply the principles of the invention thereto may be effected using the computer program shown in Table 2 below. This software allows the 'RATE' and the 'VOLUME' settings of the ventilator controls to be modulated independently via a data file, generated before hand and in a form such as appears in FIG. 6.

In order to implement computer control of the ventilator using the circuitry shown in FIGS. 11 to 17, a means of converting voltage to ventilation 'RATE' and 'VOLUME' is provided. A linear regression analysis of the ventilator's 'RATE' and 'VOLUME' potentiometers output voltage versus dial calibrations is performed ($R^2 = 0.9996$). Functions are converted 'RATE' and 'VOLUME' into voltage, and vice-versa. By control loop scanning the A/D converter channel in the background using the high speed DMA facility, the current setting of the ventilator's 'RATE' control is acquired. If the modulation level for the current time step is greater than the baseline (set by the current setting of the ventilator's 'RATE' control), the D/A converter channel generates a voltage level, which is passed to the summing amplifier in the Ventilator Modulation Unit, necessary to increase the current baseline value of 'RATE' to the modulation level of 'RATE'. The output of the summing amplifier is then sampled by another A/D converter channel, converted into 'RATE', and displayed on the computer screen. The 'VOLUME' are updated in each 'loop' of the control program which executes every 400 milliseconds on a 'control' computer (a 4.77 MHz 8088 processor with a 8087).

EXAMPLES

Example 1

This Example illustrates the methods and materials used in ventilation experiments carried out on pigs.

Pig Preparation:

Thirteen (13) pigs weighting 20 to 30 kg were studied. All pigs received atropine 0.6 mg and ketamine 10 mg/kg intramuscularly for induction of anesthesia. Once sedated, isoflurane in oxygen was administered by face mask. When airway reflexes had been obtunded, the pig was intubated with a 6.0 mm endotracheal tube. Mechanical ventilation was instituted with an Ohio 7000 anesthesia ventilator at 15 breaths/min with the minute ventilation adjusted to maintain the end-tidal $CO_2$ at 35 to 40 mm Hg. Isoflurane was administered at 2.0 percent end-tidal in oxygen during surgical preparation. Lactated Ringer's was infused IV at 10 ml/kg/hr during the experiment. Pancuronium bromide was administered IV intermittently for muscle relaxation.

The animal was turned supine and a cutdown performed in the groin. A double-lumen catheter was placed in the femoral artery for intermittent sampling of blood for arterial blood gases (ABG) and continuous recording of arterial pressure. A 7.5 Fr pulmonary artery catheter was inserted via the femoral vein and advanced with the balloon inflated until a pulmonary capillary wedge pressure (PCWP) was obtained. Pulmonary artery pressure was continuously recorded. Mixed venous blood was sampled from the distal end of the pulmonary artery catheter. Cardiac output (CO) was measured intermittently, by thermodilution, following 5 ml injection of room temperature saline (performed in triplicate). Following surgery, the animal was allowed to stabilize for 30 minutes and the isoflurane concentration was reduced to 1.5 percent end-tidal.

Baseline hemodynamic and respiratory measurements were then obtained. These included measurements of mean arterial pressure (MAP), mean pulmonary artery pressure (MPAP), PCWP, airway pressures at the proximal end of the endotracheal tube (all recorded to a Gould 2600 oscillograph and to an advanced CODAS data acquisition system), and CO. Gas measurements included arterial and mixed venous blood gases and end-expired gas sampled from the expiratory limb of the anesthesia circuit. These were measured using a Radiometer ABL3. Arterial and mixed venous oxygen content, oxygen saturation and hemoglobin concentration were measured with a Radiometer OSM3 set for porcine blood. All measurements were obtained in duplicate. Calculated indices included pulmonary vascular resistance (PVR), dead space ventilation (VD/VT) and shunt fraction (QS/QT).

Oleic Acid Lung Injury: After the above measurements were obtained a Valsalva maneuver was done (mean airway pressure 30 cm $H_2O$ for 5 seconds). An infusion of oleic acid was started at 0.2 ml/kg/hr through the infusion port of the pulmonary artery catheter. At 5 min intervals the Valsalva maneuver was repeated and 1min later an arterial blood gas obtained. The oleic acid infusion was continued until the $PaO_2$ decreased to $\leq 200$ mm Hg for 2 consecutive measurements. At this point the infusion was stopped and the volume infused noted. Following repeat hemodynamic and respiratory measurements as above, the animals were randomly allocated to one of two ventilatory modes; conventional IPPV with the respiratory rate (RR) fixed at 15 breaths/min with the minute ventilation (MV) changed to maintain $PaCO_2$ at $\leq 45$ mm Hg (control), or IPPV with a computer-controller with variable RR but with a mean of 15 breaths/min (computer). Again, MV was adjusted to maintain $PaCO_2$ at $\leq 45$ mm Hg. Ventilation continued with either the control or computer mode for the duration of the experiment. Every 30 minutes for 180 min, hemodynamic and respiratory data was obtained as above in duplicate. At 180 min, airway pressure data was acquired to the data acquisition system over a 2 min time period to sample approximately 30 consecutive breaths.

Figure 9:
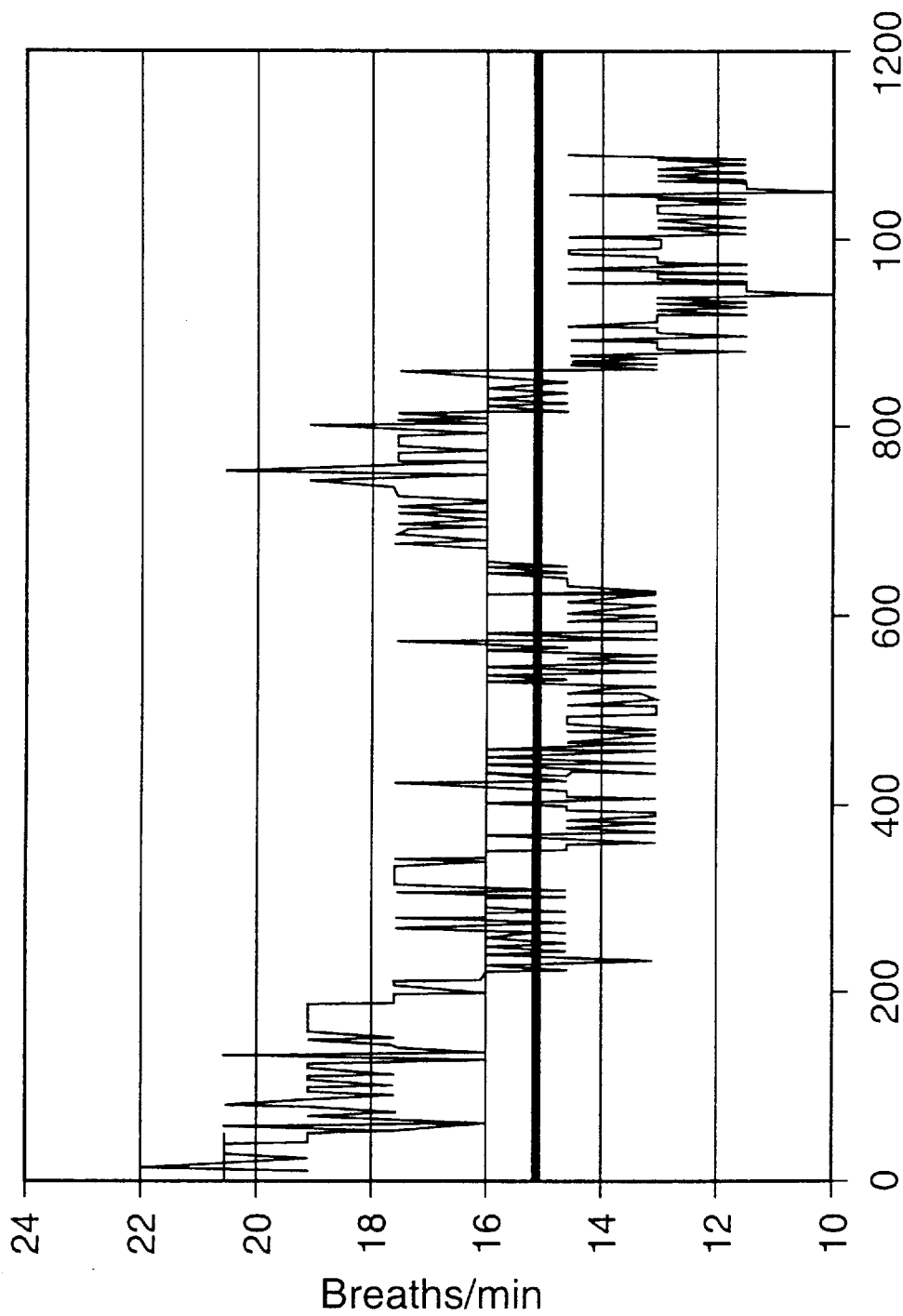
FIG. 9 is similar to FIG. 6 and shows the changes in respiratory rate (breathes/min) over time as well as the mean value.
Figure 10:
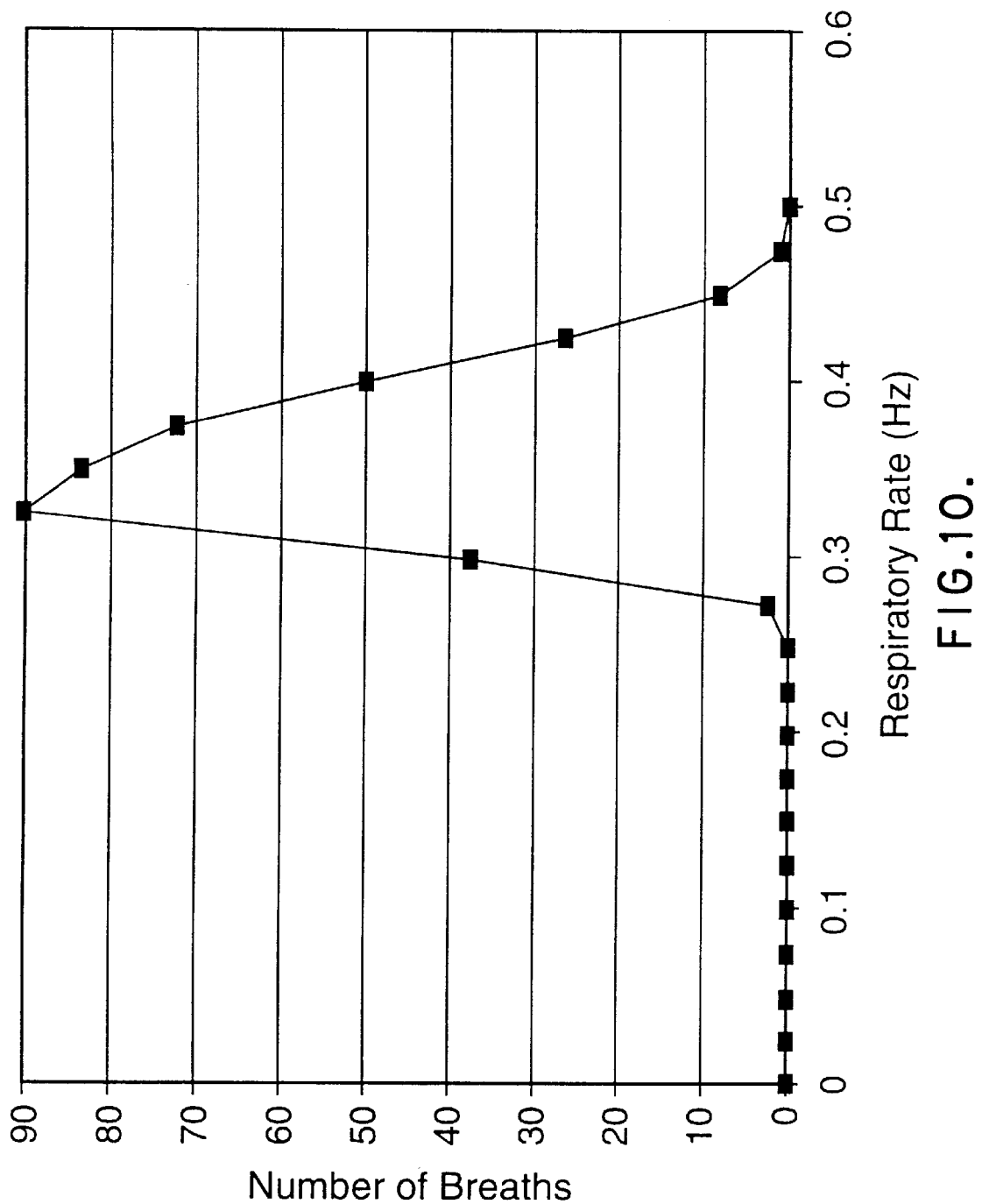
FIG. 10 shows a frequency vs respiratory rate plot devised from the graph of FIG. 9.
Figure 11:
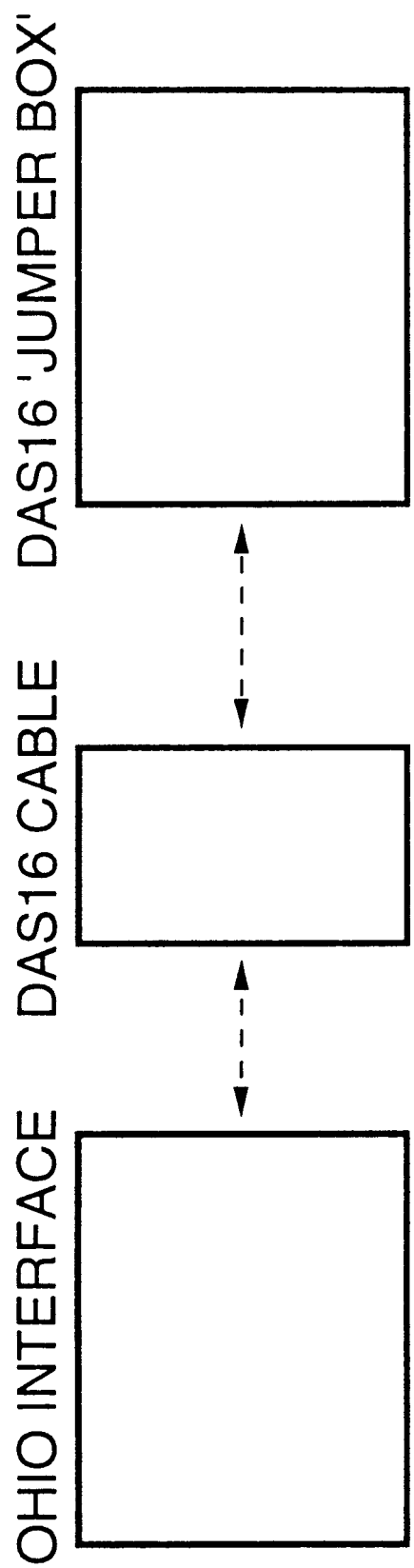
FIG. 11 is a block diagram showing the overall signal flow to the ventilator (Ohio 7000) used in the Examples described below. The 'Ohio Interface' module is connected to the Metrabyte DASH16 analog to digital (A/D) converter via bi-directional control lines via the 'DAS16 Cable' and 'DAS16 Jumper Box'.

Computer-controlled Ventilation: The ventilation used in this experiment was an Ohio 7000 having electronics as illustrated in FIGS. 11 to 17 described above. The computer-controller software (Table 8) allows the rate and volume settings of the ventilator controls to be modulated independently via a previously generated data file. Data from this modulation file is depicted graphically in FIG. 9. A frequency vs respiratory rate plot is shown in FIG. 10. The modulation file was generated from hemodynamic and respiratory excursions from an anesthetized dog. This information was captured by data acquisition, processed and scaled to produce breath-to-breath variability. Ventilatory variability can also be measured directly, stored and subsequently used to control the ventilation. Hardware was also developed to implement computer-control of the ventilator which necessitated converting voltage outputs from the breath-to-breath variability period to control ventilator respiratory rate and tidal volume, as seen in FIGS. 11 to 17. In this experimental configuration, only RR was changed. As there was employed a ventilator which functioned as a volume divider, change in the RR resulted in reciprocal changes in the TV. Functions were developed to convert ventilator rate and volume into voltage and vice versa. Output to control RR was updated every 400 msec and changed accordingly based on the modulation data file. The computer ventilator RR was set to 10 breaths/min baseline and the modulation file programmed ventilation from 10 to 22 breaths/min with a mean value of 15 breaths/min.

Post-hoc analysis: The data file of airway pressures was processed to integrate the area under the pressure time curve to give mean airway pressure. Mean peak airway pressure was also calculated. Because of the variability in RR and TV in the computer-controlled ventilator group, a minimum of 25 breaths were analyzed in each experiment. At the end of each experiment, the animal was killed with a lethal dose of thiopental, and a sternotomy done to remove the lungs. The lungs were weighed wet and then suspended and aerated to commence drying. The following day, the lungs were placed in an oven to dry to a stable weight (±5 percent on consecutive days). The wet:dry lung weight ratio was calculated.

Statistical Analysis: Multiple comparisons of data within and between groups was with repeated measures ANOVA. A p-value $\leq 0.05$ was considered significant for group x time interactions or differences between groups. Least squares means test matrices were generated for post-hoc comparisons. Bonferroni's correction was applied when multiple comparisons were examined within groups. Single comparisons between groups were by Student's t-test, p<0.05 considered significant.

Example 2

This Example provides the results of the experimentation described in Example 1.

The computer-controlled ventilator varied respiration from 10 to 22 breaths/min (mean ± SD; 15.0±2.3). There were 369 RR and TV combinations over 1089 sec before the modulation file looped to repeat itself.

The demographic data from the experiments is shown in Table 3 below. There were 7 animals in the computer group and 6 in the control ventilator group. The animals in the two groups did not differ for weight or in the amount of oleic acid infused to induce the lung injury. The mean airway pressure did not differ between groups nor did the mean peak airway pressure. There was no difference between groups in the wet:dry lung weight ratio.

There was no difference between groups for blood or nasopharyngeal temperature (group x time interaction; p=0.1772 and 0.2665 respectively) (Table 4 below). A group effect was seen for baseline blood temperature of 0.6 degrees. In both groups, temperature increased significantly following lung injury. A marked difference was seen between groups for hemoglobin concentration (p =0.0014 group x time interaction). In both groups hemoglobin increased significantly following lung injury, but continued to increase in the control group. There was no interaction for pH between groups (p=0.2325) but there was a group effect with lower pH in the latter periods of the experiment in the control group.

Hemodynamic data is shown in Table 5 below. The MAP was stable between groups (group x time interaction; p=0.4429). In both groups MAP decreased significantly following lung injury. The MPAP showed an interaction (p=0.0198). In both groups the MPAP increased markedly following oleic acid. Baseline MPAP was significantly higher in the computer group then lower by 90 minutes. The PCWP was essentially identical between groups. No interaction was seen for PVR but a marked group effect was seen (p=0.0001). In both groups PVR increased dramatically with lung injury. The PVR was significantly higher from 90 min on in the control group. There was no difference between groups for cardiac output at any time period. In both, the CO decreased to about 60 percent of control and remained unchanged.

Respiratory gas data is shown in Table 6 below. End-expired $CO_2$ ($PeCO_2$) did not differ between groups. There was a significant increase in $PaCO_2$ following lung injury in both groups. This correlated to the significant increase in dead space ventilation (VD/VT) seen. Importantly, a significant group x time interaction was seen for $PaO_2$ (p=0.0448). A markedly significant group effect was seen as well (p=0.0001). This is evident from significantly greater $PaO_2$ at time periods 60–150 min after oleic acid infusion. Of note, at baseline and at Time 0, $PaO_2$ values are not significantly different. In both groups the shunt fraction (QS/QT) increased significantly following lung injury.

Example 3

This Example discusses the results obtained in the experiments described in the preceding Examples.

In these experiments described in Example 2, it has been demonstrated that oxygenation is improved by modifying mechanical ventilation to incorporate biologic variability. Through use of a computer-controller, variability in RR and TV resulted in significantly improved $PaO_2$ compared to standard IPPV with the same ventilator. This improvement in oxygenation was accomplished without an increase in mean airway or mean peak airway pressures.

No differences were seen between the two groups for amount of oleic acid administered to injure the lungs. The wet:dry lung weight ratios suggest a similar injury between the two groups. The two groups were very similar at baseline and following lung injury for PCWP, CO and PVR. Similar increases in shunt fraction and dead space ventilation were also seen for these two groups over the same time periods. Thus, the two groups appear not to differ prior to being randomized to control or computer-controlled ventilation.

Figure 8:
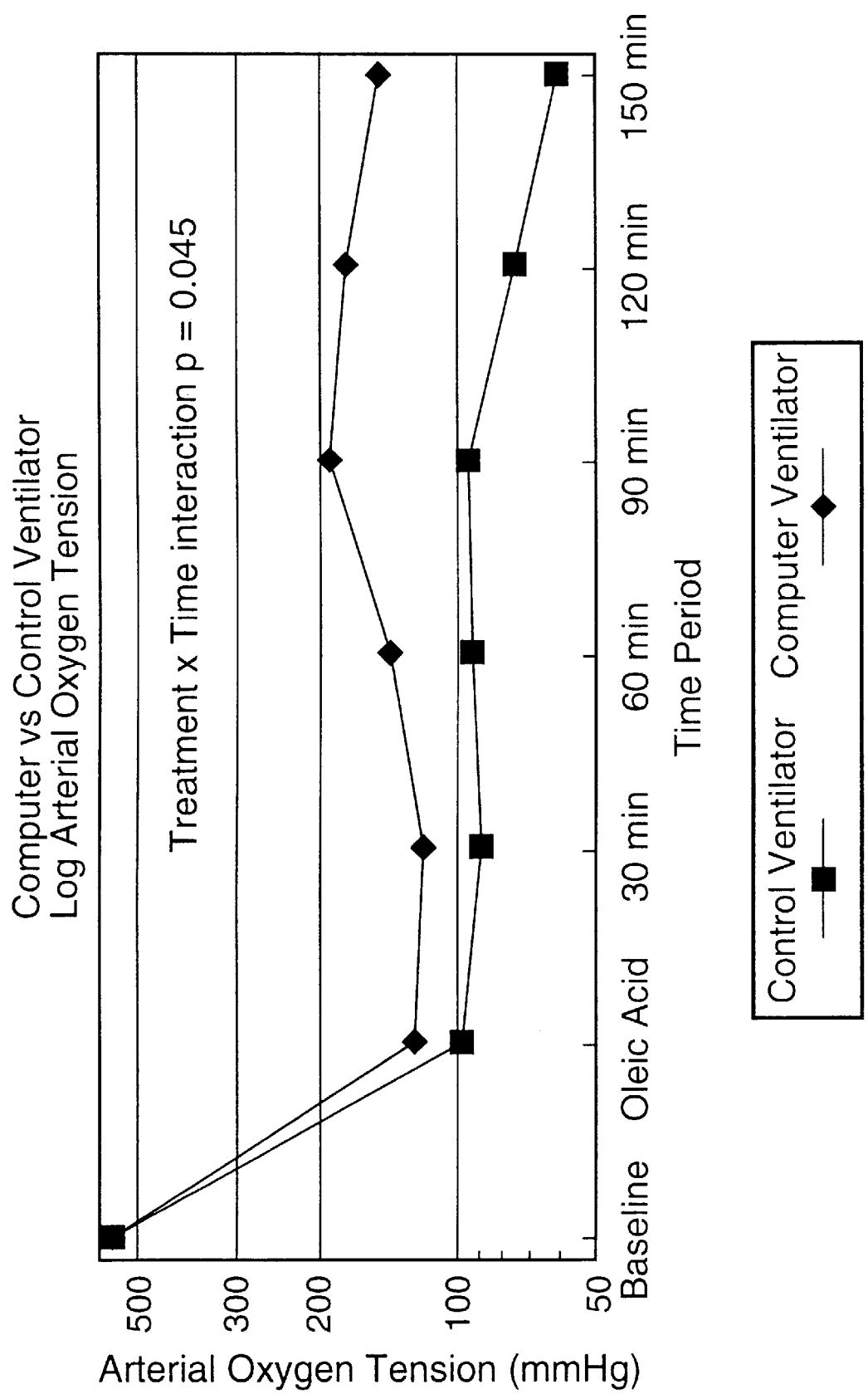
FIG. 8 shows a comparison of arterial oxygenation ($PaO_2$ in mm Hg) for computer-controlled vs. conventional mechanical ventilation in a porcine oleic acid lung injury model. Significantly greater $PaO_2$ is seen at the latter time periods in the experiment in animals ventilated with the computer-controlled ventilator (operation in accordance with the invention).

As configured for this study, the ventilator delivered 369 different RR and TV combinations with a mean RR of 15 breaths/min over 1089 sec (18.2 min). This is contrasted to a single RR of 15 breaths/min throughout the duration of the experiment in the control group. Some variability exists in the control group because MV was adjusted to attempt to maintain $PaCO_2 \leq 45$ mm Hg when VD/VT increased with lung injury. However, this entailed only a maximum of 6 changes in MV, over the course of any one experiment, when MV was changed if $PaCO_2$ was out-of-range, at the end of any 30 min measurement period. Thus, over a 30 min measurement period, RR and TV were essentially fixed in the control group but there were 369×30/18.2=608 different RR and TV combinations in the computer group. If, as Suki et al. (Nature, Vol. 368, April 1994, p. 615–618) suggest, airway recruitment is stochastic, then the probability of airway opening is dramatically improved using the computer-controlled ventilator. The experimental results provided herein indirectly suggest that this finding is so. Of greatest significance is that mean $PaO_2$ improved following lung injury in the computer group out to 150 min (FIG. 8) compared to an inexorable decline in $PaO_2$ in the control group. This improved $PaO_2$ was associated with significantly lower MPAP and PVR at identical PCWP in the computer group suggesting better ventilation/perfusion matching and lower pulmonary vascular resistance at similar cardiac outputs. The marked difference in hemoglobin concentration following lung injury is an independent marker that the two ventilatory modes differ. The increasing hemoglobin concentration in the control group suggests further accumulation of lung water. In the computer group, hemoglobin concentration remained essentially stable. This is especially so as the initial mean increase in hemoglobin concentration is identical in the two groups (26 percent). At Time 0, both groups were control mode ventilated. Only after Time 0, was computer ventilation initiated. Therefore, by inference, during the conduct of the experiment, lung water accumulation was less in the computer group with associated better oxygenation.

Example 4

This Example illustrates the materials and methods used to evaluate a CPB pump in dogs, using the computer control operation described above with reference to FIGS. 1 to 4.

Experimental Preparation: Twelve mongrel dogs (21±3 kg) were studied. All animals were anesthetized with sodium thiopental (25 mg.kg$^{-1}$). The trachea was intubated and the animal ventilated with $O_2$. The minute ventilation was adjusted to maintain $PaCO_2$ at 35 to 40 mm Hg. The dog was positioned in a stereotactic head-frame in a modified sphinx position. Bipolar EEG electrodes were placed over the parietal hemisphere bilaterally and monitored by an Interspec Neurotrac® in raw EEG mode. Temperature was measured in the nasopharynx using a calibrated YSI telethermometer®. Anesthesia was maintained with isoflurane 1.3% end-tidal (1 MAC) during the surgical preparation. Following thoracotomy, the isoflurane was discontinued for a minimum of 30 min and the EEG made isoelectric with a bolus of thiopental. A continuous infusion of thiopental was initiated at 10 mg.kg$^{-1}$.hr$^{-1}$ to maintain the EEG isoelectric during CPB. Neuromuscular relaxation was achieved with pancuronium bromide.

A flow-directed catheter was advanced through the left femoral vein into the right atrium for central venous pressure (CVP) monitoring. A femoral artery catheter was advanced into the distal aorta for arterial pressure (MAP) monitoring. A double lumen (7.5 FR) catheter was inserted into the left brachial artery for intermittent blood withdrawal. The superior sagittal sinus (SSS) was exposed by trephine and the posterior one-third was cannulated non-occlusively by insertion of a 22-gauge intravenous catheter. Continuous cerebrospinal fluid pressure (CSFP) measurements were recorded by inserting a 22-gauge spinal needle into the cisterna magna with the use of a micromanipulator (Narishige®). A right thoracotomy was performed. The right atrium and proximal aorta were cannulated with a single stage 38 Fr atrial and Jostra® 21 Fr or 24 Fr aortic cannula, respectively. Following the initiation of CPB, the left ventricle was vented by a cannula inserted through the right superior pulmonary vein and the proximal aorta was occluded with a Seldinger vascular clamp.

All blood pressures and the CSFP were measured by calibrated Abbott® transducers referenced to the intra-auricular line. Data were recorded continuously on paper by an oscillograph (recorder model 7754A®, Hewlett Packard) and intermittently on hard disk by an IBM PC-AT® computer based data acquisition system (Dataq Instruments®). The latter data are reported. Arterial and SSS blood gases were measured before and after each microsphere injection by an ABL-3 Acid-Base Laboratory (Radiometer®) at 37° C. and not corrected for temperature. Arterial and cerebral venous (SSS) oxygen content and hemoglobin were measured by Radiometer OSM-3 (specific for canine blood).

Cardiopulmonary bypass was conducted utilizing a Travenol® non-pulsatile roller pump with a Terumo Capiox E membrane oxygenator and a Bentley® arterial line filter (25 μm). The roller pump and oxygenator were primed with 2.5 to 3.01 of lactated Ringer's and 1 to 2 units (500 to 1000 ml) of canine whole blood in CPDA-1 solution. The blood was obtained 48 to 72 hours prior to the experiment from a donor animal and refrigerated at 4° C. The animal was systemically heparinized with 300–400 IU·kg$^{-1}$ of heparin (Organon: porcine intestine®) and additional doses as required, to give an activated clotting time (ACT)≧400 sec (Hemochron 400®). Throughout the experiment the animal had an intravenous infusion of lactated Ringer's at 200–250 ml.hr$^{-1}$ containing 25 mEq.l$^{-1}$ of $NaHCO_3$. This was done to maintain a stable hemoglobin concentration and acid-base state during the experiment (α-stat acid-base management). Norepinephrine (40 μg) was injected into the oxygenator coincident with initiating CPB to minimize the hemodynamic consequences. The animals were randomized to one of two groups: non-pulsatile bypass group; Group NP (n=6), or computer-controlled bypass group; Group CP.

Group CP (n=6). Following the initiation of CPB, cooling to 28° C. commenced immediately in both groups. Temperature was altered using a Travenol heat exchanger. In both groups of animals, the mean cerebral perfusion pressure (CPP; MAP—mean CSFP) was maintained at greater than 60 mm Hg. Hypothermic non-pulsatile CPB continued for 105 min in Group NP and for 15 min in Group CP while the computer-control was being established (see below) and then for 90 minutes with computer pulsation. At 105 min, rewarming was commenced. In both groups, rewarming to baseline temperature was over 30 min. At 45 min after the start of rewarming, cerebral blood flow (CBF) and blood gas samples were obtained.

In these experiments, for each animal in Group CP, by means of a data acquisition system, a 15 min data file of blood pressure was obtained following induction of anesthesia. Data from a typical modulation file is depicted graphically in FIG. 2. A typical output from the computer-controller roller pump relating computer voltage output and the changes in MAP are shown in FIG. 3. The data is processed by a computer programmed using Table 1.

Cerebral Blood Flow Measurements: The radioactive microspheres, ultrasonicated in saline, were injected into the arterial cannula, approximately 1 meter proximal to the aortic root, after the $PaCO_2$ was stable between 35–40 mm Hg. If the $PaCO_2$ could not be stabilized in this range by adjusting the $O_2$ flow to the oxygenator, $CO_2$ was added with a Sechrist® mixer. Approximately 2.5×10$^6$ microspheres (15 μm diameter) were injected into the arterial cannula. This number of microspheres assured greater than 400 microspheres/sample for accurate blood flow measurement (Heymann et al., 1977). The randomly selected microspheres were labelled with $^{46}Sc$, $^{85}Sr$, $^{141}Ce$, $^{95}Nb$, or $^{113}Sn$ (New England Nuclear). A Harvard pumps withdrew a reference blood sample for determination of organ blood flow (25 ml) from the brachial artery (Compugamma®) after being weighed. The counts/min were converted to regional CBF in ml.g$^{-1}$.min$^{-1}$ with the use of standard equations.

Total CBF (tCBF) was determined by summing weighted flows to all brain regions and dividing by total brain weight.

Similarly, cerebral hemispheric CBF (hCBF) and brain stem CBF (bsCBF) were determined by the summation of weighted flows to the cerebral hemispheres and brain stem, respectively. The CPP was measured as (MAP—mean CSFP) and cerebral metabolic rate for $O_2$ (CMRO$_2$) as hCBF X (Art—SSS $O_2$ content) in ml $O_2 \cdot g^{-1} \cdot min^{-1}$.

Statistical Analyses: Changes over time for blood gas and hemodynamic variables were evaluated by analysis of variance (ANOVA) for repeated measures. When ANOVA was significant, comparisons were made with the least-squares means test. Data are presented as mean ± SD.

Example 5

This Example describes the results obtained using the materials and methods described in Example 4.

Temperatures and hemodynamic data are shown in Table 7 below. The temperature did not differ between groups for either the period of hypothermia or following rewarming. In all instances, the nasopharyngeal temperature was able to be increased to 35° C. within the 30 min time frame without exceeding a temperature gradient of 8° C. between the heat exchanger and the nasopharyngeal measurement sites. The MAP remained stable over the two temperatures in both groups. A difference in MAP was seen between groups with MAP being greater at both temperatures in Group CP but there was no group x time interaction (p=0.0904). In both groups the CSFP increased with rewarming. The CPP was stable over time, within groups, with no group x time interaction (p=0.771).

The blood gas and blood $O_2$ content data are shown in Table 8 below. Both groups had similar hemoglobin concentrations during CPB and similar pH and PaCO$_2$. A significant group by time interaction was observed for SSS $O_2$ content (p=0.0005), SSS $O_2$ (p=0.003), and art-SSS $O_2$ content difference (p=0.011). In all instances Group CP remained more stable. In Group NP, there was a significant decrease in SSS $O_2$ content and SSS $O_2$ with rewarming, and an increase in the art-SSS $O_2$ content difference.

The regional CBF and CMRO$_2$ data are shown in Table 8. In both groups regional CBF increased with rewarming. There was no difference between groups for CBF in any region. Flow:metabolic coupling decreased with rewarming in Group NP. There was no difference in CMRO$_2$ between groups. In both groups CMRO$_2$ increased with rewarming.

Example 6

This Example discusses the results obtained in

Example 5.

Use of computer-controlled CPB roller pump according to the invention, which restores inherent biologic variability, as described in Examples 4 and 5, prevents cerebral deoxygenation during rewarming. The SSS $O_2$, SSS $O_2$ content, and the art-SSS $O_2$ content difference were all stable following rewarming in Group CP. In contrast, in Group NP, the SSS $O_2$ and SSS $O_2$ content decreased and the art-SSS $O_2$ content difference increased with rewarming suggesting cerebral deoxygenation with conventional non-pulsatile CPB (Table 8, FIG. 7). This experimental group had CPB managed similarly to that of patients in a study by Croughwell et al. (Ann. Thorac. Surg. 1994; 58:1702–1708) (α-stat acid-base management, use of arterial line filter and membrane oxygenator, and a similar duration of CPB). In all instances, the cerebral deoxygenation was not as severe as that seen by Croughwell et al. However, the changes seen were similar to those in the clinical scenario, and the more important observation is that computer-controlled CPB prevented these changes with rewarming.

The differences between the two groups does not appear to be a consequence of changes in CBF with computer-controlled CPB. It is of interest that the $O_2$ content difference was lower during hypothermia in Group NP than in Group CP and became greater with rewarming. This may suggest that there was a difference in distribution of CBF during CPB between the two groups given no difference in tCBF. If so, this finding could imply two flow pathways with CPB (a shunt and a parenchymal flow pathway). The use of computer-controlled CPB which restored inherent biologic rhythms would appear to provide better parenchymal flow, resulting in a greater oxygen content difference during the hypothermic bypass period and an ability for recruitment of the capillary bed in proportion to the requirements of increased metabolic demand with rewarming. With non-pulsatile bypass, the lower $O_2$ content difference at similar tCBF suggests a greater shunt flow, during the period of hypothermia. With rewarming, parenchymal blood flow appears inadequate to meet the increased metabolic demands of the tissue which results in increased extraction of oxygen and an increased $O_2$ content difference, lowered SSS $O_2$ and $O_2$ saturation. These results suggest that the greater deoxygenation seen with conventional CPB may be a consequence of capillary closure to parenchymal beds due to non-pulsatile bypass.

Non-pulsatile perfusion has been demonstrated to increase tissue water and alter vascular properties in other tissues such as the lung. These effects of the abnormal pulsation are unaltered by hypothermia, anesthesia or use of arterial filters. Hence these presumed neural protective interventions may not be helpful and may account for lack of clinical correlates of improved neurologic outcome with their institution. The improvements seen with computer-controlled pulsatile flow provides strong indirect evidence that the microembolic theory inadequately explains why the brain is damaged during CPB.

The better cerebral oxygenation occurring with computer-controlled CPB is not likely due to any change in the microembolic load presented to the brain. Pulsation, per se, should not alter the microembolic load, and the CBF was identical in the two groups, at both temperatures suggesting another mechanism independent of microemboli being the causative reason for the difference between groups. Microemboli are felt to be the leading candidates to explain the neurologic and neuropsychologic damage following CPB. The microemboli theory cannot effectively explain the reason for the increased $O_2$ extraction seen on rewarming. An explanation of parallel flow pathways during CPB (one shunt pathway and one parenchymal flow pathway) which is a consequence of the monotonous regular non-pulsatile blood flow with resultant cerebral capillary bed closure can explain why neural damage occurs despite strategies to decrease cerebral blood flow and thereby decrease the embolic load to the brain. Computer-controlled pulsation creates a more physiologic flow state with improved cerebral oxygenation following rewarming.

SUMMARY OF DISCLOSURE

In summary of this disclosure, the present invention provides computer control of the operation of a cardiopulmonary bypass pump, a lung ventilator or other device which provides simulation of in vivo variability of flow of a biologic fluid to an organ. Modifications are possible within the scope of this invention.

28

Table I
Program Listing for Blood Pump Control
{$A+,B-,D+,E+,F-,I+,L+,N+,O-,R+,S+,V+}
{$M 16384,0,655360}
{Program to control the RPM of a perfusion pump by a variation
derived from a file generated by Codas of a pressure recording -
before heart bypass has occurred.
Input file is format commented in LoadPeakRates.  The Peak
pressure and the heart rate period are the only columns used.
The minimum of the Peak pressure is removed from each observation
to generate a list of Peak Pressure variations from minimum to
maximum.
The Peak Pressure variations from 0 to max are scaled from 0 to
5 volts and sent out the D/A channel 0 output.  External scaling
is used to establish the RPM variation associated with 5 volts
output.
The period each pressure variation is held at the output is
related to the heart rate period.
The data is scanned forwards and then backwards continuously
until a key is struck.
}
Program Purfus;
Uses Crt, Dos;

Const
 MAXBUF = 8000; {maximum # of 3 sets of data points to be loaded}
Type
 datbuf = array[1..MAXBUF] of single;
 datdef = ^datbuf;
 statdef = array[1..3] of single;
Var
 peak, mean, period : datdef;
 peakstat, meanstat, periodstat : statdef; {stats of data loaded}
BaseAddr : word;

{Driver for Das16 D/A channel 0 = BaseAddr + 4, + 5}

SUBSTITUTE SHEET

```
Procedure D2A0Out( x : integer);
var
 LowByte, HighByte : integer;
begin
 LowByte : = (xAND $F) * 16;
 HighByte : =  xDIV 16;
 port[BaseAddr + 4] : = LowByte;
 port[BaseAddr + 5] : = HighByte; {output not upddated
                                   until High byte sent}
end; { D2A0Out }

Procedure GetHeap;

Procedure Bye;
begin
 writeln('Sorry, not enough memory available for heap!');
 halt(1);
end; { Bye } begin { GetHeap }
 if MaxAvail < SizeOf(datbuf) then Bye;
 GetMem(peak, SizeOf(datbuf));
 if MaxAvail < SizeOf(datbuf) then Bye;
 GetMem(mean, SizeOf(datbuf));
 if MaxAvail < SizeOf(datbuf) then Bye;
 GetMem(period, SizeOf(datbuf));
end; { GetHeap }

Procedure FreeHeap;
begin
 FreeMem(peak, SizeOf(datbuf));
 FreeMem(mean, SizeOf(datbuf));
 FreeMem(period, SizeOf(datbuf));
end; { FreeHeap }
Function FileExist(fn : string) : boolean;
var
```

SUBSTITUTE SHEET

```
 fp : text;
begin
 Assign(fp, fn);
 {$i} Reset(fp); {$i+}
 if IoResult <> 0 then
  FileExist : = false
 else
 begin
  Close(fp);
  FileExist : = true;
 end;
end; { FileExist }

Function init : boolean; {test input file & init D/A BaseAddr}
var
 P : PathStr;
 D : DirStr;
 N : NameStr;
 E : ExtStr;
 fp : Text;

begin
 if (ParamCount = 0) or (FileExist(ParamStr(1)) = false) then
 begin
  init : false;
  exit;
 end;

{ Load D/A Configuration file }
 P : = ParamStr(0); { full pathname to program running }
 FSplit(P, D, N, E);
 Assign(fp, D + N + '.cfg');
 {$i-} Reset(fp); {$i +}
 if IoResult < > 0 then {file missing, create a default one} begin
```

SUBSTITUTE SHEET

```
ReWrite(fp);
BaseAddr : = 784;
writeln(fp, BaseAddr); (* Al's machine D/A uses & H310 base
address *)
end
else
  readln(fp, BaseAddr);
close(fp);
D2A0Out(0);   { send a 0 to D/A to init }
 init : = true;
end; { init }
{              Sample File Format
"Data file: C:\CODAS\MUTCH3"
"Source channel: 6"
"Engineering units: mm Hg"
"Sample ra""te of cha""nnel:"  160
"Cycle type: Peak to Valley"
"Cycles pe""r average"": "1
"Valley"," Peak"," Mean"," Sec"," S/N Vly"," S/N Pk"
9.660E+01, 1.335E+02, 1.157E+02, 1.5625E-01, 5.500000E+01,
3.000000E+01
9.635E+01, 1.334E+02, 1.171E+02, 1.4375E-01, 1.160000E+02,
9.300000E+01
}

Procedure LoadPeakRates(fn : string; Var numgot : integer);
var
 fp : text;
 t : string;
 i : integer;
 valley : single;
Function GetReal : single; { Codas file contains[,] so string
bang it}
var
 ierr : integer;
 tmp : string;
```

```
x : single;
begin
 while t[1] = ' ' do Delete(t, 1, 1); {leading delete []'s}
 if t[Length(t)] < > ',' then t : = t + ','; {force[,] at end of
 str} tmp : = Copy(t, 1, Pos(',', t) - 1);
 Val(tmp, x, ierr);
 if ierr < > 0 then
 begin
 writeln('an error occurred converting [', tmp, ']');
 Close(fp);
 halt(1);
 end;

Delete(t, 1, Pos(',', t));  {remove value converted from str}
 GetReal : = x;
 end; { GetReal } begin { LoadPeakRates }
 Assign(fp, fn);
 {$i-} Reset(fp); {$i+}
 if IoResult < > 0 then halt(1);  { file existed previously} i : = 0;  { init line counter }
 numgot : = 0;

while (not Eof(fp)) and (numgot < MAXBUF) do
begin
 inc(i);
 readln(fp, t);

if i < 10 then     { list header while loading file }
begin
 while Pos('"', t) > 0 do  { delete ["]'s for easy reading }
  Delete(t, Pos('"', t), 1);
```

SUBSTITUTE SHEET

```
 writeln(t);
end
else
begin
 inc(numgot);
 if numgot < = 10 then writeln(t);  { list 1st 10 lines }
 valley : = GetReal;
 peak"[numgot] : = GetReal;
 mean"[numgot] : = GetReal;
 period"[numgot] : = GetReal;
{   writeln(valley:13:-4, peak"[numgot]:13:-4,
    mean"[numgot]:13:-4, period"[numgot]:13:-4);   } end;
end;   { while not eof }

Close(fp);

if numgot = MAXBUF then
  writeln('***data buffer only contains first ', MAXBUF,
    ' file entries ***');
end; { LoadPeakRates}

Function Min(x, y : single) : single;
begin
 if x < y then
  Min : = x
 else
  Min : = y;
end;   { Min }

Function Max(x, y : single) : single;
begin
 if x > y then
  Max : = x
 else
```

SUBSTITUTE SHEET

```
  Max : = y;
end;  { Max }

Procedure CalStat(Var col : datdef; Var stat : statdef;n :
integer);
{ Generaric calculate min, max, and avg of one column }
var
 i : integer;
begin
 stat[1] : = col^[1];   { init min }
 stat[2] : = col^[1];   { init max }
 stat[3] : = 0;         { init summation } for i : = 1 to n do
 begin
  stat[1] : = Min(stat[1], col^[i]);
  stat[2] : = Max(stat[2], col^[1]);
  stat[3] : = stat[3] + col^[1];
 end;
 stat[3] : = stat[3] / Int(n);
end;  { CalStat }

Procedure GetStats(n : integer); { cal min, max, & avg of data
loaded }
var
 i : integer;
begin
 if n < 2 then exit;  { nothing to do }
CalStat(peak, peakstat, n);
CalStat(mean, meanstat, n);
CalStat(period, periodstat, n);

{ report }
 writeln;
 writeln(' ':15, 'Peak':15, 'Mean':15, 'Period:15);
 writeln('Min':15, peakstat[1]:15:3, meanstat[1]:15:3,
```

```pascal
  periodstat[1]:15:3, periodstat[1]:15:5);
  writeln('Max':15, peakstat[2]:15:3, meanstat[2]:15:3,
  periodstat[2]:15:5);
  writeln('Avg':15, peakstat [3]:15:3, meanstat[3]:15:3,
  periodstat[3]:15:5);
  writeln;
end; { GetStats }

Procedure RemoveMinFromPeak(n : integer);
var
  i : integer;
begin
 for i : = 1 to n do
   peak^[i] : = peak^[i] - peakstat[1]; { remove min from peak
   column }
  peakstat[2] : = peakstat[2] - peakstat[1];
  peakstat[1] : = 0;
end: { RemoveMinFromPeak }

Procedure Pause(seconds : single);
Type
 timerec = record
         hr, min, sec, hund : word;
         end;
var
 tnow, tend : timerec;
 t1, t2 : longint;

Function Time2Long( time : timerec) : longint;
var
 t : longint;
 hr, min, sec, hund : longint;
begin
 hr : = time.hr;
 min : = time.min;
 sec : = time.sec;
```

SUBSTITUTE SHEET

```
 hund : = time.hund;
 t : = hund + sec * 100 + min * 100 * 60 + hr * 100 * 60 * 60;
 Time2Long : = t;
end;  { Time2Long } begin  { Pause }
 with tend do GetTime(hr, min, sec, hund); { Get Current Time }

{ add seconds passed in to tend to know stop time }
 with tend do
begin
 hund : = hund + Round(Frac(seconds) * 100.0);
 sec : = sec + Trunc(Int(seconds));

if hund > 99 then
begin
 hund : = hund - 100;
 sec : = sec + 1;
end;

while sec > 59 do
begin
 sec : = 60;
 min : = min + 1;
end;

while min > 59 do
begin
 min : = - 60;
 hr : = hr + 1;
end;

while hr > 23 do
 hr : = hr - 24;

end;  { with tend }
```

SUBSTITUTE SHEET

```
t2 : = Time2Long(tend);

repeat
 with tnow do GetTime(hr, min, sec, hund);  {Get Time now } tnow
 t1 : = Time2Long(tnow);
until t1 > = t2;
end;  ( Pause )

Procedure ListWithPause(n : integer);
var
 i, d2a : integer;
begin
 for i : = 1 to n do
begin
 d2a : = Round(peak^[i] / peakstat[2] * 4095.0);
 writeln(i:5, peak^[i]:10:1, period^[i]:10:4, d2a:10);
 Pause(period^[i]);
end;  ( for i : = )
end;  ( ListWithPause )

Procedure SendToD2A(n : integer);
var
 i, d2a : integer;
 up, done, first : boolean;
 ch : char;

begin
 done : = false;
 first : = true; ( flag for 1st pass )
 up : = true  ( scan data upwwards first )
 i : =    ( data pointer )

while Not Done do
begin
 if (up) and (i = n) then up : = false;  ( Up or Down )
 if (Not up) and (i = 1) then up : = true;
```

SUBSTITUTE SHEET

```
 if first then  { 1st pass only }
   first : = false else   { normal data pointer incr/dec }
begin
 if up then
   Inc(i)
else
   Dec(i);
end;

d2a : = Round(peak^[i] / peakstat[2] * 4095.0);
D2A0Out(d2a);
Pause(period^[i]);

if Key Pressed then
begin
   ch : = ReadKey;
   if ch = Chr(27) then done : = true;
 end;
end;   { while not Done }
end;   { SendToD2A } var
 n : integer;
 ch : char;

begin  { Main }
 if not init then
 begin
 writeln('Purfus filename.exc');
 halt(1);
end;

ClrScr;
 GetHeap;
```

SUBSTITUTE SHEET

```
TextBackGround(1);
TextColor(7);

writeln('loading ', ParamStr(1));
LoadPeakRates(ParamStr(1), n);
writeln('Loaded ',n, ' data points');
GetStats(n);
RemoveMinFromPeak(n);   { remove min value from Peak column }
GetStats(n);

writeln('Press any key to continue');
ch : = ReadKey;

ClrScr;
writeln('**** Calibration ****');
writeln;
writeln('Set the Pump Rate to desired Blood Pressure');
writeln('Press any key to continue');
ch : = ReadKey;
writeln;

writeln('Adjust the Variability Level Control to 0 (CCW) Now!');
writeln('Press any key to continue');
ch : = ReadKey;
writeln;

writeln('Set the Variability Level Control to desired MAX Peak
Blood Pressure');
D2AOOut(4095);   { set D/A output to 5 volts }
writeln('Press any key to continue');
ch : = ReadKey;
D2AOOut(O);   { set D/A output to 0 volts }
writeln;

writeln('About to start Pump Control Loop');
writeln('Press any key to continue');
```

```
ch : = ReadKey;
writeln;
writeln('Press ESC to terminate Control of Pump Rate');

{ ListWithPause(n); }
  SendToD2A(n);

D2A0Out(O);  { reset D/A to 0 on exit }
  FreeHeap;
  TextBackGround(O);
  TextColor(7);
end.
```

SUBSTITUTE SHEET

Vent.Bas - Main of Ventilator Control                              21 Nov 93
                                                                  14:48:59
                    Microsoft (R) QuickBASIC Compiler Version 4.50
```
'$Title:'Vent.Bas - Main of Ventilator Control' $LineSize:112'
'Vent.Bas
'Chris McLennan
'Oct 11/93

'MenuSys.Bas
DECLARE SUB GetConfig ()
DECLARE SUB Init ()
DECLARE SUB MainMenu ()
DECLARE SUB SetConfig (Mode AS INTEGER)
DECLARE SUB TestGrModes ()
'DasLib.Bas
DECLARE SUB InitDas16 ()
'VentLib.Bas
DECLARE SUB InitVentLib ()

'$INCLUDE: 'DasLib.Bil'
'---------- DasLib.Bil ----------
'Das16 Common Area
  'Das16 Parameters MUST be in common
  CONST A2dBuffSize = 2000
  DIM Dio(4) AS INTEGER
  DIM A2dBuff(2000) AS INTEGER
  DIM A2dChNum(2000) AS INTEGER COMMON Dio() AS INTEGER, Md AS INTEGER, Flag AS INTEGER
  COMMON BiPolar AS INTEGER, DasChan AS INTEGER, VoltFS AS SINGLE
  COMMON A2dBuff() AS INTEGER          'Buffer for DasMode4
  COMMON A2dChNum() AS INTEGER         'Buffer for A/D channel info
  'for Mode 5 & 6, Quick Basic manages the Data Segment
  '$DYNAMIC
  'Dynamic Common is dimensioned AFTER the COMMON specification
  CONST A2dBuf2Size = 2000
```

SUBSTITUTE SHEET

Vent.Bas - Main of Ventilator Control

```
  COMMON A2dBuf2() AS INTEGER        'Buffer for A/D data
  '$STATIC
'---------- End DasLib.Bil ----------
  '$INCLUDE: 'MenuSys.Bil'
'---------- MenuSys.Bil----------
  ' Constants for best available screen mode
  CONST VGA = 12
  CONST MCGA = 13
  CONST EGA256 = 9
  CONST EGA64 = 8
  CONST MONO = 10
  CONST HERC = 3
  CONST CGA = 1
  ' User-defined type to hold information about the mode
  TYPE Config
      Scrn     AS INTEGER
      Colors   AS INTEGER
      Atribs   AS INTEGER
      XPix     AS INTEGER
      YPix     AS INTEGER
      TCOL     AS INTEGER
      TROW     AS INTEGER
  END TYPE
  '*****Graphics Modes
  COMMON VC AS Config, InitRows AS INTEGER, BestMode AS INTEGER,
Available AS STRING
  '****Menu system
  '$DYNAMIC
  COMMON PopBuf() AS INTEGER, CurPath$, ForGnd AS INTEGER, Bakgnd
AS INTEGER
  '$STATIC
'---------- End MenuSys.Bil----------
  '$INCLUDE: 'VentLib.Bil'
'---------- VentLib.Bil ----------
'VentLib Dynamic Common declaration
```

SUBSTITUTE SHEET

Vent.Bas - Main of Ventilator Control

```
  TYPE VentDat                  'Structure to hold modulation data
     Time AS SINGLE
     Mode AS STRING * 1
     Modulation AS SINGLE
  END TYPE
  CONST VentArrSize = 2000
  COMMON VentArrNum AS INTEGER         '# of items loaded in
VentArr()
  COMMON VentDatFn$                     'Data File loaded
  '$DYNAMIC
  'Dynamic Common is dimensioned AFTER the COMMON specification
  COMMON VentArr() AS VentDat          'Buffer for Ventilator
modulation data
  '$STATIC
'---------- End VentLib.Bi1 ----------
  '$INCLUDE: 'DasLib.Bi2'
'---------- DasLib.Bi2 ----------
  DIM A2dBuf2(A2dBuf2Size) AS INTEGER
'---------- End DasLib.Bi2 ----------
  '$INCLUDE: 'MenuSys.Bi2'
'---------- MenuSys.Bi2----------
  DIM PopBuf(2002, 1) AS INTEGER   'PopUp Buffer
'---------- End MenuSys.Bi2----------
  '$INCLUDE: 'VentLib.Bi2'
'---------- VentLib.Bi2 ----------
  DIM VentArr(VentArrSize) AS VentDat  'Buffer for Ventilator
modulation data
'---------- End VentLib.Bi2 ----------
  InitDas16                             'General Reset of Das16
  InitVentLib                           'Clear Commons
  'Determine Graphic Card
  GetConfig
  VC.Scrn = BestMode
  SetConfig VC.Scrn         'loads record VC with graphic mode
parameters
```

SUBSTITUTE SHEET

44

Vent.Bas - Main of Ventilator Control

' TestGrModes

Init
  MainMenu
  COLOR 7, 0
  END

43933 Bytes Available
41609 Bytes Free

0 Warning Error(s)
     0 Severe  Error(s)

DasLib.Bas - Das16 Library

```
    '$Title:'DasLib.Bas - Das16 Library'  $LineSize:112'
    'DasLib
    'Das16 Library Interface
    'Oct 2/93
    'Chris McLennan
    'MenuSys.Bas
    DECLARE FUNCTION Exist! (FileName$)
    DECLARE SUB DAS16 (MODE%, BYVAL dummy%, Flag%)
    DECLARE SUB DasMode0 ()
    DECLARE SUB DasMode1 (ChLow AS INTEGER, ChHigh AS INTEGER)
    DECLARE SUB DasMode2 (NextCh AS INTEGER, ChLow AS INTEGER,
ChHigh AS INTEGER)
    DECLARE SUB DasMode3 (A2dData AS INTEGER, A2dCh AS INTEGER)
    DECLARE SUB DasMode4 (NumPts AS INTEGER)
    DECLARE SUB DasMode5 (NumPts AS INTEGER, Cycle AS INTEGER)
    DECLARE SUB DasMode6 (NumPts AS INTEGER, Cycle AS INTEGER)
    DECLARE SUB DasMode7 ()
    DECLARE SUB DasMode8 (Op AS INTEGER, Status AS INTEGER, Count
AS INTEGER)
    DECLARE SUB DasMode9 (NumPts AS INTEGER, StartPt AS INTEGER)
    DECLARE SUB DasMode15 (D2aCh AS INTEGER, D2aData AS INTEGER)
    DECLARE SUB DasMode16 (D2aDat0 AS INTEGER, D2aDat1 AS INTEGER)
    DECLARE SUB DasMode17 (Rate!)
    DECLARE SUB DasError (code AS INTEGER)
    DECLARE FUNCTION A2dToVolt! (A2dVal AS INTEGER)
    DECLARE FUNCTION IntToReal! (x AS INTEGER)
    DECLARE FUNCTION RealToInt% (x!)
    DECLARE FUNCTION VoltToD2a% (volt!)
    '$INCLUDE: 'DasLib.Bil'
'---------- DasLib.Bil ----------
'Das16 Common Area
    'Das16 Parameters MUST be in common
    CONST A2dBuffSize = 2000
    DIM Dio(4) AS INTEGER
    DIM A2dBuff(2000) AS INTEGER
```

SUBSTITUTE SHEET

DasLib.Bas - Das16 Library

```
  DIM A2dChNum(2000) AS INTEGER

COMMON Dio() AS INTEGER, Md AS INTEGER, Flag AS INTEGER
  COMMON BiPolar AS INTEGER, DasChan AS INTEGER, VoltFS AS SINGLE
  COMMON A2dBuff() AS INTEGER          'Buffer for DasMode4
  COMMON A2dChNum() AS INTEGER         'Buffer for A/D channel
info
  'for Mode 5 & 6, Quick Basic manages the Data Segment
  '$DYNAMIC
  'Dynamic Common is dimensioned AFTER the COMMON specification
  CONST A2dBuf2Size = 2000
  COMMON A2dBuf2() AS INTEGER          'Buffer for A/D data
  '$STATIC
'---------- End DasLib.Bi1 ----------
  '$INCLUDE: 'DasLib.Bi2'
'---------- DasLib.Bi2 ----------
  DIM A2dBuf2(A2dBuf2Size) AS INTEGER
'---------- End DasLib.Bi2 ----------
'$Page  $SubTitle:'FUNCTION A2dToVolt'
```

DasLib.Bas - Das16 Library
FUNCTION A2dToVolt

FUNCTION A2dToVolt (A2dVal AS INTEGER)

'Returns A2d value converted into voltage

SHARED BiPolar AS INTEGER, VoltFS AS SINGLE

IF BiPolar THEN
        A2dToVolt = A2dVal / 2048! * VoltFS
    ELSE
        A2dToVolt = A2dVal / 4096! * VoltFS
    END IF

END FUNCTION

'$Page  $SubTitle:'SUB DasError'

SUBSTITUTE SHEET

DasLib.Bas - Das16 Library
SUB DasError

SUB DasError (code AS INTEGER)

SELECT CASE code
      CASE 0
         PRINT "OK"
      CASE 1
         PRINT "Driver not initialized"
      CASE 2
         PRINT "Mode number out of range"
      CASE 3
         PRINT "Base Address out of range"
      CASE 4
         PRINT "Interrupt Level out of range"
      CASE 5
         PRINT "DMA Level out of range"
      CASE 6
         PRINT "Differential Mux scan limits out of range"
      CASE 7
         PRINT "Single Ended Mux scan limits out of range"
      CASE 8
         PRINT "Error Code 8?"
      CASE 9
         PRINT "A/D Timeout Error - hardware - no EOC"
      CASE 10
         PRINT "Counter division ratio 0 or 1 in mode 17"
      CASE 11
         PRINT "Number of conversions <= 0 in modes 4,5, or 6"
      CASE 12
         PRINT "Counter configuration # out of range in mode 10"
      CASE 13
         PRINT "Digital output data out of range in mode 13"
      CASE 14
         PRINT "D/A data out of range in modes 15 or 16"

SUBSTITUTE SHEET

DasLib.Bas - Das16 Library
SUB DasError

```
    CASE 15
      PRINT "D/A channel # out of range"
    CASE 16
      PRINT "Counter read operation not 0 or 1 in mode 12"
    CASE 17
      PRINT "Start conversion negative # in mode 9"
    CASE 18
      PRINT "Word count 0 or negative in mode 9"
    CASE 19
      PRINT "Trigger mode not 0 or 1 in modes 4,5, or 6"
    CASE 20
      PRINT "DMA / Interrupt operation already active in modes
5 or 6"
    CASE 21
      PRINT "DMA page wrap around in mode 6"
    CASE 22
      PRINT "Hardware  failure  or  installation  error  [Base
Address?]"
    CASE 23
      PRINT "Trigger channel inconsistent with configuration
[mode 19]"
    CASE 24
      PRINT "Trigger data out of range [mode 19]"
    CASE 25

PRINT "Slope data not 0 or 1 [mode 19]"
  END SELECT

END SUB

'$Page  $SubTitle:'SUB DasMode0'
```

SUBSTITUTE SHEET

```
DasLib.Bas - Das16 Library
SUB DasMode0

SUB DasMode0
  'INIT DAS16 DRIVER
  'Use NEW format file Das16Adr.Cfg for Card initialization
  SHARED Dio() AS INTEGER, Md AS INTEGER, Flag AS INTEGER
  SHARED BiPolar AS INTEGER, DasChan AS INTEGER, VoltFS AS SINGLE
  DIM fp AS INTEGER, Status AS INTEGER
  IF NOT Exist("Das16Adr.Cfg") THEN
     CLS
     PRINT "Das16 Configuration file [Das16Adr.Cfg] not found"
     END
  END IF
  OPEN "Das16Adr.Cfg" FOR INPUT AS #1
  INPUT #1, Dio(0)              'get base I/O address
  INPUT #1, Dio(1)              'interrupt level
  INPUT #1, Dio(2)              'D.M.A. level
  INPUT #1, VoltFS              'Voltage Range
  CLOSE #1
  Flag = 0                      'error variable
  Md = 0                        'mode 0 - initialize
  CALL DAS16(Md, VARPTR(Dio(0)), Flag)
  IF Flag <> 0 THEN
     DasError (Flag)
     END
  END IF
  '---- Find DASH-16 operating configurations ----
  'read status register at base address + 8
  Status = INP(Dio(0) + 8)
  IF (Status AND &H40) = &H40 THEN       ' BIPOLAR OR UNIPOLAR
     BiPolar = 0
  ELSE
     BiPolar = -1
  END IF
  IF (Status AND &H20) = &H20 THEN
     DasChan = 16
```

51

```
DasLib.Bas - Das16 Library
SUB DasMode0

ELSE
    DasChan = 8          ' # CHANNELS
  END IF

END SUB

'$Page   $SubTitle:'SUB DasMode1'
```

52

```
DasLib.Bas - Das16 Library
SUB DasMode1

SUB DasMode1 (ChLow AS INTEGER, ChHigh AS INTEGER)

'SET MULTIPLEXER SCAN LIMITS

SHARED Dio() AS INTEGER, Md AS INTEGER, Flag AS INTEGER

IF ChLow > ChHigh THEN SWAP ChLow, ChHigh

Dio(0) = ChLow     'LOW LIMIT
  Dio(1) = ChHigh    'HIGH LIMIT
  Md = 1
  CALL DAS16(Md, VARPTR(Dio(0)), Flag)

IF Flag <> 0 THEN
    DasError (Flag)
    END
  END IF

END SUB

'.$Page  $SubTitle:'SUB DasMode15'
```

SUBSTITUTE SHEET

```
DasLib.Bas - Das16 Library
SUB DasMode15

SUB DasMode15 (D2aCh AS INTEGER, D2aData AS INTEGER)

'Output Data to one D/A Channel

'If the -5vRev is connected to the D/A Ref In on the DB 37,
  'an output from 0 to 5V is generated.

SHARED Dio() AS INTEGER, Md AS INTEGER, Flag AS INTEGER

Dio(0) = D2aCh      'Channel #[0..1] to send to
  Dio(1) = D2aData    'Data to send [0..4095]
  Md = 15
  CALL DAS16(Md, VARPTR(Dio(0)), Flag)
  IF Flag <> 0 THEN
    DasError (Flag)
    END
  END IF

END SUB

'$Page  $SubTitle:'SUB DasMode16'
```

54

```
DasLib.Bas - Das16 Library
SUB DasMode16

SUB DasMode16 (D2aDat0 AS INTEGER, D2aDat1 AS INTEGER)

'Output Data to both D/A Channels

'If the -5vRev is connected to the D/A Ref In on the DB 37,
  'an output from 0 to 5V is generated.

SHARED Dio() AS INTEGER, Md AS INTEGER, Flag AS INTEGER

Dio(0) = D2aDat0   'Channel 0
  Dio(1) = D2aDat1   'Channel 1
  Md = 16
  CALL DAS16(Md, VARPTR(Dio(0)), Flag)
  IF Flag <> 0 THEN
    DasError (Flag)
    END
  END IF

END SUB

'$Page  $SubTitle:'SUB DasMode17'
```

SUBSTITUTE SHEET

DasLib.Bas - Das16 Library
SUB DasMode17

SUB DasMode17 (Rate)

```
'COMPUTE SCAN RATE PER CHANNEL FOR A/D
'
' HZ = 1,000,000 / ( N1 * N2 )
'
'    WHERE  2 < N1 & N2 > 65535
'
SHARED Dio() AS INTEGER, Md AS INTEGER, Flag AS INTEGER
DIM NextCh AS INTEGER, ChLow AS INTEGER, ChHigh AS INTEGER
DIM Sr, HzMin, HzMax, Prod, Seed1, Seed2, NumCh AS INTEGER
'DETERMINE # CHANNELS IN USE
NextCh = 0
ChLow = 0
ChHigh = 0
CALL DasMode2(NextCh, ChLow, ChHigh)
NumCh = ChHigh - ChLow + 1      ' NUMCH
'CAL SCAN RATE PER CHANNEL
Sr = Rate * NumCh
'FIX RATE OVERFLOWS
HzMax = 1000000! / 4
HzMin = 1000000! / (65535! * 65535!)
IF Sr > HzMax THEN Sr = HzMax
IF Sr < HzMin THEN Sr = HzMin
'TRICKY ROUTINE
'
Prod = 1000000! / Sr          'PROD = N1 * N2
Seed1 = 2                     'STARTING VALUE OF SEED1
DO
   IF Prod / Seed1 <= 65535 THEN EXIT DO      'SEED2 WILL BE VALID
   Seed1 = INT(Seed1 * 2)                     'DOUBLE NEXT GUESS FOR SEED1
```

```
DasLib.Bas - Das16 Library
SUB DasMode17

IF Seed1 > 65535 THEN Seed1 = 65535          '& TEST FOR
OVERFLOW
  LOOP
  Seed2 = INT(Prod / Seed1)

'CALL DASH16
  Md = 17

Dio(0) = RealToInt(Seed1)
  Dio(1) = RealToInt(Seed2)

'PRINT Dio(0), Dio(1), 1000000 / (Seed1 * Seed2)

CALL DAS16(Md, VARPTR(Dio(0)), Flag)
  IF Flag <> 0 THEN
    DasError (Flag)

END
  END IF
END SUB

'$Page  $SubTitle:'SUB DasMode2'
```

```
DasLib.Bas - Das16 Library
SUB DasMode2

SUB DasMode2 (NextCh AS INTEGER, ChLow AS INTEGER, ChHigh AS
INTEGER)
  'READ CURRENT MULTIPLEXER ADDRESS AND SCAN LIMITS SHARED Dio() AS INTEGER, Md AS INTEGER, Flag AS INTEGER Md = 2
  CALL DAS16(Md, VARPTR(Dio(0)), Flag)
  IF Flag <> 0 THEN
    DasError (Flag)
    END
  END IF NextCh = Dio(0)    'NEXT CHANNEL TO CONVERT
  ChLow = Dio(1)     'LOWER SCAN LIMIT
  ChHigh = Dio(2)    'UPPER SCAN LIMIT
END SUB '$Page  $SubTitle:'SUB DasMode3'
```

```
DasLib.Bas - Das16 Library
SUB DasMode3

SUB DasMode3 (A2dData AS INTEGER, A2dCh AS INTEGER)

'Do one A/D conversion and increment Mux

SHARED Dio() AS INTEGER, Md AS INTEGER, Flag AS INTEGER

Md = 3
  CALL DAS16(Md, VARPTR(Dio(0)), Flag)
  IF Flag <> 0 THEN
    DasError (Flag)
    END
  END IF A2dData = Dio(0)   'A/D data
  A2dCh = Dio(1)     'A/D Channel
END SUB '$Page  $SubTitle:'SUB DasMode4'
```

SUBSTITUTE SHEET

DasLib.Bas - Das16 Library
SUB DasMode4

SUB DasMode4 (NumPts AS INTEGER)

'Do NumPts A/D conversions directly to array A2dBuff()

SHARED Dio() AS INTEGER, Md AS INTEGER, Flag AS INTEGER
  SHARED A2dBuff() AS INTEGER IF NumPts > A2dBuffSize THEN NumPts = A2dBuffSize Dio(0) = NumPts              '# pts to convert
  Dio(1) = VARPTR(A2dBuff(0))  'output array location
  Dio(2) = 1                   'trigger source, 1=timer,
0=external on IP0
  'Note: If the timer is used as a trigger source then holding
input IP0
  '      low will delay starting conversions.
  Md = 4
  CALL DAS16(Md, VARPTR(Dio(0)), Flag)
  IF Flag <> 0 THEN
    DasError (Flag)
    END
  END IF
END SUB '$Page  $SubTitle:'SUB DasMode5'
```

SUBSTITUTE SHEET

DasLib.Bas - Das16 Library
SUB DasMode5

SUB DasMode5 (NumPts AS INTEGER, Cycle AS INTEGER)

'Do NumPts A/D conversions and transfer to memory on INTERRUPT
  'This uses Dynamically allocated A2dBuf2 in common data segment
  'This runs in the background
  'Data is accessed by DasMode9
  'Cycle = 0 for One Scan and finish
  '       = 1 for Continuous Scanning --> DasMode7 to stop SHARED Dio() AS INTEGER, Md AS INTEGER, Flag AS INTEGER
  SHARED A2dBuf2() AS INTEGER IF NumPts > A2dBuf2Size THEN NumPts = A2dBuf2Size Dio(0) = NumPts              '# pts to convert
  Dio(1) = VARSEG(A2dBuf2(0))  'output array location
  Dio(2) = 1                              'trigger source, 1=timer,
0=external on IP0
  'Note: If the timer is used as a trigger source then holding
input IP0
  '      low will delay starting conversions.
  Dio(3) = Cycle               '0 = One shot and finish
                               '1 = Continuous Scanning - Mode7
to stop
  Md = 5
  CALL DAS16(Md, VARPTR(Dio(0)), Flag)
  IF Flag <> 0 THEN
    DasError (Flag)
    DasMode7
    END
  END IF
END SUB '$Page  $SubTitle:'SUB DasMode6'

DasLib.Bas - Das16 Library
SUB DasMode6

```
SUB DasMode6 (NumPts AS INTEGER, Cycle AS INTEGER)

'Do NumPts A/D conversions and transfer to memory via DMA
  'This uses Dynamically allocated A2dBuf2 in common data segment
  'This runs in the background
  'Data is accessed by DasMode9
  'Cycle = 0 for One Scan and finish
  '       = 1 for Continuous Scanning --> DasMode7 to stop
  SHARED Dio() AS INTEGER, Md AS INTEGER, Flag AS INTEGER
  SHARED A2dBuf2() AS INTEGER IF NumPts > A2dBuf2Size THEN NumPts = A2dBuf2Size Dio(0) = NumPts              '# pts to convert
  Dio(1) = VARSEG(A2dBuf2(0))  'output array location
  Dio(2) = 1                   'trigger source, 1=timer,
0=external on IP0
  'Note: If the timer is used as a trigger source then holding
input IP0
  '      low will delay starting conversions.
  Dio(3) = Cycle               '0 = One shot and finish
                               '1 = Continuous Scanning - Mode7
to stop
  Md = 6
  CALL DAS16(Md, VARPTR(Dio(0)), Flag)
  IF Flag <> 0 THEN
    DasError (Flag)
    DasMode7
    END
  END IF
END SUB '$Page  $SubTitle:'SUB DasMode7'
```

```
DasLib.Bas - Das16 Library
SUB DasMode7

SUB DasMode7
  'DISABLE DMA/INTERRUPT OPERATION OF A/D

SHARED Dio() AS INTEGER, Md AS INTEGER, Flag AS INTEGER

Md = 7
  CALL DAS16(Md, VARPTR(Dio(0)), Flag)
  IF Flag <> 0 THEN
    DasError (Flag)
    END
  END IF

END SUB

'$Page  $SubTitle:'SUB DasMode8'
```

DasLib.Bas - Das16 Library
SUB DasMode8

SUB DasMode8 (Op AS INTEGER, Status AS INTEGER, Count AS INTEGER)

'allows monitor of mode 5,6,18, or 20 Background operation

'Op = 0 none
   '    = 1 Mode 6 [DMA]
   '    = 2 Mode 5 [Interrupt]
   '    = 3 Mode 18 [Interrupt]
   '    = 4 Mode 20 [Interrupt]

'Status = 0 if Done or 1 in Active

'Count = Current word count [# conversions so far]
   '       = 0 to (Num Chan * pts per chan) - 1
   ' ex   = 4 channels @ 200 pts per channel = [0..799]
   '       = seems to indicate the current conversion - which is
not yet done.

SHARED Dio() AS INTEGER, Md AS INTEGER, Flag AS INTEGER

Md = 8
   CALL DAS16(Md, VARPTR(Dio(0)), Flag)
   IF Flag <> 0 THEN
     DasError (Flag)
     END
   END IF Op = Dio(0)          'Operation type
   Status = Dio(1)      'Status of Operation
   Count = Dio(2)       'Current word count

END SUB

'$Page  $SubTitle:'SUB DasMode9'

SUBSTITUTE SHEET

DasLib.Bas - Das16 Library
SUB DasMode9

SUB DasMode9 (NumPts AS INTEGER, StartPt AS INTEGER)

'Transfer Data from A2dBuf2() to A2dBuff() [from memory to array]
  'Channel information transfered into A2dChNum()
  'StartPt is starting conversion # - usually zero SHARED Dio() AS INTEGER, Md AS INTEGER, Flag AS INTEGER
  SHARED A2dBuf2() AS INTEGER          'input area
  SHARED A2dBuff() AS INTEGER          'output area for data
  SHARED A2dChNum() AS INTEGER         'output area for channel #'s IF NumPts > A2dBuf2Size THEN NumPts = A2dBuf2Size Dio(0) = NumPts                      '# pts to convert
  Dio(1) = VARSEG(A2dBuf2(0))          'input array location
  Dio(2) = StartPt                     'start transferring at conversion StartPt
  Dio(3) = VARPTR(A2dBuff(StartPt))    'Destination of Data to transfer
  Dio(4) = VARPTR(A2dChNum(StartPt))   'Destination of chan # Data to transfer
  Md = 9
  CALL DAS16(Md, VARPTR(Dio(0)), Flag)
  IF Flag <> 0 THEN
    DasError (Flag)
    DasMode7
    END
  END IF
END SUB '$Page  $SubTitle:'FUNCTION IntToReal'

SUBSTITUTE SHEET

65

```
DasLib.Bas - Das16 Library
FUNCTION IntToReal

FUNCTION IntToReal (x AS INTEGER)

'CONVERT SIGNED INTEGER TO REAL   [-32768 <==> 32767]

IF x >= 0 THEN
     IntToReal = x
   ELSE
     IntToReal = x + 65536
   END IF

END FUNCTION

'$Page  $SubTitle:'FUNCTION RealToInt%'
```

SUBSTITUTE SHEET

```
DasLib.Bas - Das16 Library
FUNCTION RealToInt%

FUNCTION RealToInt% (x)
  'CONVERT REAL TO SIGNED INTEGER   [-32768 <==> 32767]

IF x <= 32767 THEN
    RealToInt% = x
  ELSE
    RealToInt% = x - 65536
  END IF
END FUNCTION '$Page  $SubTitle:'FUNCTION VoltToD2a%'
```

```
DasLib.Bas - Das16 Library
FUNCTION VoltToD2a%

FUNCTION VoltToD2a% (volt)

'Calculates D/A value from a voltage from 0 to 5V
  'Assumes Das16 5V Reference in use
  'Returns integer between 0 & 4095

DIM x x = volt / 5! * 4096!

IF x < 0 THEN x = 0
  IF x > 4095 THEN x = 4095
  VoltToD2a% = CINT(x)

END FUNCTION

43949 Bytes Available
37723 Bytes Free

0 Warning Error(s)
     0 Severe  Error(s)
```

SUBSTITUTE SHEET

MenuSys.Bas - QBasic PopDown Menu System

```
'$Title:'MenuSys.Bas    -    QBasic    PopDown    Menu    System'
$LineSize:112'

' MenuSys.Bas
'
' Skeleton for PopDown Menu System for QBasic
' Video Mode is detected ' Chris McLennan Mar 28/93

'******User Interface
   DECLARE FUNCTION CenterStr$ (s$, length AS INTEGER)
   DECLARE FUNCTION Exist! (FileName$)
   DECLARE FUNCTION FUse$ (x AS SINGLE, wide AS INTEGER, dec AS
INTEGER)
   DECLARE FUNCTION LPad$ (s$, length AS INTEGER)
   DECLARE FUNCTION Max (x AS SINGLE, y AS SINGLE)
   DECLARE FUNCTION Min (x AS SINGLE, y AS SINGLE)
   DECLARE FUNCTION RPad$ (s$, length AS INTEGER)
   DECLARE FUNCTION StrTok$ (Srce$, Delim$)
   DECLARE SUB AboutBox ()
   DECLARE SUB BoxIt (x1 AS INTEGER, y1 AS INTEGER, x2 AS INTEGER,
y2 AS INTEGER)
   DECLARE SUB BrList (txt$(), NumLin AS INTEGER)
   DECLARE SUB Init ()
   DECLARE SUB MainMenu ()
   DECLARE SUB MenuBar (Item$(), NumLin AS INTEGER, Choice AS
INTEGER, Ky$, x AS INTEGER, Redraw
 AS INTEGER)
   DECLARE SUB MenuExec (cmd AS INTEGER, Done AS INTEGER, RtnCode
AS INTEGER)
   DECLARE SUB MsgBox (txt$(), NumLin AS INTEGER, Ky$, RestoreScrn
AS INTEGER, Pause AS INTEGER)
   DECLARE SUB Pop (x1 AS INTEGER, y1 AS INTEGER, x2 AS INTEGER,
y2 AS INTEGER)
```

SUBSTITUTE SHEET

MenuSys.Bas - QBasic PopDown Menu System

```
  DECLARE SUB PopUpList (Item$(), NumLin AS INTEGER, Choice AS
INTEGER, Ky$, SaveScrn AS INTEGE
R, Center AS INTEGER)
  DECLARE SUB SelectFile (FileName$)
  DECLARE SUB SelectNewPath ()
  DECLARE SUB UnPop ()
  'Graphic Mode Detection
  DECLARE SUB GetConfig ()
  DECLARE SUB SetConfig (mode AS INTEGER)
  DECLARE SUB TestGrModes ()

'VentLib.Bas
  DECLARE SUB BrPrnData ()
  DECLARE SUB Demo ()
  DECLARE SUB LoadVentDatPrn ()
  DECLARE SUB InitDas16 ()
  DECLARE SUB LoopTest ()
  DECLARE SUB LoopTest5 ()
  DECLARE SUB LoopTest6 ()
  DECLARE SUB OhioFn ()
  DECLARE SUB PlotVentDat ()
  DECLARE SUB VentLoop ()

'$INCLUDE: 'DasLib.Bil'
'---------- DasLib.Bil ----------

'Das16 Common Area
  'Das16 Parameters MUST be in common

CONST A2dBuffSize = 2000

DIM Dio(4) AS INTEGER
  DIM A2dBuff(2000) AS INTEGER
  DIM A2dChNum(2000) AS INTEGER
```

SUBSTITUTE SHEET

MenuSys.Bas - QBasic PopDown Menu System

```
  COMMON Dio() AS INTEGER, Md AS INTEGER, Flag AS INTEGER
  COMMON BiPolar AS INTEGER, DasChan AS INTEGER, VoltFS AS SINGLE
  COMMON A2dBuff() AS INTEGER            'Buffer for DasMode4
  COMMON A2dChNum() AS INTEGER           'Buffer for A/D channel
info 'for Mode 5 & 6, Quick Basic manages the Data Segment '$DYNAMIC
  'Dynamic Common is dimensioned AFTER the COMMON specification CONST A2dBuf2Size = 2000
  COMMON A2dBuf2() AS INTEGER       'Buffer for A/D data

'$STATIC

'---------- End DasLib.Bil ----------

'$INCLUDE: 'MenuSys.Bil'
'---------- MenuSys.Bil----------

' Constants for best available screen mode
  CONST VGA = 12
  CONST MCGA = 13
  CONST EGA256 = 9
  CONST EGA64 = 8
  CONST MONO = 10
  CONST HERC = 3
  CONST CGA = 1

' User-defined type to hold information about the mode
  TYPE Config
     Scrn    AS INTEGER
     Colors  AS INTEGER
     Atribs  AS INTEGER
```

SUBSTITUTE SHEET

MenuSys.Bas - QBasic PopDown Menu System

```
    XPix    AS INTEGER
    YPix    AS INTEGER
    TCOL    AS INTEGER
    TROW    AS INTEGER
 END TYPE

'*****Graphics Modes
  COMMON VC AS Config, InitRows AS INTEGER, BestMode AS INTEGER,
Available AS STRING
  '****Menu system
  '$DYNAMIC
  COMMON PopBuf() AS INTEGER, CurPath$, ForGnd AS INTEGER, Bakgnd
AS INTEGER
  '$STATIC '---------- End MenuSys.Bi1-----------

'$INCLUDE: 'DasLib.Bi21'
'---------- DasLib.Bi2 ----------
  DIM A2dBuf2(A2dBuf2Size) AS INTEGER
'---------- End DasLib.Bi2 ----------

'$INCLUDE: 'MenuSys.Bi2'
'---------- MenuSys.Bi2-----------
  DIM PopBuf(2002, 1) AS INTEGER   'PopUp Buffer
'---------- End MenuSys.Bi2-----------

CONST PgmVersion = 1.09

' Menu Data

MainMenuData:
  DATA "File"
  DATA "Demos"
  DATA ""
```

SUBSTITUTE SHEET

72

MenuSys.Bas - QBasic PopDown Menu System

```
PullDownMenuData:
   DATA "About",         1003
   DATA "Select path..", 1002
   DATA "Open..",        1004
   DATA "Import PRN..",  1010
   DATA "Browse Data",   1011
   DATA "Plot Data",     1012
   DATA "Dos Shell",     1001
   DATA "Quit",          1000
   DATA "",-1
   DATA "Init",          2000
   DATA "Demo",          2001
   DATA "OhioFn",        2002
   DATA "LoopTest",      2003
   DATA "LoopTest5",     2004
   DATA "LoopTest6",     2005
   DATA "VentLoop",      2006
   DATA "",-1

' Error trap to make screen independent
VideoErr:
   SELECT CASE BestMode    ' Fall through until something works
      CASE VGA
         BestMode = MCGA
         Available = "12BD"
      CASE MCGA
         BestMode = EGA256
         Available = "12789"
      CASE EGA256
         BestMode = CGA
         Available = "12"
      CASE CGA
         BestMode = MONO
         Available = "A"
```

SUBSTITUTE SHEET

MenuSys.Bas - QBasic PopDown Menu System

```
    CASE MONO
      BestMode = HERC
      Available = "3"
    CASE ELSE
      PRINT "Sorry. Graphics not available. Need MsHerc.Com?"
      END
  END SELECT
  RESUME ' Trap to detect 64K EGA
EGAErr:
  BestMode = EGA64
  Available = "12789"
  RESUME NEXT ' Trap to determine initial number of rows so they can be
restored
RowErr:
  IF InitRows = 50 THEN
    InitRows = 43
    RESUME
  ELSE
    InitRows = 25
    RESUME NEXT
  END IF '$Page  $SubTitle:'SUB AboutBox'
```

SUBSTITUTE SHEET

```
MenuSys.Bas - QBasic PopDown Menu System
SUB AboutBox

SUB AboutBox
   REDIM a$(9)
   DIM Ky$ a$(0) = "  Status  "
   a$(1) = ""
   a$(2) = "Version - " + LPad$(STR$(PgmVersion), 7)
   a$(3) = ""
   a$(4) = " Memory Available "
   a$(5) = "String - " + LPad$(STR$(FRE("x")), 8)
   a$(6) = "Array  - " + LPad$(STR$(FRE(-1)), 8)
   a$(7) = "Stack  - " + LPad$(STR$(FRE(-2)), 8)
   a$(8) = ""
   a$(9) = "Press any key to continue"

MsgBox a$(), 9, Ky$, -1, -1

ERASE a$
END SUB

'$Page  $SubTitle:'SUB BoxIt'
```

MenuSys.Bas - QBasic PopDown Menu System
SUB BoxIt

```
SUB BoxIt (x1 AS INTEGER, y1 AS INTEGER, x2 AS INTEGER, y2 AS
INTEGER)

DIM Lt$, Hl$, Rt$, Vl$, Lb$, Rb$, top$, mdl$, btm$
  DIM r AS INTEGER, wide AS INTEGER 'Line chars
  Lt$ = "┌": Hl$ = "=": Rt$ = "┐"
  Vl$ = "║"
  Lb$ = "└": Rb$ = "┘"

wide = x2 - x1 + 1 - 2
  top$ = Lt$ + STRING$(wide, Hl$) + Rt$
  mdl$ = Vl$ + STRING$(wide, " ") + Vl$
  btm$ = Lb$ + STRING$(wide, Hl$) + Rb$ FOR r = y1 TO y2
    LOCATE r, x1
    IF r = y1 THEN
      PRINT top$;
    ELSEIF r = y2 THEN
      PRINT btm$;
    ELSE
      PRINT mdl$;
    END IF
  NEXT r
END SUB '$Page  $SubTitle:'SUB BrList'
```

MenuSys.Bas - QBasic PopDown Menu System
SUB BrList

```
SUB BrList (txt$(), NumLin AS INTEGER)

'Browse txt$(NumLin) - press ESC to exit
  'txt$(0) is header on line 1

SHARED ForGnd AS INTEGER, BakGnd AS INTEGER

DIM i AS INTEGER, st AS INTEGER, en AS INTEGER
  DIM a$

IF NumLin = 0 THEN EXIT SUB        'nothing to do

COLOR ForGnd, BakGnd
  CLS

'header on line 1
  COLOR BakGnd, ForGnd
  LOCATE 1, 1
  PRINT txt$(0)

COLOR ForGnd, BakGnd
  VIEW PRINT 2 TO 25

'Display list
  st = 1
  en = Min(CSNG(NumLin), 24)

DO
    'update display
    CLS
    FOR i = st TO en
      LOCATE 2 + (i - st), 1
      PRINT txt$(i);
    NEXT i
```

SUBSTITUTE SHEET

MenuSys.Bas - QBasic PopDown Menu System
SUB BrList

```
    DO
      a$ = INKEY$
    LOOP UNTIL a$ <> ""
    SELECT CASE LEN(a$)
      CASE 1                              'ESC to quit
        IF a$ = CHR$(27) THEN EXIT DO
      CASE 2
        SELECT CASE ASC(MID$(a$, 2, 1))
          CASE 71                    'Home
            st = 1
            en = Min(CSNG(NumLin), 24!)
          CASE 79                    'End
            en = NumLin
            st = Max(CSNG(en - 23), 1!)
          CASE 72                    'Up
            st = Max(CSNG(st - 1), 1!)
            en = Min(CSNG(st + 23), CSNG(NumLin))
          CASE 80                    'Down
            en = Min(CSNG(en + 1), CSNG(NumLin))
            st = Max(CSNG(en - 23), 1!)
          CASE 73                    'PgUp
            st = Max(CSNG(st - 24), 1!)
            en = Min(CSNG(st + 23), CSNG(NumLin))
          CASE 81                    'PgDn
            en = Min(CSNG(en + 24), CSNG(NumLin))
            st = Max(CSNG(en - 23), 1!)
          CASE 75                    'Left
          CASE 77                    'Right
'         CASE ELSE
'           PRINT ASC(MID$(a$, 2, 1))
        END SELECT
    END SELECT
```

78

```
MenuSys.Bas - QBasic PopDown Menu System
SUB BrList

LOOP
   VIEW PRINT
END SUB
'$Page   $SubTitle:'FUNCTION CenterStr$'
```

MenuSys.Bas - QBasic PopDown Menu System
FUNCTION CenterStr$

```
FUNCTION CenterStr$ (s$, length AS INTEGER)

' Adds spaces to start and end of s$, until s$ is length chars

IF (LEN(s$) = length) THEN
    CenterStr$ = s$
  ELSEIF (LEN(s$) > length) THEN
    CenterStr$ = MID$(s$, 1, length)
  ELSE
    DO
      s$ = " " + s$ + " "
    LOOP UNTIL (LEN(s$) >= length)
    IF (LEN(s$) > length) THEN s$ = MID$(s$, 1, length)
    CenterStr$ = s$
  END IF
END FUNCTION '$Page  $SubTitle:'FUNCTION Exist'
```

SUBSTITUTE SHEET

80

MenuSys.Bas - QBasic PopDown Menu System
FUNCTION Exist

```
FUNCTION Exist (FileName$)

DIM fp AS INTEGER, size AS LONG fp = FREEFILE
   OPEN FileName$ FOR RANDOM AS #fp
   size = LOF(fp)
   CLOSE #fp IF size = 0 THEN          'File doesn't exist
      KILL FileName$
      Exist = 0
   ELSE
      Exist = -1
   END IF

END FUNCTION

'$Page   $SubTitle:'FUNCTION FUse$'
```

MenuSys.Bas - QBasic PopDown Menu System
FUNCTION FUse$

```
FUNCTION FUse$ (x AS SINGLE, wide AS INTEGER, dec AS INTEGER)

'Returns X as a string of length wide, with dec digits after
decimal

DIM a$
   DIM i AS INTEGER, j AS INTEGER a$ = LTRIM$(STR$(x))

'ensure a decimal point exists
   IF INSTR(a$, ".") = 0 THEN a$ = a$ + "." + STRING$(dec, "0")

'add trailing 0's if necessary
   i = LEN(a$)
   j = INSTR(a$, ".")
   IF (i - j) < dec THEN a$ = a$ + STRING$(dec - (i - j), "0")

'remove trailing 0's if necessary
   i = LEN(a$)
   j = INSTR(a$, ".")
   IF (i - j) > dec THEN a$ = MID$(a$, 1, j + dec)

'pad the correct length
   a$ = LPad$(a$, wide)

FUse$ = a$
END FUNCTION

'$Page  $SubTitle:'SUB GetConfig'
```

MenuSys.Bas - QBasic PopDown Menu System
SUB GetConfig

```
'    ==========================    GetConfig
=================================
'   Get the starting number of lines and the video adapter.
'
'==================================================================
========
'
SUB GetConfig STATIC
   SHARED InitRows AS INTEGER, BestMode AS INTEGER, Available AS
STRING
   ' Assume 50 line display and fall through error
   ' until we get the actual number
   InitRows = 50
   ON ERROR GOTO RowErr
   LOCATE InitRows, 1
   ' Assume best possible screen mode
   BestMode = VGA
   Available = "12789BCD"

ON ERROR GOTO VideoErr
   ' Fall through error trap until a mode works
   SCREEN BestMode
   ' If EGA, then check pages to see whether more than 64K
   ON ERROR GOTO EGAErr
   IF BestMode = EGA256 THEN SCREEN 8, , 1

ON ERROR GOTO 0

' Reset text mode
   SCREEN 0, , 0
   WIDTH 80, 25

END SUB
'$Page   $SubTitle:'SUB Init'
```

MenuSys.Bas - QBasic PopDown Menu System
SUB Init

```
SUB Init
   SHARED CurPath$, ForGnd AS INTEGER, BakGnd AS INTEGER
   DIM fp AS INTEGER, Choice AS INTEGER
   REDIM Men$(2)
   'Ask Dos for current Path
   SHELL "CD > Dir.Tmp"
   fp = FREEFILE
   OPEN "Dir.Tmp" FOR INPUT AS #fp
      INPUT #fp, CurPath$
   CLOSE #fp
   KILL "Dir.Tmp"
   IF RIGHT$(CurPath$, 1) <> "\" THEN CurPath$ = CurPath$ + "\"
   'Select colour or monochrome
   Men$(0) = "Select your Monitor"
   Men$(1) = "Colour"
   Men$(2) = "Monochrome"
   CLS
   ForGnd = 7
   BakGnd = 0
' LOCATE 10, 31
' PRINT "Select your Monitor"
   DO
   LOCATE 12, 34
      PopUpList Men$(), 2, Choice, Ky$, -1, 0           'pop
   LOOP UNTIL Ky$ = CHR$(13)

CLS
   IF Ky$ = CHR$(13) AND Choice = 1 THEN BakGnd = 1      'colour
   COLOR ForGnd, BakGnd
   ERASE Men$
END SUB '$Page  $SubTitle:'FUNCTION LPad$'
```

MenuSys.Bas - QBasic PopDown Menu System
FUNCTION LPad$

```
FUNCTION LPad$ (s$, length AS INTEGER)

' Adds spaces to s$ on left, until s$ is length chars

IF (LEN(s$) = length) THEN
    LPad$ = s$
  ELSEIF (LEN(s$) > length) THEN
    LPad$ = MID$(s$, 1, length)
  ELSE
    DO
      s$ = " " + s$
    LOOP UNTIL (LEN(s$) = length)
    LPad$ = s$
  END IF
END FUNCTION '$Page  $SubTitle:'SUB MainMenu'
```

MenuSys.Bas - QBasic PopDown Menu System
SUB MainMenu

```
SUB MainMenu
   SHARED CurPath$, ForGnd AS INTEGER, BakGnd AS INTEGER

DIM i AS INTEGER, Bchoice AS INTEGER, numpickM AS INTEGER
   DIM Done AS INTEGER, tmp AS INTEGER, barX AS INTEGER
   DIM DataSet AS INTEGER, Redraw AS INTEGER, RtnCode AS INTEGER
   DIM numpick AS INTEGER, Choice AS INTEGER
   DIM m$, Mky$, Ky$, CmdLst$ RESTORE MainMenuData        'determine # picks
   numpickM = 0
   DO
      READ m$
      numpickM = numpickM + 1
   LOOP UNTIL m$ = ""
   numpickM = numpickM - 1

REDIM MBar$(numpickM)

RESTORE MainMenuData        'Load the menu data and cmd table
   FOR i = 1 TO numpickM
      READ MBar$(i)
   NEXT i 'Init pull down valid command table
   'enter, esc, left & right arrow
   CmdLst$ = CHR$(13) + CHR$(27) + (CHR$(0) + CHR$(75)) + (CHR$(0)
 + CHR$(77))

Done = 0
   Redraw = 0

DO
      DO
```

MenuSys.Bas - QBasic PopDown Menu System
SUB MainMenu

```
    MenuBar MBar$(), numpickM, Bchoice, Mky$, barX, Redraw
LOOP UNTIL Mky$ = CHR$(13)

'count # picks in the selected pull down menu
RESTORE PullDownMenuData

DataSet = 0

DO WHILE DataSet < Bchoice numpick = 0                'scan group of pull down menu
data
    DO
      READ m$, tmp
      numpick = numpick + 1
    LOOP UNTIL tmp = -1 numpick = numpick - 1    'correct # items in group
    DataSet = DataSet + 1    'correct ptr to pull down group
LOOP REDIM Menu$(numpick), cmd(numpick) AS INTEGER     'allocate
memory 'Load the selected pull down menu RESTORE PullDownMenuData DataSet = 0

'scan group of pull down menu data, until at start of desired
one
DO UNTIL DataSet = Bchoice - 1
    DO
```

MenuSys.Bas - QBasic PopDown Menu System
SUB MainMenu

```
        READ m$, tmp
    LOOP UNTIL tmp = -1

DataSet = DataSet + 1     'correct ptr to pull down group

LOOP

FOR i = 1 TO numpick      'load pull down data
       READ Menu$(i), cmd(i)
    NEXT i VIEW PRINT 2 TO 25        'clear screen under menu bar
    COLOR ForGnd, 0
    CLS 2
    COLOR ForGnd, BakGnd
    VIEW PRINT DO
       LOCATE 2, barX
       PopUpList Menu$(), numpick, Choice, Ky$, 0, 0        'no pop, no center
    LOOP UNTIL INSTR(CmdLst$, Ky$) > 0

SELECT CASE Ky$

CASE CHR$(0) + CHR$(77)   'right arrow
          Bchoice = Bchoice + 1
          IF Bchoice > numpickM THEN Bchoice = 1
          Redraw = -1      'unpop pulldown & move to adjacent pull down CASE CHR$(0) + CHR$(75)   'left arrow
          Bchoice = Bchoice - 1
```

```
MenuSys.Bas - QBasic PopDown Menu System
SUB MainMenu

IF Bchoice < 1 THEN Bchoice = numpickM
        Redraw = -1      'unpop pulldown & move to adjacent pull down CASE CHR$(27)              'ESC
        Redraw = 0

CASE CHR$(13)              'Enter
        MenuExec cmd(Choice), Done, RtnCode
        Redraw = -1
    END SELECT LOOP UNTIL Done ERASE Menu$, cmd          'deallocate pull down data
  ERASE MBar$
END SUB '$Page   $SubTitle:'FUNCTION Max'
```

MenuSys.Bas - QBasic PopDown Menu System
FUNCTION Max

```
FUNCTION Max (x AS SINGLE, y AS SINGLE)
  IF x > y THEN
    Max = x
  ELSE
    Max = y
  END IF
END FUNCTION

'$Page  $SubTitle:'SUB MenuBar'
```

90

MenuSys.Bas - QBasic PopDown Menu System
SUB MenuBar

```
SUB MenuBar (Item$(), NumLin AS INTEGER, Choice AS INTEGER, Ky$,
x AS INTEGER, Redraw AS INTEGE
R)

' Horizontal Menu Bar
' Selected by down arrow or enter
' if Redraw true, the menu bar is only updated
' Item$(0) is ignored SHARED ForGnd AS INTEGER, BakGnd AS INTEGER DIM maxLen AS INTEGER, i AS INTEGER
  DIM hot AS INTEGER, oldhot AS INTEGER, Done AS INTEGER
  DIM mask$, cmd$, CmdTbl$ maxLen = 0
  FOR i = 1 TO NumLin          'get max width
     IF LEN(Item$(i)) > maxLen THEN maxLen = LEN(Item$(i))
  NEXT i
  IF maxLen + NumLin * 2 > 80 THEN STOP 'generate table for column positions for each pick REDIM whereX(NumLin) AS INTEGER whereX(1) = 1
  FOR i = 2 TO NumLin
     whereX(i) = whereX(i - 1) + LEN(Item$(i - 1)) + 2
  NEXT i VIEW PRINT 1 TO 1
  COLOR BakGnd, ForGnd
  CLS 2
```

SUBSTITUTE SHEET

MenuSys.Bas - QBasic PopDown Menu System
SUB MenuBar

```
  'init command table for 1st letter in Item$
  CmdTbl$ = ""
  FOR i = 1 TO NumLin
    CmdTbl$ = CmdTbl$ + UCASE$(LEFT$(Item$(i), 1))
  NEXT i
  CmdTbl$ = CmdTbl$ + CmdTbl$            'double list to wrap
around IF Choice >= 1 AND Choice <= NumLin THEN
    hot = Choice ELSE
    hot = 1
  END IF
  oldhot = hot 'Draw MenuBar
  FOR i = 1 TO NumLin
    LOCATE 1, whereX(i)
    mask$ = "\" + STRING$(LEN(Item$(i)), " ") + "\"
    IF i = hot THEN COLOR ForGnd, BakGnd
    PRINT USING mask$; " " + Item$(i) + " ";
    IF i = hot THEN COLOR BakGnd, ForGnd NEXT i 'if Redraw, were done
  IF Redraw THEN
    Ky$ = CHR$(13)
    x = whereX(hot)
    VIEW PRINT
    ERASE whereX
    EXIT SUB
  END IF
```

SUBSTITUTE SHEET

MenuSys.Bas - QBasic PopDown Menu System
SUB MenuBar

Done = 0

DO
    IF hot <> oldhot THEN              'update menu bar

'deselect oldhot
      LOCATE 1, whereX(oldhot)
      mask$ = "\" + STRING$(LEN(Item$(oldhot)), " ") + "\"
      PRINT USING mask$; " " + Item$(oldhot) + " ";

'select hot
      LOCATE 1, whereX(hot)
      mask$ = "\" + STRING$(LEN(Item$(hot)), " ") + "\"
      COLOR ForGnd, BakGnd
      PRINT USING mask$; " " + Item$(hot) + " ";
      COLOR BakGnd, ForGnd
    END IF Choice = hot
    oldhot = hot DO
      cmd$ = UCASE$(INKEY$)
    LOOP UNTIL cmd$ <> ""

SELECT CASE LEN(cmd$)

CASE 1              'one char
        Ky$ = cmd$        'save key pressed, to return it
        SELECT CASE ASC(cmd$)
          CASE 27         'Esc
            Done = -1
          CASE 13         'Enter
            Done = -1
```

MenuSys.Bas - QBasic PopDown Menu System
SUB MenuBar

```
          CASE ELSE            '1st letter of command?
            i = INSTR(hot - 1 + 2, CmdTbl$, UCASE$(cmd$))
            IF i > 0 THEN
              hot = (i - 1) + 1
              IF hot > NumLin THEN hot = hot - NumLin
            END IF
        END SELECT CASE 2              'extended char
        SELECT CASE ASC(MID$(cmd$, 2, 1))
          CASE 71         'home
            hot = 1
          CASE 79         'end
            hot = NumLin
          CASE 80         'dn
            Ky$ = CHR$(13)     'dn = enter
            Done = -1
          CASE 77         'right
            hot = hot + 1
            IF hot > NumLin THEN hot = 1
          CASE 75         'left
            hot = hot - 1
            IF hot < 1 THEN hot = NumLin
        END SELECT
    END SELECT
  LOOP UNTIL Done
  'return left x position of item selected on menu bar
  x = whereX(hot)
  VIEW PRINT
  ERASE whereX
END SUB '$Page  $SubTitle:'SUB MenuExec'
```

SUBSTITUTE SHEET

MenuSys.Bas - QBasic PopDown Menu System
SUB MenuExec

```
SUB MenuExec (cmd AS INTEGER, Done AS INTEGER, RtnCode AS
INTEGER) STATIC

' cmd           = command to execute
' done          = if set to -1, causes menu to terminate program
' RtnCode       = error return of command (-1 if fail)

SHARED CurPath$, ForGnd AS INTEGER, BakGnd AS INTEGER
   DIM FileName$

SELECT CASE cmd

CASE 1000                        'quit
        Done = -1

CASE 1001                        'shell
        COLOR 7, 0
        CLS
        PRINT "Type Exit to return to program"
        SHELL
        CLS
        COLOR ForGnd, BakGnd CASE 1002                        'new path
        SelectNewPath CASE 1003                        'about
        AboutBox CASE 1004                        'Open
        SelectFile FileName$ CASE 1010                        'Import PRN..
        LoadVentDatPrn
```

SUBSTITUTE SHEET

```
MenuSys.Bas - QBasic PopDown Menu System
SUB MenuExec

CASE 1011                       'Browse Data
       BrPrnData

CASE 1012                       'Plot Data
       PlotVentDat

CASE 2000
       InitDas16                    'Init Das16

CASE 2001                          'Demo of Acquisition
primatives
       Demo

CASE 2002                          'Demo of Ohio Control
Regression Analysis
       OhioFn CASE 2003                       'Slow LoopTest
       LoopTest CASE 2004                       'Medium speed LoopTest
       LoopTest5

CASE 2005                       'High Speed LoopTest
       LoopTest6

CASE 2006                       'Interrupt LoopTest
       VentLoop

END SELECT
END SUB

'$Page   $SubTitle:'FUNCTION Min'
```

```
MenuSys.Bas - QBasic PopDown Menu System
FUNCTION Min

FUNCTION Min (x AS SINGLE, y AS SINGLE)
   IF x < y THEN
      Min = x
   ELSE
      Min = y
   END IF
END FUNCTION

'$Page   $SubTitle:'SUB MsgBox'
```

MenuSys.Bas - QBasic PopDown Menu System
SUB MsgBox

```
SUB MsgBox (txt$(), NumLin AS INTEGER, Ky$, RestoreScrn AS
INTEGER, Pause AS INTEGER)

' if RestoreScrn NOT true, user must call UnPop
' if Pause true, inkey$ returns Ky$
' Title of box in Txt$(0)

SHARED CurPath$, ForGnd AS INTEGER, BakGnd AS INTEGER
   DIM x1 AS INTEGER, y1 AS INTEGER, x2 AS INTEGER, y2 AS INTEGER
   DIM i AS INTEGER, maxLen AS INTEGER 'calcute area of centered box
   maxLen = 0
   FOR i = 0 TO NumLin
      IF LEN(txt$(i)) > maxLen THEN maxLen = LEN(txt$(i))
   NEXT i
   IF maxLen > 78 THEN maxLen = 78 x1 = 41 - (maxLen + 2) \ 2
   x2 = x1 + maxLen + 1
   y1 = 12 - (NumLin + 2) \ 2
   y2 = y1 + (NumLin + 1)

Pop x1, y1, x2, y2
   BoxIt x1, y1, x2, y2

'Title - Txt$(0) not blank
   IF txt$(0) <> "" THEN
      LOCATE y1, (x1 + (x2 - x1 + 1) \ 2) - LEN(txt$(0)) \ 2
      PRINT txt$(0);
   END IF FOR i = 1 TO NumLin
      LOCATE y1 + i, x1 + 1
```

SUBSTITUTE SHEET

```
MenuSys.Bas - QBasic PopDown Menu System
SUB MsgBox

PRINT CenterStr$(txt$(i), maxLen);
  NEXT i

IF Pause THEN
    DO
      Ky$ = UCASE$(INKEY$)
    LOOP UNTIL Ky$ <> ""
  END IF IF RestoreScrn THEN UnPop
END SUB '$Page  $SubTitle:'SUB Pop'
```

MenuSys.Bas - QBasic PopDown Menu System
SUB Pop

```
SUB Pop (x1 AS INTEGER, y1 AS INTEGER, x2 AS INTEGER, y2 AS
INTEGER)

SHARED PopBuf() AS INTEGER
  DIM r AS INTEGER, c AS INTEGER, i AS INTEGER

PopBuf(1, 0) = x1
  PopBuf(1, 1) = y1
  PopBuf(2, 0) = x2
  PopBuf(2, 1) = y2
  i = 3
  FOR r = y1 TO y2
    FOR c = x1 TO x2
      PopBuf(i, 0) = SCREEN(r, c, 0)
      PopBuf(i, 1) = SCREEN(r, c, 1)
      i = i + 1
    NEXT c
  NEXT r
END SUB

'$Page  $SubTitle:'SUB PopUpList'
```

100

MenuSys.Bas - QBasic PopDown Menu System
SUB PopUpList

```
SUB PopUpList (Item$(), NumLin AS INTEGER, Choice AS INTEGER,
Ky$, SaveScrn AS INTEGER, Center
AS INTEGER)

' if SaveScrn TRUE, screen is popped/unpopped
' if Center TRUE, LIST is centered
' Left & Right arrow exit, with Ky$ set to [0 75], [0 77]
respectivly
' if Choice in range, list is scrolled to selected item SHARED ForGnd AS INTEGER, BakGnd AS INTEGER DIM whereX AS INTEGER, whereY AS INTEGER, maxLen AS INTEGER,
i AS INTEGER
  DIM x1 AS INTEGER, y1 AS INTEGER, x2 AS INTEGER
  DIM y2 AS INTEGER, ps AS INTEGER, pe AS INTEGER, hot AS INTEGER
  DIM oldhot AS INTEGER, Done AS INTEGER, scroll AS INTEGER
  DIM mask$, CmdTbl$ maxLen = 0
  whereY = CSRLIN       'save x,y position @ calling
  whereX = POS(1)

FOR i = 0 TO NumLin      'get max width
    IF LEN(Item$(i)) > maxLen THEN maxLen = LEN(Item$(i))
  NEXT i
  IF maxLen > 78 THEN STOP 'choose popup area
  IF NOT Center THEN
    y1 = whereY
    IF whereY + NumLin + 1 > 24 THEN     'determine lower screen
limits
      y2 = 24
```

101

MenuSys.Bas - QBasic PopDown Menu System
SUB PopUpList

```
   ELSE
      y2 = whereY + NumLin + 1
   END IF x1 = whereX                       'cal popup hort region
   x2 = whereX + maxLen + 1
   IF x2 > 80 THEN                   'force col 80 = right edge
      x2 = 80
      x1 = 80 - maxLen - 1
   END IF ELSE                                'Center popup x1 = 40 - (maxLen + 2) \ 2
   x2 = x1 + maxLen + 1
   y1 = 12 - (NumLin + 2) \ 2
   IF y1 < 2 THEN y1 = 2
   y2 = y1 + (NumLin - 1 + 2)
   IF y2 > 24 THEN y2 = 24
 END IF COLOR ForGnd, BakGnd
 IF SaveScrn THEN Pop x1, y1, x2, y2    'save region on screen
 BoxIt x1, y1, x2, y2                   'box it 'Title - if not blank
 IF Item$(0) <> "" THEN
    LOCATE y1, (x1 + (x2 - x1 + 1) \ 2) - LEN(Item$(0)) \ 2
    PRINT Item$(0);
 END IF mask$ = "\" + STRING$(maxLen - 2, " ") + "\"

ps = 1
```

SUBSTITUTE SHEET

102

MenuSys.Bas - QBasic PopDown Menu System
SUB PopUpList

```
  pe = ps + (y2 - y1 - 2)

'if value of Choice called with is in range - use it
  IF Choice >= ps AND Choice <= NumLin THEN
    hot = Choice
    DO WHILE hot > pe
      ps = ps + 1
      pe = pe + 1
    LOOP
  ELSE
    hot = ps
  END IF
  oldhot = hot
  Done = 0
  scroll = 0
  'init command table for 1st letter in Item$
  CmdTbl$ = ""
  FOR i = 1 TO NumLin
    CmdTbl$ = CmdTbl$ + UCASE$(LEFT$(Item$(i), 1))
  NEXT i CmdTbl$ = CmdTbl$ + CmdTbl$            'double list to wrap around
  FOR i = ps TO pe                       'draw list
    LOCATE y1 + 1 + i - ps, x1 + 1
    IF i = hot THEN COLOR BakGnd, ForGnd
    PRINT USING mask$; Item$(i);
    IF i = hot THEN COLOR ForGnd, BakGnd
  NEXT i
  DO
    'Display picks
    IF hot >= ps AND hot <= pe THEN      'pick on screen
      LOCATE y1 + 1 + oldhot - ps, x1 + 1  'deselect old
      PRINT USING mask$; Item$(oldhot);
```

MenuSys.Bas - QBasic PopDown Menu System
SUB PopUpList

```
        LOCATE y1 + 1 + hot - ps, x1 + 1           'select new
        COLOR BakGnd, ForGnd
        PRINT USING mask$; Item$(hot);
        COLOR ForGnd, BakGnd ELSE                                           'scroll or moved by 1 line IF scroll THEN                             'scroll list scroll = 0
            IF hot < ps THEN                       'scroll up
                ps = ps - (y2 - y1 - 1)
                IF ps < 1 THEN ps = 1
                pe = ps + (y2 - y1 - 2)

ELSE                                   'scroll down
                pe = pe + (y2 - y1 - 1)
                IF pe > NumLin THEN pe = NumLin
                ps = pe - (y2 - y1 - 2)
            END IF ELSEIF hot < ps THEN                       'scroll up 1
            ps = hot
            pe = ps + (y2 - y1 - 2)

ELSE                                       'scroll down 1
            pe = hot
            ps = pe - (y2 - y1 - 2)

IF ps < 1 THEN
                ps = 1
                pe = ps + (y2 - y1 - 2)
            END IF
```

SUBSTITUTE SHEET

104

MenuSys.Bas - QBasic PopDown Menu System
SUB PopUpList

```
    END IF

FOR i = ps TO pe                         'draw list
      LOCATE y1 + 1 + i - ps, x1 + 1
      IF i = hot THEN COLOR BakGnd, ForGnd
      PRINT USING mask$; Item$(i);
      IF i = hot THEN COLOR ForGnd, BakGnd
    NEXT i

END IF

Choice = hot
    oldhot = hot

DO
       cmd$ = UCASE$(INKEY$)
    LOOP UNTIL cmd$ <> ""

SELECT CASE LEN(cmd$)

CASE 1              'one char
        Ky$ = cmd$        'save key pressed, to return it
        SELECT CASE ASC(cmd$)
          CASE 27         'Esc
            Done = -1
          CASE 13         'Enter
            Done = -1
          CASE ELSE            '1st letter of command?
            i = INSTR(hot - 1 + 2, CmdTbl$, UCASE$(cmd$))
            IF i > 0 THEN
              hot = (i - 1) + 1
              IF hot > NumLin THEN hot = hot - NumLin
            END IF
        END SELECT
```

MenuSys.Bas - QBasic PopDown Menu System
SUB PopUpList

```
        CASE 2               'extended char
          SELECT CASE ASC(MID$(cmd$, 2, 1))
            CASE 71         'home
              hot = 1
            CASE 79         'end
              hot = NumLin
            CASE 73         'pg up
              hot = hot - (y2 - y1 - 1)
              IF hot < 1 THEN hot = 1
              scroll = -1
            CASE 81         'pg dn
              hot = hot + (y2 - y1 - 1)
              IF hot > NumLin THEN hot = NumLin
              scroll = -1
            CASE 72         'up
              hot = hot - 1
              IF hot < 1 THEN hot = NumLin
            CASE 80         'dn
              hot = hot + 1
              IF hot > NumLin THEN hot = 1
              CASE 77       'right
                Ky$ = cmd$
                Done = -1
              CASE 75       'left
                Ky$ = cmd$
                Done = -1
          END SELECT
      END SELECT LOOP UNTIL Done
  IF SaveScrn THEN UnPop
END SUB
'$Page  $SubTitle:'FUNCTION RPad$'
```

106

MenuSys.Bas - QBasic PopDown Menu System
FUNCTION RPad$

```
FUNCTION RPad$ (s$, length AS INTEGER)

' Adds spaces to s$ on right, until s$ is length chars

IF (LEN(s$) = length) THEN
    RPad$ = s$
  ELSEIF (LEN(s$) > length) THEN
    RPad$ = MID$(s$, 1, length)
  ELSE
    DO
      s$ = s$ + " "
    LOOP UNTIL (LEN(s$) = length)
    RPad$ = s$
  END IF
END FUNCTION '$Page  $SubTitle:'SUB SelectFile'
```

MenuSys.Bas - QBasic PopDown Menu System
SUB SelectFile

```
SUB SelectFile (FileName$)

SHARED CurPath$, ForGnd AS INTEGER, BakGnd AS INTEGER

DIM fp AS INTEGER, nfil AS INTEGER, Choice AS INTEGER, size AS
LONG
  DIM FilSpec$, Ky$ FileName$ = ""

REDIM Msg$(3)
  Msg$(0) = "Select File"
  Msg$(1) = ""
  Msg$(2) = "Scanning " + CurPath$
  Msg$(3) = ""

MsgBox Msg$(), 3, Ky$, 0, 0      'no unpop, no pause
  ERASE Msg$

SHELL "Dir " + CurPath$ + "*.* /ON /A-D /B > Dir.Tmp"

fp = FREEFILE
  OPEN "Dir.Tmp" FOR RANDOM AS #fp LEN = 1
  size = LOF(fp)
  CLOSE #fp IF size = 0 THEN
    UnPop                          'remove MsgBox message REDIM Msg$(7)
    Msg$(0) = "Select File"
    Msg$(1) = ""
    Msg$(2) = "---- WARNING ----"
    Msg$(3) = ""
```

108

MenuSys.Bas - QBasic PopDown Menu System
SUB SelectFile

```
    Msg$(4) = CurPath$
    Msg$(5) = "contained NO files"
    Msg$(6) = ""
    Msg$(7) = "Press any key to continue"
    MsgBox Msg$(), 7, Ky$, -1, -1    'unpop, pause
    ERASE Msg$ KILL "Dir.Tmp"
    EXIT SUB

END IF nfil = 0
  OPEN "Dir.Tmp" FOR INPUT AS #fp
  WHILE NOT EOF(fp)
     LINE INPUT #fp, FilSpec$
     FilSpec$ = LTRIM$(RTRIM$(FilSpec$))
     IF LEN(FilSpec$) > 0 AND FilSpec$ <> "DIR.TMP" THEN nfil =
nfil + 1
  WEND
  CLOSE #fp IF nfil = 0 THEN
    UnPop                              'remove MsgBox message REDIM Msg$(7)
    Msg$(0) = "Select File"
    Msg$(1) = ""
    Msg$(2) = "---- WARNING ----"
    Msg$(3) = ""
    Msg$(4) = CurPath$
    Msg$(5) = "contained NO files"
    Msg$(6) = ""
    Msg$(7) = "Press any key to continue"
```

SUBSTITUTE SHEET

MenuSys.Bas - QBasic PopDown Menu System
SUB SelectFile

```
      MsgBox Msg$(), 7, Ky$, -1, -1     'unpop, pause
      ERASE Msg$

KILL "Dir.Tmp"
      EXIT SUB
   END IF

REDIM Fil$(nfil)

fp = FREEFILE
   OPEN "Dir.Tmp" FOR INPUT AS #fp
   nfil = 1
   WHILE NOT EOF(fp)
      LINE INPUT #fp, Fil$(nfil)
      Fil$(nfil) = LTRIM$(RTRIM$(Fil$(nfil)))
      IF LEN(Fil$(nfil)) > 0 AND Fil$(nfil) <> "DIR.TMP" THEN nfil
= nfil + 1
   WEND
   nfil = nfil - 1
   CLOSE #fp KILL "Dir.Tmp"
   UnPop                              'remove MsgBox message
   Fil$(0) = CurPath$ + "*.*"
   DO
      PopUpList Fil$(), nfil, Choice, Ky$, -1, -1         'pop,
center
   LOOP UNTIL Ky$ = CHR$(13) OR Ky$ = CHR$(27)

IF Ky$ = CHR$(13) THEN FileName$ = Fil$(Choice)

ERASE Fil$
END SUB
'$Page  $SubTitle:'SUB SelectNewPath'
```

110

MenuSys.Bas - QBasic PopDown Menu System
SUB SelectNewPath

SUB SelectNewPath

SHARED CurPath$, ForGnd AS INTEGER, BakGnd AS INTEGER

DIM fp AS INTEGER, ndir AS INTEGER, Choice AS INTEGER
   DIM Drv$, DirSpec$, Ky$ REDIM Msg$(4)
   Msg$(0) = "Select New Path"
   Msg$(1) = ""
   Msg$(2) = "Current Path: " + CurPath$
   Msg$(3) = ""
   Msg$(4) = "Drive to Scan [A..Z, ESC] = "

DO
      MsgBox Msg$(), 4, Drv$, -1, -1
   LOOP UNTIL INSTR("ABCDEFGHIJKLMNOPQRSTUVWXYZ" + CHR$(13) +
CHR$(27), Drv$) > 0
   ERASE Msg$

IF Drv$ = CHR$(13) THEN
      Drv$ = LEFT$(CurPath$, 1)
   ELSEIF Drv$ = CHR$(27) THEN
      EXIT SUB
   END IF REDIM Msg$(3)
   Msg$(0) = "Select New Path"
   Msg$(1) = ""
   Msg$(2) = "Scanning Directory on " + Drv$ + ":"
   Msg$(3) = ""

MsgBox Msg$(), 3, Ky$, 0, 0      'no unpop, no pause
   ERASE Msg$

SUBSTITUTE SHEET

111

MenuSys.Bas - QBasic PopDown Menu System
SUB SelectNewPath

```
  SHELL "Dir " + Drv$ + ":\ /AD /S /B | Sort > Dir.Tmp"
  fp = FREEFILE
  ndir = 1
  OPEN "Dir.Tmp" FOR INPUT AS #fp
  WHILE NOT EOF(fp)
    LINE INPUT #fp, DirSpec$
    ndir = ndir + 1
  WEND CLOSE #fp IF ndir = 2 AND LEN(DirSpec$) = 0 THEN        'Drive had no
sub-dirs
    ndir = 1
  END IF REDIM Fdir$(ndir)

Fdir$(1) = Drv$ + ":\"          'Root Dir

IF ndir > 1 THEN
    fp = FREEFILE

OPEN "Dir.Tmp" FOR INPUT AS #fp
    ndir = 2
    WHILE NOT EOF(fp)
      LINE INPUT #fp, Fdir$(ndir)
      ndir = ndir + 1
    WEND
    ndir = ndir - 1
    CLOSE #fp
  END IF KILL "Dir.Tmp"
```

SUBSTITUTE SHEET

MenuSys.Bas - QBasic PopDown Menu System
SUB SelectNewPath

```
  UnPop                              'remove MsgBox message

IF ndir = 1 THEN
    REDIM Msg$(6)
    Msg$(0) = "Select New Path"
    Msg$(1) = ""
    Msg$(2) = "---- WARNING ----"
    Msg$(3) = ""
    Msg$(4) = Drv$ + ": had NO directories"
    Msg$(5) = ""
    Msg$(6) = "Press any key to continue"

MsgBox Msg$(), 6, Ky$, -1, -1    'unpop, pause
    ERASE Msg$
  END IF

Fdir$(0) = "Select New Path"
  DO

PopUpList Fdir$(), ndir, Choice, Ky$, -1, -1         'pop,
center
  LOOP UNTIL Ky$ = CHR$(13) OR Ky$ = CHR$(27)

IF Ky$ = CHR$(13) THEN
    CurPath$ = Fdir$(Choice)
    IF RIGHT$(CurPath$, 1) <> "\" THEN CurPath$ = CurPath$ + "\"
  END IF ERASE Fdir$
END SUB '$Page  $SubTitle:'SUB SetConfig'
```

MenuSys.Bas - QBasic PopDown Menu System
SUB SetConfig

```
'    ==========================     SetConfig
================================
'    Sets the correct values for each field of the VC variable. They
'    vary depending on Mode and on the current configuration.
'
==================================================================
========
'
SUB SetConfig (mode AS INTEGER) STATIC SHARED VC AS Config, BestMode AS INTEGER SELECT CASE mode
        CASE 1    ' Four-color graphics for CGA, EGA, VGA, and MCGA
            IF BestMode = CGA OR BestMode = MCGA THEN
                VC.Colors = 0
            ELSE
                VC.Colors = 16
            END IF
            VC.Atribs = 4
            VC.XPix = 319
            VC.YPix = 199
            VC.TCOL = 40
            VC.TROW = 25
        CASE 2    ' Two-color medium-res graphics for CGA, EGA, VGA, and MCGA
            IF BestMode = CGA OR BestMode = MCGA THEN
                VC.Colors = 0
            ELSE
                VC.Colors = 16
            END IF
            VC.Atribs = 2
            VC.XPix = 639
```

SUBSTITUTE SHEET

MenuSys.Bas - QBasic PopDown Menu System
SUB SetConfig

```
            VC.YPix = 199
            VC.TCOL = 80
            VC.TROW = 25
        CASE 3    ' Two-color high-res graphics for Hercules
            VC.Colors = 0
            VC.Atribs = 2
            VC.XPix = 719
            VC.YPix = 347
            VC.TCOL = 80
            VC.TROW = 25
        CASE 7    ' 16-color medium-res graphics for EGA and VGA
            VC.Colors = 16
            VC.Atribs = 16
            VC.XPix = 319
            VC.YPix = 199
            VC.TCOL = 40
            VC.TROW = 25
        CASE 8    ' 16-color high-res graphics for EGA and VGA
            VC.Colors = 16
            VC.Atribs = 16
            VC.XPix = 639
            VC.YPix = 199
            VC.TCOL = 80
            VC.TROW = 25
        CASE 9    ' 16- or 4-color very high-res graphics for EGA
and VGA
            VC.Colors = 64
            IF BestMode = EGA64 THEN VC.Atribs = 4 ELSE VC.Atribs
= 16
            VC.XPix = 639
            VC.YPix = 349
            VC.TCOL = 80
            VC.TROW = 25
```

SUBSTITUTE SHEET

115

MenuSys.Bas - QBasic PopDown Menu System
SUB SetConfig

```
        CASE 10    ' Two-color high-res graphics for EGA or VGA
monochrome
            VC.Colors = 0
            VC.Atribs = 2
            VC.XPix = 319
            VC.YPix = 199
            VC.TCOL = 80
            VC.TROW = 25
        CASE 11    ' Two-color very high-res graphics for VGA and
MCGA
            ' Note that for VGA screens 11, 12, and 13, more colors
are
            ' available, depending on how the colors are mixed.
            VC.Colors = 216
            VC.Atribs = 2
            VC.XPix = 639
            VC.YPix = 479
            VC.TCOL = 80
            VC.TROW = 30
        CASE 12    ' 16-color very high-res graphics for VGA
            VC.Colors = 216
            VC.Atribs = 16
            VC.XPix = 639
            VC.YPix = 479
            VC.TCOL = 80
            VC.TROW = 30
        CASE 13    ' 256-color medium-res graphics for VGA and MCGA
            VC.Colors = 216
            VC.Atribs = 256
            VC.XPix = 639
            VC.YPix = 479
            VC.TCOL = 40
            VC.TROW = 25
```

SUBSTITUTE SHEET

116

MenuSys.Bas - QBasic PopDown Menu System
SUB SetConfig

```
        CASE ELSE
            VC.Colors = 16
            VC.Atribs = 16
            VC.XPix = 0
            VC.YPix = 0
            VC.TCOL = 80
            VC.TROW = 25
            VC.Scrn = 0
            EXIT SUB
    END SELECT
    VC.Scrn = mode

END SUB

FUNCTION StrTok$ (Srce$, Delim$)
STATIC Start%, SaveStr$

' If first call, make a copy of the string.
    IF Srce$ <> "" THEN
        Start% = 1: SaveStr$ = Srce$
    END IF BegPos% = Start%: Ln% = LEN(SaveStr$)
    ' Look for start of a token (character that isn't delimiter).
    WHILE BegPos% <= Ln% AND INSTR(Delim$, MID$(SaveStr$, BegPos%,
1)) <> 0
        BegPos% = BegPos% + 1
    WEND
    ' Test for token start found.
    IF BegPos% > Ln% THEN
        StrTok$ = "": EXIT FUNCTION
    END IF
    ' Find the end of the token.
    EndPos% = BegPos%
```

SUBSTITUTE SHEET

117

MenuSys.Bas - QBasic PopDown Menu System
SUB SetConfig

```
    WHILE EndPos% <= Ln% AND INSTR(Delim$, MID$(SaveStr$, EndPos%,
1)) = 0
        EndPos% = EndPos% + 1
    WEND
    StrTok$ = MID$(SaveStr$, BegPos%, EndPos% - BegPos%)
    ' Set starting point for search for next token.
    Start% = EndPos%

END FUNCTION

'$Page  $SubTitle:'SUB TestGrModes'
```

118

MenuSys.Bas - QBasic PopDown Menu System
SUB TestGrModes

SUB TestGrModes

SHARED VC AS Config, InitRows AS INTEGER, BestMode AS INTEGER,
Available AS STRING DIM i AS INTEGER, mode AS INTEGER, a$
   'test all modes
   FOR i = 1 TO LEN(Available)
      a$ = MID$(Available, i, 1)
      IF a$ >= "1" AND a$ <= "9" THEN
         mode = VAL(a$)
      ELSE
         mode = (ASC(a$) - ASC("A") + 1) + 9
      END IF
      SetConfig mode
      SCREEN VC.Scrn
      PRINT "Vc.Scrn"; VC.Scrn
      PRINT "Vc.Colors"; VC.Colors
      PRINT "Vc.Atribs"; VC.Atribs
      PRINT "Vc.XPix"; VC.XPix
      PRINT "Vc.YPix"; VC.YPix
      PRINT "Vc.TCOL"; VC.TCOL
      PRINT "Vc.TROW"; VC.TROW
      PRINT "InitRows"; InitRows
      PRINT "BestMode"; BestMode
      PRINT "Available"; Available
      INPUT a$ SCREEN 0
      WIDTH 80, InitRows
   NEXT i
END SUB '$Page   $SubTitle:'SUB UnPop'

SUBSTITUTE SHEET

119

MenuSys.Bas - QBasic PopDown Menu System
SUB UnPop

SUB UnPop

SHARED PopBuf() AS INTEGER, ForGnd AS INTEGER, BakGnd AS INTEGER
    DIM r AS INTEGER, c AS INTEGER, i AS INTEGER i = 3
    FOR r = PopBuf(1, 1) TO PopBuf(2, 1)
      FOR c = PopBuf(1, 0) TO PopBuf(2, 0)
        LOCATE r, c
        COLOR (PopBuf(i, 1) AND &HF), (PopBuf(i, 1) AND &HF0) \ 16
        PRINT CHR$(PopBuf(i, 0));
        i = i + 1
      NEXT c
    NEXT r

COLOR ForGnd, BakGnd
END SUB

43949 Bytes Available
26833 Bytes Free

0 Warning Error(s)
    0 Severe  Error(s)

SUBSTITUTE SHEET

120

VentLib.Bas - Ohio 7000 Ventilator Control

```
'$Title:'VentLib.Bas    -    Ohio    7000    Ventilator    Control'
$LineSize:112'

'VentLib
'Oct 2/93
'Chris McLennan

'MenuSys.Bas
DECLARE FUNCTION FUse$ (x AS SINGLE, wide AS INTEGER, dec AS INTEGER)
DECLARE FUNCTION LPad$ (s$, length AS INTEGER)
DECLARE FUNCTION StrTok$ (Srce$, Delim$)

DECLARE SUB BrList (txt$(), NumLin AS INTEGER)
DECLARE SUB MsgBox (txt$(), NumLin AS INTEGER, Ky$, RestoreScrn AS INTEGER, Pause AS INTEGER)
DECLARE SUB SelectFile (FileName$)
DECLARE SUB SetConfig (Mode AS INTEGER)
DECLARE SUB UnPop ()

'DasLib.Bas
DECLARE FUNCTION A2dToVolt! (A2dVal AS INTEGER)
DECLARE FUNCTION VoltToD2a% (Volt!)
DECLARE SUB DasMode0 ()
DECLARE SUB DasMode1 (ChLow AS INTEGER, ChHigh AS INTEGER)
DECLARE SUB DasMode2 (NextCh AS INTEGER, ChLow AS INTEGER, ChHigh AS INTEGER)
DECLARE SUB DasMode3 (A2dData AS INTEGER, A2dCh AS INTEGER)
DECLARE SUB DasMode4 (NumPts AS INTEGER)
DECLARE SUB DasMode5 (NumPts AS INTEGER, Cycle AS INTEGER)
DECLARE SUB DasMode6 (NumPts AS INTEGER, Cycle AS INTEGER)
DECLARE SUB DasMode7 ()
DECLARE SUB DasMode8 (Op AS INTEGER, Status AS INTEGER, Count AS INTEGER)
DECLARE SUB DasMode9 (NumPts AS INTEGER, StartPt AS INTEGER)
```

SUBSTITUTE SHEET

121

VentLib.Bas - Ohio 7000 Ventilator Control

```
  DECLARE SUB DasMode15 (D2aCh AS INTEGER, D2aData AS INTEGER)
  DECLARE SUB DasMode16 (D2aDat0 AS INTEGER, D2aDat1 AS INTEGER)
  DECLARE SUB DasMode17 (Rate!)

'VentLib.Bas
  DECLARE SUB Demo ()
  DECLARE SUB InitVentLib ()
  DECLARE SUB LoopTest ()
  DECLARE SUB LoopTest5 ()
  DECLARE SUB LoopTest6 ()
  DECLARE SUB OhioFn ()
  DECLARE SUB TestD2a ()
  DECLARE SUB TestMode5 ()
  DECLARE SUB TestMode6 ()
  DECLARE SUB VentLoop ()
  DECLARE SUB VentPlotGrid ()
  DECLARE FUNCTION AvgA2dChan% (Count AS INTEGER, Chan AS
INTEGER, Period AS INTEGER, NumCh AS
INTEGER, NumPts AS INTEGER)
  DECLARE FUNCTION RateToV! (Opt AS INTEGER, Volt!)
  DECLARE FUNCTION VolToV! (Opt AS INTEGER, Volt!)

'$INCLUDE: 'DasLib.Bil'
'---------- DasLib.Bil ----------

'Das16 Common Area

'Das16 Parameters MUST be in common

CONST A2dBuffSize = 2000

DIM Dio(4) AS INTEGER
  DIM A2dBuff(2000) AS INTEGER
  DIM A2dChNum(2000) AS INTEGER
```

SUBSTITUTE SHEET

VentLib.Bas - Ohio 7000 Ventilator Control

```
COMMON Dio() AS INTEGER, Md AS INTEGER, Flag AS INTEGER
COMMON BiPolar AS INTEGER, DasChan AS INTEGER, VoltFS AS SINGLE
COMMON A2dBuff() AS INTEGER        'Buffer for DasMode4
COMMON A2dChNum() AS INTEGER       'Buffer for A/D channel
info 'for Mode 5 & 6, Quick Basic manages the Data Segment '$DYNAMIC
'Dynamic Common is dimensioned AFTER the COMMON specification CONST A2dBuf2Size = 2000
COMMON A2dBuf2() AS INTEGER        'Buffer for A/D data '$STATIC
'---------- End DasLib.Bil ----------

'$INCLUDE: 'MenuSys.Bil'
'---------- MenuSys.Bil----------

' Constants for best available screen mode
CONST VGA = 12
CONST MCGA = 13
CONST EGA256 = 9
CONST EGA64 = 8
CONST MONO = 10
CONST HERC = 3
CONST CGA = 1

' User-defined type to hold information about the mode
TYPE Config
    Scrn    AS INTEGER
    Colors  AS INTEGER
    Atribs  AS INTEGER
    XPix    AS INTEGER
```

123
VentLib.Bas - Ohio 7000 Ventilator Control

```
    YPix    AS INTEGER
    TCOL    AS INTEGER
    TROW    AS INTEGER
  END TYPE

'*****Graphics Modes
  COMMON VC AS Config, InitRows AS INTEGER, BestMode AS INTEGER,
Available AS STRING '****Menu system
  '$DYNAMIC
  COMMON PopBuf() AS INTEGER, CurPath$, ForGnd AS INTEGER, Bakgnd
AS INTEGER
  '$STATIC '---------- End MenuSys.Bil-----------

'$INCLUDE: 'VentLib.Bil'
'---------- VentLib.Bil ----------

'VentLib Dynamic Common declaration

TYPE VentDat              'Structure to hold modulation data
    Time AS SINGLE

Mode AS STRING * 1
    Modulation AS SINGLE
  END TYPE

CONST VentArrSize = 2000

COMMON VentArrNum AS INTEGER        '# of items loaded in
VentArr()
  COMMON VentDatFn$            'Data File loaded
```

124

VentLib.Bas - Ohio 7000 Ventilator Control

```
'$DYNAMIC
'Dynamic Common is dimensioned AFTER the COMMON specification

COMMON VentArr() AS VentDat          'Buffer for Ventilator
modulation data

'$STATIC

'---------- End VentLib.Bi1 ----------

'$INCLUDE: 'DasLib.Bi2'
'---------- DasLib.Bi2 ----------
  DIM A2dBuf2(A2dBuf2Size) AS INTEGER
'---------- End DasLib.Bi2 ----------

'$INCLUDE: 'MenuSys.Bi2'
'---------- MenuSys.Bi2----------
  DIM PopBuf(2002, 1) AS INTEGER   'PopUp Buffer
'---------- End MenuSys.Bi2----------

'$INCLUDE: 'VentLib.Bi2'
'---------- VentLib.Bi2 ----------
  DIM VentArr(VentArrSize) AS VentDat   'Buffer for Ventilator
modulation data '---------- End VentLib.Bi2 ----------

'$Page  $SubTitle:'FUNCTION AvgA2dChan%'
```

SUBSTITUTE SHEET

125

VentLib.Bas - Ohio 7000 Ventilator Control
FUNCTION AvgA2dChan%

FUNCTION AvgA2dChan% (Count AS INTEGER, Chan AS INTEGER, Period
AS INTEGER, NumCh AS INTEGER, N
umPts AS INTEGER)

'Function returns the average of an A/D channel over the previous Period
  'of observations, ending at position Count.
  'Data is input into A2dBuff() and A2dChNum() before call by DasMode9.
  'Count is provided by DasMode8, before call to DasMode9.
  '       is in range [0..(NumCh*NumPts)-1].
  'Chan is the channel # to average.
  'Period is the # of previous observations to average over.
  'NumCh channels of data is in data arrays.
  'NumPts is the number of points per channel.

'The index pointers may wrap around.

SHARED A2dBuff() AS INTEGER          'A/D data buffer
  SHARED A2dChNum() AS INTEGER         'channel # buffer DIM ptr AS INTEGER, i AS INTEGER
  DIM sum IF Count < 0 OR Count > (NumCh * NumPts) - 1 THEN
    PRINT "Count out of range in AvgA2dChan"
    DasMode7
    STOP
  END IF ptr = Count - 1            'use last conversion as end 'scan backwards until desired channel is located
  DO VentLib.Bas - Ohio 7000 Ventilator Control
FUNCTION AvgA2dChan%

```
    IF ptr < 0 THEN ptr = ptr + (NumCh * NumPts)      'protect
wrap arounds
    IF A2dChNum(ptr) = Chan THEN EXIT DO
    ptr = ptr - 1
  LOOP sum = 0

FOR i = 1 TO Period
    IF ptr < 0 THEN ptr = ptr + (NumCh * NumPts)      'protect
wrap arounds
'   IF A2dChNum(ptr) = Chan THEN
      sum = sum + A2dBuff(ptr)

'   END IF
    ptr = ptr - NumCh
  NEXT i

AvgA2dChan% = sum / Period

END FUNCTION

'$Page   $SubTitle:'SUB BrPrnData'
```

VentLib.Bas - Ohio 7000 Ventilator Control
SUB BrPrnData

SUB BrPrnData

'Browse Ventilator modulation data

SHARED CurPath$, ForGnd AS INTEGER, Bakgnd AS INTEGER

SHARED VentArrNum AS INTEGER      '# of items loaded in VentArr()
  SHARED VentDatFn$                 'Data File loaded
  SHARED VentArr() AS VentDat       'Buffer for Ventilator modulation data DIM i AS INTEGER, Ky$ IF VentArrNum = 0 THEN
    REDIM Msg$(3)
    Msg$(0) = "Browse Data"
    Msg$(1) = ""
    Msg$(2) = "NO data loaded"
    Msg$(3) = ""

MsgBox Msg$(), 3, Ky$, -1, -1    'unpop, pause
    ERASE Msg$
    EXIT SUB    'nothing to do
  END IF 'entertain the Human
  REDIM Msg$(3)
  Msg$(0) = "Browse Data"
  Msg$(1) = ""
  Msg$(2) = "Formating List..."
  Msg$(3) = ""

SUBSTITUTE SHEET

```
VentLib.Bas - Ohio 7000 Ventilator Control
SUB BrPrnData

MsgBox Msg$(), 3, Ky$, 0, 0       'no unpop, no pause
  ERASE Msg$

'Create list to browse
  REDIM txt$(VentArrNum)

'Generate header
  txt$(0) = "File: " + VentDatFn$
  i = 80 - LEN(txt$(0))
  txt$(0) = txt$(0) + LPad$("ESC - Exit", i)

FOR i = 1 TO VentArrNum
    txt$(i) = LPad$(STR$(i), 5)
    txt$(i) = txt$(i) + FUse$(VentArr(i).Time, 10, 2)
    txt$(i) = txt$(i) + LPad$(LEFT$(VentArr(i).Mode, 1), 5)
    txt$(i) = txt$(i) + FUse$(VentArr(i).Modulation, 10, 2)
  NEXT i UnPop                     'Clear Message box BrList txt$(), VentArrNum ERASE txt$

END SUB

'$Page  $SubTitle:'SUB demo'
```

129

VentLib.Bas - Ohio 7000 Ventilator Control
SUB demo

SUB Demo

SHARED Dio() AS INTEGER, Md AS INTEGER, Flag AS INTEGER
    SHARED BiPolar AS INTEGER, DasChan AS INTEGER, VoltFS AS SINGLE
    SHARED A2dBuff() AS INTEGER        'Buffer for DasMode4
    SHARED A2dBuf2() AS INTEGER DIM NextCh AS INTEGER, ChLow AS INTEGER, ChHigh AS INTEGER DasMode0
    PRINT BiPolar, DasChan DasMode1 0, 3
    DasMode2 NextCh, ChLow, ChHigh
    PRINT NextCh, ChLow, ChHigh DasMode7
    'Test Mode 3
    INPUT "mode 3 test"; a$
    FOR ch = 0 TO 3
       DasMode3 A2dData%, A2dCh%
       PRINT A2dToVolt(A2dData%), A2dCh%
    NEXT ch 'Test Mode 4
    INPUT "mode 4 test"; a$
    DasMode17 (100)
    DasMode4 (100)
    FOR i = 0 TO 99 STEP 4
       PRINT A2dBuff(i); A2dBuff(i + 1); A2dBuff(i + 2); A2dBuff(i + 3)
    NEXT i INPUT "mode 5 test"; a$

130

```
VentLib.Bas - Ohio 7000 Ventilator Control
SUB demo

TestMode5

INPUT "mode 6 test"; a$
  TestMode6

TestD2a

END SUB

'$Page   $SubTitle:'SUB InitDas16'
```

131

```
VentLib.Bas - Ohio 7000 Ventilator Control
SUB InitDas16

SUB InitDas16
  'General Reset
  DasMode0           'Init Driver
  DasMode7           'Clear DMA or Interrupt operation
  DasMode16 0, 0     'D/A's to zero
END SUB '$Page  $SubTitle:'SUB InitVentLib'
```

SUBSTITUTE SHEET

132

```
VentLib.Bas - Ohio 7000 Ventilator Control
SUB InitVentLib

SUB InitVentLib

SHARED VentArrNum AS INTEGER        '# of items loaded in
VentArr()
   SHARED VentDatFn$                   'Data File loaded
   SHARED VentArr() AS VentDat         'Buffer for Ventilator
modulation data VentArrNum = 0
   VentDatFn$ = ""

END SUB

'$Page   $SubTitle:'SUB LoadVentDatPrn'
```

VentLib.Bas - Ohio 7000 Ventilator Control
SUB LoadVentDatPrn

SUB LoadVentDatPrn

```
'Load a .PRN format file created by a spreadsheet to emulate
real data
    '       Time  Rate/Volume   Modulation
    '          0       R                 6
    '          0       V                 2
    '    4.23569       R          36.81015
    '   13.60336       R          13.74554
    '   20.26031       V          28.91379
    '   25.65653       V          14.68135

SHARED CurPath$, ForGnd AS INTEGER, Bakgnd AS INTEGER

SHARED VentArrNum AS  INTEGER          '# of items loaded in
VentArr()
    SHARED VentDatFn$                      'Data File loaded
    SHARED VentArr() AS VentDat            'Buffer for Ventilator
modulation data DIM Ky$, p$
    DIM fp AS INTEGER, i AS INTEGER REDIM Msg$(5)
    Msg$(0) = "Import VENTILATOR data"
    Msg$(1) = ""
    Msg$(2) = "Select an ASCII data file to load"
    Msg$(3) = "as a Ventilator control data file."
    Msg$(4) = ""
    Msg$(5) = "Press any key to continue"

MsgBox Msg$(), 5, Ky$, -1, -1      'unpop, pause
    ERASE Msg$
```

SUBSTITUTE SHEET

134

VentLib.Bas - Ohio 7000 Ventilator Control
SUB LoadVentDatPrn

```
  IF Ky$ = CHR$(27) THEN EXIT SUB    'ESC pressed

'Try to open a file
  SelectFile VentDatFn$

IF VentDatFn$ = "" THEN            'nothing selected
    InitVentLib                      'clear common buffer
    EXIT SUB
  END IF 'Display status box while loading
  REDIM Msg$(3)

Msg$(0) = "Import VENTILATOR data"
  Msg$(1) = ""
  Msg$(2) = "Loading: " + CurPath$ + VentDatFn$
  Msg$(3) = ""
  MsgBox Msg$(), 3, Ky$, 0, 0        'no unpop, no pause
  ERASE Msg$ fp = FREEFILE
  OPEN CurPath$ + VentDatFn$ FOR INPUT AS #fp VentArrNum = 0           'init # loaded i = 1

DO WHILE NOT EOF(1)
    LINE INPUT #1, p$
    p$ = UCASE$(LTRIM$(RTRIM$(p$)))

IF LEN(p$) > 0 THEN
      'Parse input line
      VentArr(0).Time = VAL(StrTok$(p$, " "))
```

SUBSTITUTE SHEET

135

```
VentLib.Bas - Ohio 7000 Ventilator Control
SUB LoadVentDatPrn

VentArr(0).Mode = LEFT$(StrTok$("", " "), 1)
      VentArr(0).Modulation = VAL(StrTok$("", " "))

'test if valid - see format above
      IF  VentArr(0).Time >= 0 AND  (VentArr(0).Mode  =  "R"  OR
VentArr(0).Mode = "V") AND VentArr(
0).Modulation > 0 THEN
         VentArr(i).Time = VentArr(0).Time
         VentArr(i).Mode = VentArr(0).Mode
         VentArr(i).Modulation = VentArr(0).Modulation
         VentArrNum = i
         i = i + 1
      END IF 'test if buffer exceeded
      IF i > VentArrSize THEN EXIT DO
    END IF

LOOP

CLOSE #fp

UnPop                     'Clear "Loading" Message - no unpop

IF VentArrNum = 0 THEN
    VentDatFn$ = ""
    EXIT SUB
  END IF

REDIM Msg$(5)
  Msg$(0) = "Import VENTILATOR data"
  Msg$(1) = ""
  Msg$(2) = "File: " + CurPath$ + VentDatFn$
```

SUBSTITUTE SHEET

136

```
VentLib.Bas - Ohio 7000 Ventilator Control
SUB LoadVentDatPrn

Msg$(3) = STR$(VentArrNum) + " obs. loaded"
   Msg$(4) = ""
   Msg$(5) = "Press any key to continue"

MsgBox Msg$(), 5, Ky$, -1, -1      'unpop, pause
   ERASE Msg$

END SUB

'$Page   $SubTitle:'SUB LoopTest'
```

SUBSTITUTE SHEET

137

```
VentLib.Bas - Ohio 7000 Ventilator Control
SUB LoopTest

SUB LoopTest

'Closed Loop Test of Ohio Ventilator
  'R decreases modulated rate, T increases
  'V decreases modulated volume, B increases
  'Uses Mode4 Das16 operation SHARED A2dBuff() AS INTEGER         'Buffer for DasMode4

DIM cmd$, Avg(3), i AS INTEGER, VolCtrl, RateCtrl, VolMod,
RateMod
  DIM VolOut, RateOut, VolD2a, RateD2a CLS
  PRINT "ESC to terminate Closed Loop Test"
  PRINT "R/T = -/+ Rate     V/B = -/+ Volume"

LOCATE 5, 15: PRINT "---Volume--"
  LOCATE 6, 15: PRINT "L/Min  Volt";

LOCATE 5, 30: PRINT "----Rate---"
  LOCATE 6, 30: PRINT "Bth/M  Volt";

LOCATE 7, 1: PRINT "Baseline";
  LOCATE 8, 1: PRINT "Modulation";
  LOCATE 9, 1: PRINT "D/A Drive";
  LOCATE 10, 1: PRINT "Output";

DasMode1 0, 3            'Setup Das16 for channels 0-3
  DasMode17 (100)          '100 Hz/Ch sampling rate 'Initialize keyboard volume and rate modulation values
  VolMod = 2
  RateMod = 6
```

SUBSTITUTE SHEET

138

```
VentLib.Bas - Ohio 7000 Ventilator Control
SUB LoopTest

DO

'Use Mode4 to get 100 mS of Data - speed medium
    DasMode4 (4 * 10)          '10 pts per channel @ 10 mS/Pt =
100 mS 'Cal avg of the volume and rate control settings
    Avg(0) = 0         'Volume
    Avg(2) = 0         'Rate FOR i = 0 TO (10 * 4) - 1 STEP 4
      Avg(0) = Avg(0) + A2dBuff(i)
      Avg(2) = Avg(2) + A2dBuff(i + 2)
    NEXT i Avg(0) = A2dToVolt(CINT(Avg(0) / 10!))
    VolCtrl = VolToV(1, Avg(0))
    Avg(2) = A2dToVolt(CINT(Avg(2) / 10!))
    RateCtrl = RateToV(1, Avg(2))

'Report Control settings to screen

LOCATE 7, 15
    PRINT USING "##.## #.###"; VolCtrl; Avg(0);
    LOCATE 7, 30
    PRINT USING "##.## #.###"; RateCtrl; Avg(2);

cmd$ = INKEY$

SELECT CASE UCASE$(cmd$)
      CASE "R"
        IF RateMod > 6 THEN RateMod = RateMod - 1
      CASE "T"
        IF RateMod < 40 THEN RateMod = RateMod + 1
```

SUBSTITUTE SHEET

139

VentLib.Bas - Ohio 7000 Ventilator Control
SUB LoopTest

```
    CASE "V"
      IF VolMod > 2 THEN VolMod = VolMod - 1
    CASE "B"
      IF VolMod < 30 THEN VolMod = VolMod + 1

CASE CHR$(27)
      EXIT DO
    CASE ""
    CASE ELSE
      BEEP
  END SELECT

'Display the Volume and Rate Modulations
  LOCATE 8, 15
  PRINT USING "##.## #.###"; VolMod; VolToV(2, VolMod);
  LOCATE 8, 30
  PRINT USING "##.## #.###"; RateMod; RateToV(2, RateMod);

'if the Modulation level is greater than the set point,
  'increase the drive to the ventilator VolD2a = 0
  IF VolMod > VolCtrl THEN
    VolD2a = VolToV(2, VolMod) - VolToV(2, VolCtrl)
  END IF RateD2a = 0
  IF RateMod > RateCtrl THEN
    RateD2a = RateToV(2, RateMod) - RateToV(2, RateCtrl)
  END IF 'Output modulation to D/A
  DasMode16 VoltToD2a%(VolD2a), VoltToD2a%(RateD2a)
```

SUBSTITUTE SHEET

VentLib.Bas - Ohio 7000 Ventilator Control
SUB LoopTest

```
    'Display the Volume and Rate D/A Modulations levels
    LOCATE 9, 15
    PRINT USING "      #.###"; VolD2a;
    LOCATE 9, 30
    PRINT USING "      #.###"; RateD2a;

'Use Mode4 to get 100 mS of Data - speed medium
    DasMode4 (4 * 10)         '10 pts per channel @ 10 mS/Pt =
100 mS 'Cal avg of the volume output and rate output levels
    Avg(1) = 0              'Volume Output
    Avg(3) = 0              'Rate Output
    FOR i = 0 TO (10 * 4) - 1 STEP 4
      Avg(1) = Avg(1) + A2dBuff(i + 1)
      Avg(3) = Avg(3) + A2dBuff(i + 3)
    NEXT i Avg(1) = A2dToVolt(CINT(Avg(1) / 10!))
    VolOut = VolToV(1, Avg(1))
    Avg(3) = A2dToVolt(CINT(Avg(3) / 10!))
    RateOut = RateToV(1, Avg(3))
    'Report Outputs to screen
    LOCATE 10, 15
    PRINT USING "##.## #.###"; VolOut; Avg(1);
    LOCATE 10, 30
    PRINT USING "##.## #.###"; RateOut; Avg(3);
  LOOP UNTIL cmd$ = CHR$(27)

'Zero D/A's
  DasMode16 0, 0
END SUB

'$Page  $SubTitle:'SUB LoopTest5'
```

141

```
VentLib.Bas - Ohio 7000 Ventilator Control
SUB LoopTest5

SUB LoopTest5

'Uses Mode5 Das16 operation

'Closed Loop Test of Ohio Ventilator
  'R decreases modulated rate, T increases
  'V decreases modulated volume, B increases SHARED A2dBuff() AS INTEGER         'Buffer for DasMode4

DIM cmd$, Avg(3), i AS INTEGER, VolCtrl, RateCtrl, VolMod,
RateMod
  DIM VolOut, RateOut, VolD2a, RateD2a
  DIM Op AS INTEGER, Status AS INTEGER, Count AS INTEGER CLS
  PRINT "ESC to terminate Closed Loop Test"
  PRINT "R/T = -/+ Rate     V/B = -/+ Volume"

LOCATE 5, 15: PRINT "---Volume--"
  LOCATE 6, 15: PRINT "L/Min  Volt";

LOCATE 5, 30: PRINT "----Rate---"
  LOCATE 6, 30: PRINT "Bth/M  Volt";

LOCATE 7, 1: PRINT "Baseline";
  LOCATE 8, 1: PRINT "Modulation";
  LOCATE 9, 1: PRINT "D/A Drive";
  LOCATE 10, 1: PRINT "Output";

DasMode1 0, 3           'Setup Das16 for channels 0-3
  DasMode7 (100)          '100 Hz/Ch sampling rate 'Initialize keyboard volume and rate modulation values
```

SUBSTITUTE SHEET

VentLib.Bas - Ohio 7000 Ventilator Control
SUB LoopTest5

VolMod = 2
  RateMod = 6

DO

'Use Mode5 to get 100 mS of Data - speed medium - Background
    DasMode5 4 * 10, 0      'get 10 pts per channel, only one cycle 'watch Count until done
    DO DasMode8 Op, Status, Count
    LOOP UNTIL Status = 0

DasMode9 10 * 4, 0          'Xfer to A2dBuff()

'Cal avg of the volume and rate control settings
    Avg(0) = 0          'Volume
    Avg(2) = 0          'Rate
    FOR i = 0 TO (10 * 4) - 1 STEP 4
      Avg(0) = Avg(0) + A2dBuff(i)
      Avg(2) = Avg(2) + A2dBuff(i + 2)
    NEXT i Avg(0) = A2dToVolt(CINT(Avg(0) / 10!))
    VolCtrl = VolToV(1, Avg(0))
    Avg(2) = A2dToVolt(CINT(Avg(2) / 10!))
    RateCtrl = RateToV(1, Avg(2))

'Report Control settings to screen
    LOCATE 7, 15
    PRINT USING "##.## #.###"; VolCtrl; Avg(0);
    LOCATE 7, 30

SUBSTITUTE SHEET

VentLib.Bas - Ohio 7000 Ventilator Control
SUB LoopTest5

```
    PRINT USING "##.## #.###"; RateCtrl; Avg(2);

cmd$ = INKEY$

SELECT CASE UCASE$(cmd$)
      CASE "R"
        IF RateMod > 6 THEN RateMod = RateMod - 1
      CASE "T"
        IF RateMod < 40 THEN RateMod = RateMod + 1

CASE "V"
        IF VolMod > 2 THEN VolMod = VolMod - 1
      CASE "B"
        IF VolMod < 30 THEN VolMod = VolMod + 1
      CASE CHR$(27)
        EXIT DO
      CASE ""
      CASE ELSE
        BEEP
    END SELECT

'Display the Volume and Rate Modulations
    LOCATE 8, 15
    PRINT USING "##.## #.###"; VolMod; VolToV(2, VolMod);
    LOCATE 8, 30
    PRINT USING "##.## #.###"; RateMod; RateToV(2, RateMod);

'if the Modulation level is greater than the set point,
    'increase the drive to the ventilator VolD2a = 0
    IF VolMod > VolCtrl THEN
       VolD2a = VolToV(2, VolMod) - VolToV(2, VolCtrl)
    END IF
```

```
VentLib.Bas - Ohio 7000 Ventilator Control
SUB LoopTest5

RateD2a = 0
   IF RateMod > RateCtrl THEN
      RateD2a = RateToV(2, RateMod) - RateToV(2, RateCtrl)
   END IF 'Output modulation to D/A
   DasMode16 VoltToD2a%(VolD2a), VoltToD2a%(RateD2a)

'Display the Volume and Rate D/A Modulations levels
   LOCATE 9, 15
   PRINT USING "    #.###"; VolD2a;
   LOCATE 9, 30
   PRINT USING "    #.###"; RateD2a;

'Use Mode5 to get 100 mS of Data - speed medium - Background
   DasMode5 4 * 10, 0       'get 10 pts per channel, only one cycle 'watch Count until done
   DO
      DasMode8 Op, Status, Count
   LOOP UNTIL Status = 0

DasMode9 10 * 4, 0            'Xfer to A2dBuff()

'Cal avg of the volume output and rate output levels
   Avg(1) = 0           'Volume Output
   Avg(3) = 0           'Rate Output
   FOR i = 0 TO (10 * 4) - 1 STEP 4
      Avg(1) = Avg(1) + A2dBuff(i + 1)
      Avg(3) = Avg(3) + A2dBuff(i + 3)
   NEXT i
```

SUBSTITUTE SHEET

VentLib.Bas - Ohio 7000 Ventilator Control
SUB LoopTest5

```
    Avg(1) = A2dToVolt(CINT(Avg(1) / 10!))
    VolOut = VolToV(1, Avg(1))
    Avg(3) = A2dToVolt(CINT(Avg(3) / 10!))
    RateOut = RateToV(1, Avg(3))

'Report Outputs to screen
    LOCATE 10, 15
    PRINT USING "##.## #.###"; VolOut; Avg(1);
    LOCATE 10, 30
    PRINT USING "##.## #.###"; RateOut; Avg(3);

LOOP UNTIL cmd$ = CHR$(27)

DasMode16 0, 0         'Zero D/A's
  DasMode7               'Disable Interrupt

END SUB

'$Page  $SubTitle:'SUB LoopTest6'
```

SUBSTITUTE SHEET

146

VentLib.Bas - Ohio 7000 Ventilator Control
SUB LoopTest6

SUB LoopTest6

'Uses Mode6 Das16 operation

'Closed Loop Test of Ohio Ventilator
  'R decreases modulated rate, T increases
  'V decreases modulated volume, B increases SHARED A2dBuff() AS INTEGER         'Buffer for DasMode4

DIM cmd$, Avg(3), i AS INTEGER, VolCtrl, RateCtrl, VolMod, RateMod
  DIM VolOut, RateOut, VolD2a, RateD2a
  DIM Op AS INTEGER, Status AS INTEGER, Count AS INTEGER CLS
  PRINT "ESC to terminate Closed Loop Test"
  PRINT "R/T = -/+ Rate     V/B = -/+ Volume"

LOCATE 5, 15: PRINT "---Volume--"
  LOCATE 6, 15: PRINT "L/Min  Volt";

LOCATE 5, 30: PRINT "----Rate---"
  LOCATE 6, 30: PRINT "Bth/M  Volt";

LOCATE 7, 1: PRINT "Baseline";
  LOCATE 8, 1: PRINT "Modulation";
  LOCATE 9, 1: PRINT "D/A Drive";
  LOCATE 10, 1: PRINT "Output";

DasMode1 0, 3           'Setup Das16 for channels 0-3
  DasMode17 (100)         '100 Hz/Ch sampling rate 'Initialize keyboard volume and rate modulation values VentLib.Bas - Ohio 7000 Ventilator Control
SUB LoopTest6

```
  VolMod = 2
  RateMod = 6

DO

'Use Mode6 to get 100 mS of Data - speed high - Background
    DasMode6 4 * 10, 0        'get 10 pts per channel, only one
cycle 'watch Count until done DO
       DasMode8 Op, Status, Count
    LOOP UNTIL Status = 0

DasMode9 10 * 4, 0            'Xfer to A2dBuff()

'Cal avg of the volume and rate control settings
    Avg(0) = 0             'Volume
    Avg(2) = 0             'Rate
    FOR i = 0 TO (10 * 4) - 1 STEP 4
      Avg(0) = Avg(0) + A2dBuff(i)
      Avg(2) = Avg(2) + A2dBuff(i + 2)
    NEXT i Avg(0) = A2dToVolt(CINT(Avg(0) / 10!))
    VolCtrl = VolToV(1, Avg(0))
    Avg(2) = A2dToVolt(CINT(Avg(2) / 10!))
    RateCtrl = RateToV(1, Avg(2))
    'Report Control settings to screen
    LOCATE 7, 15
    PRINT USING "##.## #.###"; VolCtrl; Avg(0);
    LOCATE 7, 30
    PRINT USING "##.## #.###"; RateCtrl; Avg(2);
```

SUBSTITUTE SHEET

VentLib.Bas - Ohio 7000 Ventilator Control
SUB LoopTest6

```
    cmd$ = INKEY$

SELECT CASE UCASE$(cmd$)
      CASE "R"
        IF RateMod > 6 THEN RateMod = RateMod - 1
      CASE "T"
        IF RateMod < 40 THEN RateMod = RateMod + 1
      CASE "V"
        IF VolMod > 2 THEN VolMod = VolMod - 1
      CASE "B"
        IF VolMod < 30 THEN VolMod = VolMod + 1
      CASE CHR$(27)
        EXIT DO
      CASE ""

CASE ELSE
        BEEP
    END SELECT

'Display the Volume and Rate Modulations
    LOCATE 8, 15
    PRINT USING "##.## #.###"; VolMod; VolToV(2, VolMod);
    LOCATE 8, 30
    PRINT USING "##.## #.###"; RateMod; RateToV(2, RateMod);

'if the Modulation level is greater than the set point,
    'increase the drive to the ventilator VolD2a = 0
    IF VolMod > VolCtrl THEN
      VolD2a = VolToV(2, VolMod) - VolToV(2, VolCtrl)
    END IF
```

VentLib.Bas - Ohio 7000 Ventilator Control
SUB LoopTest6

```
    RateD2a = 0
    IF RateMod > RateCtrl THEN
       RateD2a = RateToV(2, RateMod) - RateToV(2, RateCtrl)
    END IF 'Output modulation to D/A
    DasMode16 VoltToD2a%(VolD2a), VoltToD2a%(RateD2a)

'Display the Volume and Rate D/A Modulations levels
    LOCATE 9, 15
    PRINT USING "     #.###"; VolD2a;
    LOCATE 9, 30
    PRINT USING "     #.###"; RateD2a;

'Use Mode6 to get 100 mS of Data - speed high - Background
    DasMode6 4 * 10, 0       'get 10 pts per channel, only one
cycle 'watch Count until done
    DO
       DasMode8 Op, Status, Count
    LOOP UNTIL Status = 0

DasMode9 10 * 4, 0         'Xfer to A2dBuff()

'Cal avg of the volume output and rate output levels
    Avg(1) = 0          'Volume Output
    Avg(3) = 0          'Rate Output
    FOR i = 0 TO (10 * 4) - 1 STEP 4
       Avg(1) = Avg(1) + A2dBuff(i + 1)
       Avg(3) = Avg(3) + A2dBuff(i + 3)
    NEXT i
```

SUBSTITUTE SHEET

150

```
VentLib.Bas - Ohio 7000 Ventilator Control
SUB LoopTest6

Avg(1) = A2dToVolt(CINT(Avg(1) / 10!))
    VolOut = VolToV(1, Avg(1))
    Avg(3) = A2dToVolt(CINT(Avg(3) / 10!))
    RateOut = RateToV(1, Avg(3))

'Report Outputs to screen
    LOCATE 10, 15
    PRINT USING "##.## #.###"; VolOut; Avg(1);
    LOCATE 10, 30
    PRINT USING "##.## #.###"; RateOut; Avg(3);

LOOP UNTIL cmd$ = CHR$(27)

DasMode16 0, 0          'Zero D/A's
    DasMode7                'Disable Interrupt

END SUB

'$Page   $SubTitle:'SUB OhioFn'
```

SUBSTITUTE SHEET

VentLib.Bas - Ohio 7000 Ventilator Control
SUB OhioFn

```
SUB OhioFn
  'VentFn4.Bas
  'Sept 29/93

DIM i AS INTEGER, Volt, Vol, Rate

DasMode0
  DasMode1 0, 3
  DasMode7

CLS
  LOCATE 4, 1
  PRINT "Volt";
  LOCATE 5, 1
  PRINT "Calc";
  LOCATE 3, 10
  PRINT "-----Litre/Min------";
  LOCATE 3, 40
  PRINT "-----Breath/Min-----";

DO
     FOR ch = 0 TO 3
        DasMode3 A2dData%, A2dCh%
'       PRINT A2dCh%;

IF ch < 2 THEN
           LOCATE 6, 10 + (ch * 15)
           PRINT USING "#####"; A2dData%;
           LOCATE 4, 10 + (ch * 15)
           PRINT USING "#.###"; A2dToVolt(A2dData%);
           IF   ch  =  1   THEN   DasMode15    0,
VoltToD2a%(A2dToVolt(A2dData%))
```

VentLib.Bas - Ohio 7000 Ventilator Control
SUB OhioFn

```
      LOCATE 5, 10 + (ch * 15)
      PRINT USING "##.##"; VolToV(1, A2dToVolt(A2dData%));

ELSE
      LOCATE 4, 10 + (ch * 15)
      PRINT USING "#.###"; A2dToVolt(A2dData%);
      LOCATE 5, 10 + (ch * 15)
      PRINT USING "##.##"; RateToV(1, A2dToVolt(A2dData%));
    END IF NEXT ch
  PRINT
  a$ = INKEY$
LOOP UNTIL a$ <> ""
EXIT SUB FOR i = 2 TO 30
  Volt = VolToV(2, CSNG(i))
  Vol = VolToV(1, Volt)

PRINT USING "## #.### ####.#"; i; Volt; Vol
  IF i MOD 10 = 0 THEN INPUT a$
NEXT i FOR i = 6 TO 40
  Volt = RateToV(2, CSNG(i))
  Rate = RateToV(1, Volt)
  PRINT USING "## #.### ####.#"; i; Volt; Rate
  IF i MOD 10 = 0 THEN INPUT a$
NEXT i

END SUB

'$Page   $SubTitle:'SUB PlotVentDat'
```

VentLib.Bas - Ohio 7000 Ventilator Control
SUB PlotVentDat

SUB PlotVentDat

```
    SHARED VentArrNum AS INTEGER          '# of items loaded in
VentArr()
    SHARED VentDatFn$                     'Data File loaded
    SHARED VentArr() AS VentDat           'Buffer for Ventilator
modulation data DIM i AS INTEGER, init AS INTEGER
    DIM oldY AS SINGLE IF VentArrNum = 0 THEN
       REDIM Msg$(3)
       Msg$(0) = "Plot Data"
       Msg$(1) = ""
       Msg$(2) = "NO data loaded"
       Msg$(3) = ""

MsgBox Msg$(), 3, Ky$, -1, -1      'unpop, pause
       ERASE Msg$
       EXIT SUB    'nothing to do
    END IF VentPlotGrid              'draw axis and define plot window 'Plot Volume
    WINDOW (0, 0)-(VentArr(VentArrNum).Time, 30)

init = -1

FOR i = 1 TO VentArrNum
       IF VentArr(i).Mode = "V" THEN      'Volume data
          IF init THEN
             init = 0
```

SUBSTITUTE SHEET

VentLib.Bas - Ohio 7000 Ventilator Control
SUB PlotVentDat

```
        PSET (VentArr(i).Time, VentArr(i).Modulation), 1
        oldY = VentArr(i).Modulation
      ELSE
        LINE -(VentArr(i).Time, oldY), 1
        LINE -(VentArr(i).Time, VentArr(i).Modulation), 1
        oldY = VentArr(i).Modulation
      END IF
    END IF
  NEXT i 'Plot Rate
  WINDOW (0, 0)-(VentArr(VentArrNum).Time, 40)
  init = -1
  FOR i = 1 TO VentArrNum
    IF VentArr(i).Mode = "R" THEN          'Rate data
      IF init THEN
        init = 0
        PSET (VentArr(i).Time, VentArr(i).Modulation), 2
        oldY = VentArr(i).Modulation
      ELSE
        LINE -(VentArr(i).Time, oldY), 2
        LINE -(VentArr(i).Time, VentArr(i).Modulation), 2
        oldY = VentArr(i).Modulation
      END IF
    END IF
  NEXT i
  DO
    a$ = INKEY$
  LOOP UNTIL a$ <> ""
  SCREEN 0, 0, 0
  WIDTH 80
END SUB '$Page  $SubTitle:'FUNCTION RateToV'
```

155

VentLib.Bas - Ohio 7000 Ventilator Control
FUNCTION RateToV

FUNCTION RateToV (Opt AS INTEGER, Volt)

'Sept 29/93
  '------------------------------------------------
  'Function Library for Ohio 7000 Ventilator Control
  '------------------------------------------------

'Based on observations of Breath/Min Rate control
  '   Y  =   a    +    bX
  '   mV = 18.06555 + 50.48908 * Rate        R^2=0.999555

'   V = 1.80655462E-02 + 5.04890756E-02 * Rate
R^2=0.999555

'   Rate      Regression Output:
  '   Constant                              1.80655462E-02
  '   Std Err of Y Est                      1.10777101E-02
  '   R Squared                             9.99555207E-01
  '   No. of Observations                               35
  '   Degrees of Freedom                                33
  '
  '   X Coefficient(s)       5.04890756E-02
  '   Std Err of Coef.       1.85402629E-04

DIM V, Rate, a, b

'   V = 1.80655462E-02 + 5.04890756E-02 * Rate
R^2=0.999555
  a = .0180655462#
  b = .0504890756#

SELECT CASE Opt%
    CASE 1            'V to Rate
      V = Volt

SUBSTITUTE SHEET

156

VentLib.Bas - Ohio 7000 Ventilator Control
FUNCTION RateToV

```
    Rate = (V - a) / b       ' x = (Y - a) / b
    RateToV = Rate
  CASE 2           'Rate to V
    Rate = Volt
    V = a + b * Rate         ' y = a + bx
    RateToV = V
END SELECT

END FUNCTION

'$Page  $SubTitle:'SUB TestD2a'
```

VentLib.Bas - Ohio 7000 Ventilator Control
SUB TestD2a

```
SUB TestD2a

DIM i AS INTEGER, a$

INPUT "Channel 0 ramp"; a$
  FOR i = 0 TO 4095 STEP 2
    DasMode15 0, i
  NEXT i
  DasMode15 0, 0

INPUT "Channel 1 ramp"; a$
  FOR i = 0 TO 4095 STEP 2
    DasMode15 1, i
  NEXT i
  DasMode15 1, 0

INPUT "Dual Channel ramp"; a$
  FOR i = 0 TO 4095 STEP 2
    DasMode16 i, i
  NEXT i
  DasMode16 0, 0

END SUB

'$Page  $SubTitle:'SUB TestMode5'
```

SUBSTITUTE SHEET

158

VentLib.Bas - Ohio 7000 Ventilator Control
SUB TestMode5

```
SUB TestMode5

SHARED A2dBuff() AS INTEGER        'A/D data buffer
  SHARED A2dChNum() AS INTEGER       'channel # buffer DIM Op AS INTEGER, Status AS INTEGER, Count AS INTEGER, i AS
INTEGER DasMode0              'init
  DasMode1 0, 3         'scan 0 to 3
  DasMode17 (100)       'sample @ 100 Hz
  DasMode5 500, 0       'get 500 pts, only one cycle DO
    DasMode8 Op, Status, Count
    PRINT Op, Status, Count
  LOOP UNTIL Status = 0
  PRINT Op, Status, Count DasMode9 500, 0          'Xfer to A2dBuff(), A2dChNum()

FOR i = 0 TO 499 STEP 4
    PRINT A2dChNum(i); A2dBuff(i), A2dChNum(i + 1); A2dBuff(i +
1), A2dChNum(i + 2); A2dBuff(i
+ 2), A2dChNum(i + 3); A2dBuff(i + 3)
  NEXT i DasMode7              'clear Background operation
END SUB '$Page  $SubTitle:'SUB TestMode6'
```

SUBSTITUTE SHEET

VentLib.Bas - Ohio 7000 Ventilator Control
SUB TestMode6

```
SUB TestMode6

SHARED A2dBuff() AS INTEGER          'A/D data buffer
   SHARED A2dChNum() AS INTEGER         'channel # buffer DIM Op AS INTEGER, Status AS INTEGER, Count AS INTEGER, i AS
INTEGER DasMode0              'init
   DasMode1 0, 3         'scan 0 to 3
   DasMode17 (100)       'sample @ 100 Hz
   DasMode6 500, 0       'get 100 pts, only one cycle DO
     DasMode8 Op, Status, Count
     PRINT Op, Status, Count
   LOOP UNTIL Status = 0

DasMode9 500, 0           'Xfer to A2dBuff()

FOR i = 0 TO 499 STEP 4
     PRINT A2dChNum(i); A2dBuff(i), A2dChNum(i + 1); A2dBuff(i +
1), A2dChNum(i + 2); A2dBuff(i
+ 2), A2dChNum(i + 3); A2dBuff(i + 3)
   NEXT i DasMode7              'clear Background operation
END SUB '$Page   $SubTitle:'SUB VentLoop'
```

160

VentLib.Bas - Ohio 7000 Ventilator Control
SUB VentLoop

SUB VentLoop

'Uses function to return avg of A/D channels when running
   'in continuous acquisition mode 6.

'Modulates ventilator with data in common - if loaded.

SHARED VentArrNum AS INTEGER         '# of items loaded in
VentArr()
   SHARED VentDatFn$                    'Data File loaded
   SHARED VentArr() AS VentDat          'Buffer for Ventilator
modulation data DIM Op AS INTEGER, Status AS INTEGER, Count AS INTEGER
   DIM OldCount AS INTEGER, Done AS INTEGER, Chan AS INTEGER
   DIM i AS INTEGER
   DIM a$, mask$, mask1$ DIM tStart AS SINGLE              'starting time
   DIM tNow AS SINGLE                'current time DIM NumCh AS INTEGER              '# channels to acquire
   DIM PtsPerCh AS INTEGER           '# points per channel
   DIM AvPer AS INTEGER              'Avg Period of A/D data DIM VolMod, RateMod               'Vol & Rate Modulation level
   DIM VolModV, RateModV                'Volts of Vol & Rate
Modulation level DIM VolCtrl, RateCtrl             'Setting of ventilator Vol
& Rate Ctrls
   DIM VolCtrlV, RateCtrlV           'Volts of ventilator Vol &
Rate Ctrls

SUBSTITUTE SHEET

```
VentLib.Bas - Ohio 7000 Ventilator Control
SUB VentLoop

DIM VolD2a, RateD2a         'D/A outputs for Volume and
Rate

DIM Vol, Rate               'Current drive to Ventilator
  DIM VolV, RateV              'Current drive Voltage to
Ventilator NumCh = 4                   'channels 0 to 3
  PtsPerCh = 20               'acquire 20 pts per channel
  AvPer = 10                  'average previous 100 mS
  DasMode0                    'Init Driver
  DasMode7                       'Clear DMA or Interrupt
operation
  DasMode16 0, 0              'D/A's to zero 'Build Status Screen
  COLOR 14, 1
  CLS
  a$ = "Ventilation Control - Press ESC to Terminate"
  LOCATE 1, 40 - LEN(a$) / 2
  PRINT a$ IF VentArrNum > 0 THEN      'Display Modulation file -
if loaded
    a$ = "File: " + VentDatFn$
    LOCATE 25, 40 - LEN(a$) / 2
    PRINT a$;

END IF

LOCATE 7, 30
  PRINT "--Volume---"
  LOCATE 8, 30
  PRINT "L/Min  Volt"
```

SUBSTITUTE SHEET

162

VentLib.Bas - Ohio 7000 Ventilator Control
SUB VentLoop

```
    LOCATE 7, 45
    PRINT "---Rate----"
    LOCATE 8, 45
    PRINT "Bth/M  Volt"
    LOCATE 10, 15
    PRINT "BaseLine"
    LOCATE 11, 15
    PRINT "Modulation"
    LOCATE 12, 15
    PRINT "D/A Drive"
    LOCATE 13, 15
    PRINT "Output"
    mask$ = "##.## #.###"
    mask1$ = "     #.###"

DasMode1 0, NumCh - 1              'Setup Das16 for channels 0-3
    DasMode17 (100)                    '100 Hz/Ch sampling rate 'Use Mode6 to get 200 mS of Data - speed high - Background
    DasMode6 NumCh * PtsPerCh, 1       'get 10 pts per ch, cycle
continuously 'Wait until filled A/D buffer once - 200 mS DasMode8 Op, Status, OldCount      'look at A/D buffer index
pointer
    Done = 0
    DO
       DasMode8 Op, Status, Count      'look at A/D buffer index
pointer IF Count < OldCount THEN        'wrapped around!
          Done = -1
```

SUBSTITUTE SHEET

VentLib.Bas - Ohio 7000 Ventilator Control
SUB VentLoop

```
   ELSE
      OldCount = Count            'wait until wrap around
   END IF

LOOP UNTIL Done

VolMod = 2                        'Zero Modulation Levels
RateMod = 6

'What to do i = 0

DO

IF i = 0 THEN                  'Init
      i = 1
      tStart = TIMER              'remember starting time
   END IF 'If data loaded, see if it is time to change modulation level
   IF VentArrNum > 0 THEN
     tNow = TIMER - tStart IF tNow < 0 THEN tNow = tNow + 86400   'working late eh!

IF tNow >= VentArr(i).Time THEN        'change modulation
     ' LOCATE 17, 30
     ' PRINT USING "#####.# ! ##.##"; tNow; VentArr(i).Mode; VentArr(i).Modulation SELECT CASE VentArr(i).Mode
```

SUBSTITUTE SHEET

VentLib.Bas - Ohio 7000 Ventilator Control
SUB VentLoop

```
            CASE "R"
              RateMod = VentArr(i).Modulation
              i = i + 1
            CASE "V"
              VolMod = VentArr(i).Modulation
              i = i + 1
         END SELECT
       END IF 'When we reach the end of the data send [VentArr()] - wrap
arround
       IF i > VentArrNum THEN i = 0

END IF t1 = TIMER
    IF 1 = 1 THEN                              'Volume

'Read Volume control - avg of previous 100 mS
       DasMode8 Op, Status, Count         'determine current index
pointer
       DasMode9 NumCh * PtsPerCh, 0       'Xfer to A2dBuff(),
A2dChNum()

'Read Volume control position
       Chan = 0
       VolCtrlV = A2dToVolt(AvgA2dChan%(Count, Chan, AvPer, NumCh,
PtsPerCh))
       VolCtrl = VolToV(1, VolCtrlV)

'Read Volume Ventilator is running at
       Chan = 1
       VolV = A2dToVolt(AvgA2dChan%(Count, Chan, AvPer, NumCh,
PtsPerCh))
```

SUBSTITUTE SHEET

165

```
VentLib.Bas - Ohio 7000 Ventilator Control
SUB VentLoop

Vol = VolToV(1, VolV)

'Calculate Volume Modulation into volts
    VolModV = VolToV(2, VolMod)

'Calculate D/A drive to Achieve Modulation Level
    IF VolModV > VolCtrlV THEN      'Modulation > set point
       VolD2a = VolModV - VolCtrlV
    ELSE                            'Modulation <= set point
       VolD2a = 0
    END IF 'Send the Volume Drive to the Ventilator via D/A channel
0
    DasMode15 0, VoltToD2a%(VolD2a)

LOCATE 10, 30
    PRINT USING mask$; VolCtrl; VolCtrlV
    LOCATE 11, 30
    PRINT USING mask$; VolMod; VolModV
    LOCATE 12, 30
    PRINT USING mask1$; VolD2a
    LOCATE 13, 30
    PRINT USING mask$; Vol; VolV
  END IF IF 2 = 2 THEN                     'Rate 'Read Rate control - avg of previous 100 mS
    DasMode8 Op, Status, Count      'determine current index
pointer
    DasMode9 NumCh * PtsPerCh, 0    'Xfer to A2dBuff(),
A2dChNum()
```

SUBSTITUTE SHEET

166

VentLib.Bas - Ohio 7000 Ventilator Control
SUB VentLoop

```
    'Read Rate control position
    Chan = 2
    RateCtrlV = A2dToVolt(AvgA2dChan%(Count, Chan, AvPer,
NumCh, PtsPerCh))
    RateCtrl = RateToV(1, RateCtrlV)

'Read Rate Ventilator is running at
    Chan = 3
    RateV = A2dToVolt(AvgA2dChan%(Count, Chan, AvPer, NumCh,
PtsPerCh))
    Rate = RateToV(1, RateV)

'Calculate Rate Modulation into volts
    RateModV = RateToV(2, RateMod)

'Calculate D/A drive to Achieve Modulation Level
    IF RateModV > RateCtrlV THEN    'Modulation > set point
      RateD2a = RateModV - RateCtrlV
    ELSE                            'Modulation <= set point
      RateD2a = 0
    END IF 'Send the Rate Drive to the Ventilator via D/A channel 1
    DasMode15 1, VoltToD2a%(RateD2a)

LOCATE 10, 45
    PRINT USING mask$; RateCtrl; RateCtrlV

LOCATE 11, 45
    PRINT USING mask$; RateMod; RateModV
    LOCATE 12, 45
    PRINT USING mask1$; RateD2a
```

SUBSTITUTE SHEET

167

```
VentLib.Bas - Ohio 7000 Ventilator Control
SUB VentLoop

LOCATE 13, 45
        PRINT USING mask$; Rate; RateV
    END IF
    t2 = TIMER

LOCATE 15, 30: PRINT USING "loop time = ##.##"; t2 - t1 a$ = INKEY$
  LOOP UNTIL a$ = CHR$(27)

DasMode16 0, 0        'Zero D/A's
  DasMode7              'Disable Interrupt

END SUB

'$Page  $SubTitle:'SUB VentPlotGrid'
```

SUBSTITUTE SHEET

VentLib.Bas - Ohio 7000 Ventilator Control
SUB VentPlotGrid

```
SUB VentPlotGrid

SHARED Vc AS Config, InitRows AS INTEGER, BestMode AS INTEGER,
Available AS STRING SHARED VentArrNum AS INTEGER         '# of items loaded in
VentArr()
  SHARED VentDatFn$                    'Data File loaded
  SHARED VentArr() AS VentDat          'Buffer for Ventilator
modulation data DIM txtX AS INTEGER, txtY AS INTEGER
  DIM x1 AS INTEGER, x2 AS INTEGER, y1 AS INTEGER, y2 AS INTEGER
  DIM i AS INTEGER
  DIM r AS SINGLE SCREEN BestMode
  SetConfig BestMode         'Fill in VC Parameters COLOR 1, 1                 'White BackGround, Palette 1
  CLS 'Calculate Char size in this mode
  txtX = (Vc.XPix + 1) \ Vc.TCol
  txtY = (Vc.YPix + 1) \ Vc.TRow 'Label Header
  LOCATE 1, 7
  PRINT "File: "; VentDatFn$;

'Label Left Vertical Axis - Volume
  LOCATE 2, 2: PRINT "Vol";
  LOCATE 3, 3: PRINT "30";
  LOCATE Vc.TRow - 2, 3: PRINT " 0";
```

SUBSTITUTE SHEET

VentLib.Bas - Ohio 7000 Ventilator Control
SUB VentPlotGrid

```
  'Tick Left Axis [0..30] every 5
  x1 = 4 * txtX
  x2 = 5 * txtX
  y1 = 2 * txtY + (txtY) \ 2
  y2 = (Vc.TRow - 2) * txtY - (txtY) \ 2
  VIEW (x1, y1)-(x2, y2)
  WINDOW (0, 1)-(1, 7)
  FOR i = 1 TO 7
     LINE (0, i)-(1, i), 1
  NEXT i 'Label Right Vertical Axis - Rate
  LOCATE 2, Vc.TCol - 4: PRINT "Rate";
  LOCATE 3, Vc.TCol - 4: PRINT "40";
  LOCATE Vc.TRow - 2, Vc.TCol - 4: PRINT " 0";

'Tick Right Axis [0..40] every 5
  x1 = (Vc.TCol - 5) * txtX
  x2 = (Vc.TCol - 6) * txtX
  y1 = 2 * txtY + (txtY) \ 2
  y2 = (Vc.TRow - 2) * txtY - (txtY) \ 2
  VIEW (x1, y1)-(x2, y2)
  WINDOW (0, 1)-(1, 9)
  FOR i = 1 TO 9
     LINE (0, i)-(1, i), 2
  NEXT i 'Label X Axis
  LOCATE Vc.TRow, (Vc.TCol \ 2) - 2
  PRINT "(Sec)";
  LOCATE Vc.TRow, 6
  PRINT "0.0";
  LOCATE Vc.TRow, Vc.TCol - 4 - 6
  PRINT FUse$(VentArr(VentArrNum).Time, 6, 1);
```

170

VentLib.Bas - Ohio 7000 Ventilator Control
SUB VentPlotGrid

```
    'Tick Horizontal Axis by 100 Secs
    x1 = 5 * txtX
    x2 = (Vc.TCol - 6) * txtX
    y1 = (Vc.TRow - 2) * txtY - (txtY) \ 2
    y2 = y1 + (txtY \ 2)
    VIEW (x1, y1)-(x2, y2)
    WINDOW (0, 0)-(VentArr(VentArrNum).Time, 1)
    FOR r = 0 TO VentArr(VentArrNum).Time STEP 100
        LINE (r, 0)-(r, 1), 3
    NEXT r 'Exit with the Plot Window defined
    x1 = 5 * txtX' - 1
    x2 = (Vc.TCol - 6) * txtX' + 1
    y1 = 2 * txtY + (txtY) \ 2' - 1
    y2 = (Vc.TRow - 2) * txtY - (txtY) \ 2' + 1
    VIEW (x1, y1)-(x2, y2), 3, 3

END SUB

'$Page  $SubTitle:'FUNCTION VolToV'
```

SUBSTITUTE SHEET

171

```
VentLib.Bas - Ohio 7000 Ventilator Control
FUNCTION VolToV

FUNCTION VolToV (Opt AS INTEGER, Volt)

'Sept 29/93
  '------------------------------------------------
  'Function Library for Ohio 7000 Ventilator Control
  '------------------------------------------------

'Based on observations of Litre/Min Volume control
  '   Y =     a    +     bX
  '   mV = 66.19015 + 66.71872 * Vol     R^2=0.998923

'    V = 6.61901478E-02 + 6.67187192E-02 * Vol
R^2=9.98922670E-01

'   Vol       Regression Output:
  '   Constant                              6.61901478E-02
  '   Std Err of Y Est                      1.89986311E-02
  '   R Squared                             9.98922670E-01
  '   No. of Observations                              29
  '   Degrees of Freedom                               27
  '
  '   X Coefficient(s)     6.67187192E-02
  '   Std Err of Coef.     4.21671541E-04

DIM V, Vol, a, b

'    V = 6.61901478E-02 + 6.67187192E-02 * Vol
R^2=9.98922670E-01
  a = .0661901478#
  b = .0667187192#

SELECT CASE Opt%
    CASE 1           'Volt to Vol
```

SUBSTITUTE SHEET

172

```
VentLib.Bas - Ohio 7000 Ventilator Control
FUNCTION VolToV

V = Volt
    Vol = (V - a) / b       ' x = (Y - a) / b
    VolToV = Vol
  CASE 2              'Vol to V
    Vol = Volt
    V = a + b * Vol         ' y = a + bx
    VolToV = V
 END SELECT

END FUNCTION

43949 Bytes Available
28608 Bytes Free

0 Warning Error(s)
    0 Severe  Error(s)
```

TABLE III

| Variable | Control Ventilator | Computer Ventilator | p-value |
|---|---|---|---|
| Weight (kg) | 21.7 ± 2.8 | 23.4 ± 1.3 | ns |
| Oleic Acid Infused (ml/kg) | 0.20 ± 0.05 | 0.24 ± 0.11 | ns |
| Mean Airway Pressure (cm $H_2O$) | 12.02 ± 0.54 | 11.41 ± 0.39 | ns |
| Mean Peak Airway Pressure (cm $H_2O$) | 59.5 ± 1.3 | 56.6 ± 3.0 | ns |
| Wet:Dry Weight Ratio | 10.1 ± 1.1 | 9.2 ± 1.2 | ns |

Mean ± S.D.
Control Group n = 6
Computer Group n = 7
except for mean airway pressure and mean peak airway pressure
Control Group n = 4
Computer Group n = 3

TABLE IV

| | | Time (minutes) Following Oleic Acid Infusion | | | | | | |
|---|---|---|---|---|---|---|---|---|
| Variable | Baseline | 0 | 30 | 60 | 90 | 120 | 150 | 180 |
| Temp (° C.) | | | | | | | | |
| Computer | 37.8 ± 1.0 | 38.3 ± 1.0* | 38.4 ± 1.1* | 38.5 ± 1.0* | 38.4 ± 0.9* | 38.5 ± 1.0* | 38.6 ± 1.1* | 38.6 ± 1.3* |
| Control | 37.2 ± 1.2+ | 38.0 ± 1.2* | 38.3 ± 1.1* | 38.4 ± 1.2* | 38.5 ± 1.0* | 38.5 ± 1.4* | 38.9 ± 1.2* | 39.0 ± 1.3* |
| Temp (° C.) | | | | | | | | |
| Computer | 36.8 ± 0.6 | 37.0 ± 0.9 | 37.3 ± 0.6 | 37.1 ± 0.8 | 37.3 ± 0.5 | 37.2 ± 0.5 | 37.2 ± 0.7 | 37.2 ± 1.1 |
| Control | 36.4 ± 1.2 | 37.1 ± 1.1* | 37.5 ± 0.9* | 37.3 ± 0.7* | 37.4 ± 0.8* | 37.7 ± 0.7* | 37.7 ± 1.0* | 37.9 ± 1.0* |
| Hgb (g %) | | | | | | | | |
| Computer | 9.2 ± 1.0 | 11.6 ± 1* | 11.8 ± .8* | 11.9 ± .7* | 11.6 ± .7* | 11.7 ± .5* | 11.8 ± .8* | 12.3 ± .7* |
| Control | 10.0 ± .9+ | 12.6 ± 1*+ | 13.0 ± 1*+ | 13.3 ± 1.3*+ | 13.7 ± 1*+ | 13.9 ± 1*+ | 14.1 ± 1* | 14.5 ± .8*+ |
| pH | | | | | | | | |
| Computer | 7.49 ± .03 | 7.37 ± .04* | 7.38 ± .05* | 7.36 ± .07* | 7.38 ± .06*+ | 7.37 ± .04*+ | 7.37 ± .04*+ | 7.34 ± .05*+ |
| Control | 7.48 ± .04 | 7.38 ± .03* | 7.35 ± .02* | 7.33 ± .02* | 7.33 ± .03* | 7.33 ± .03* | 7.31 ± .06* | 7.29 ± .07* |

Mean ± S.D.
+ P < 0.05 between Groups
Bonferroni's correction applied for multiple comparisons
Computer Group n = 7
Control Group n = 6
Temp = blood temperature
Temp = nasopharyngeal temperature

TABLE V

| | | Time (minutes) Following Oleic Acid Infusion | | | | | | |
|---|---|---|---|---|---|---|---|---|
| Variable | Baseline | 0 | 30 | 60 | 90 | 120 | 150 | 180 |
| MAP (mm Hg) | | | | | | | | |
| Computer | 91 ± 15 | 78 ± 11*+ | 75 ± 14* | 75 ± 12* | 73 ± 10* | 75 ± 12* | 76 ± 9* | 77 ± 8* |
| Control | 92 ± 14 | 68 ± 16* | 69 ± 20* | 71 ± 14* | 71 ± 15* | 78 ± 19* | 79 ± 20* | 78 ± 17* |
| MPAP (mm Hg) | | | | | | | | |
| Computer | 22 ± 5 | 40 ± 4* | 39 ± 3* | 39 ± 5* | 37 ± 5* | 39 ± 6* | 40 ± 7* | 42 ± 4* |
| Control | 19 ± 2+ | 37 ± 4* | 37 ± 6* | 40 ± 5* | 40 ± 3*+ | 40 ± 5* | 43 ± 2* | 43 ± 3* |
| PCWP (mm Hg) | | | | | | | | |
| Computer | 10 ± 1 | 11 ± 1 | 11 ± .6 | 10 ± 1 | 10 ± .5 | 11 ± 1 | 12 ± 3 | 11 ± 3 |
| Control | 11 ± 1 | 12 ± 1 | 11 ± 2 | 11 ± 1 | 11 ± .8 | 10 ± 1 | 10 ± 2+ | 10 ± 1 |
| PVR (mm Hg.l$^{-1}$ min) | | | | | | | | |
| Computer | 3 ± 1 | 12 ± 1* | 12 ± 2* | 12 ± 2* | 10 ± 2* | 12 ± 4* | 12 ± 5* | 11 ± 4* |
| Control | 2 ± .7 | 13 ± 4* | 13 ± 6* | 15 ± 6* | 14 ± 5*+ | 15 ± 5*+ | 15 ± 7*+ | 15 ± 5*+ |

TABLE V-continued

| | | Time (minutes) Following Oleic Acid Infusion | | | | | | |
|---|---|---|---|---|---|---|---|---|
| Variable | Baseline | 0 | 30 | 60 | 90 | 120 | 150 | 180 |
| CO (1.min$^{-1}$) | | | | | | | | |
| Computer | 4.2 ± .3 | 2.5 ± .4* | 2.6 ± .4* | 2.5 ± .4* | 2.6 ± .3* | 2.5 ± .3* | 2.5 ± .4* | 2.7 ± .4* |
| Control | 4.0 ± .9 | 2.4 ± .6* | 2.5 ± .9* | 2.5 ± .9* | 2.3 ± .6* | 2.5 ± .8* | 2.5 ± 1.0* | 2.5 ± .8* |

Mean ± S.D.
*P < 0.05 within Groups
+ P < 0.05 between Groups
Bonferroni's correction applied for multiple comparisons
Computer Group n = 7
Control Group n = 6
MPAP = Mean Pulmonary Artery Pressure
PCWP = Pulmonary Capillary Wedge Pressure
PVR = Pulmonary Vascular Resistance
CO = Cardiac Output

TABLE VI

| | | Time (minutes) Following Oleic Acid Infusion | | | | | | |
|---|---|---|---|---|---|---|---|---|
| Variable | Baseline | 0 | 30 | 60 | 90 | 120 | 150 | 180 |
| PeCO$_2$ (mm Hg) | | | | | | | | |
| Computer | 17.5 ± 4.8 | 13.7 ± 2.6 | 14.4 ± 2.5 | 16.1 ± 3.2 | 14.7 ± 2.9 | 15.0 ± 2.2 | 13.1 ± 2.3 | 15.2 ± 2.7 |
| Control | 19.8 ± 3.7 | 16.1 ± 4.1 | 14.5 ± 2.5 | 15.4 ± 3.6 | 15.7 ± 3.8 | 16.8 ± 4.9 | 17.8 ± 6.8 | 17.3 ± 6.1 |
| PaCO$_2$ (mm Hg) | | | | | | | | |
| Computer | 36.3 ± 2 | 46.6 ± 3* | 45.3 ± 6* | 47.7 ± 8* | 45.8 ± 8* | 46.0 ± 4* | 46.8 ± 6* | 49.9 ± 6* |
| Control | 36.9 ± 2 | 43.6 ± 1* | 46.1 ± 4* | 48.2 ± 7* | 48.1 ± 3* | 49.0 ± 5* | 49.0 ± 7* | 51.2 ± 13* |
| PaO$_2$ (mm Hg) | | | | | | | | |
| Computer | 558 ± 31 | 133 ± 39* | 140 ± 68* | 158 ± 93* | 203 ± 88* | 197 ± 124* | 162 ± 119* | 116 ± 64* |
| Control | 556 ± 57 | 112 ± 56* | 103 ± 56* | 92 ± 51*+ | 90 ± 53*+ | 75 ± 20*+ | 65 ± 10*+ | 65 ± 15* |
| QS/QT | | | | | | | | |
| Computer | 10.0 ± 4.6 | 18.4 ± 3.9* | 17.4 ± 4.0* | 16.8 ± 4.1* | 15.9 ± 3.5* | 15.9 ± 4.2* | 16.7 ± 3.4* | 17.8 ± 3.9* |
| Control | 9.0 ± 3.0 | 18.6 ± 4.6* | 19.0 ± 5.7* | 17.7 ± 3.3* | 17.9 ± 4.1* | 18.3 ± 4.0* | 17.6 ± 4.6* | 18.3 ± 5.1* |
| VD/VT | | | | | | | | |
| Computer | 52.1 ± 10.2 | 70.5 ± 5.8* | 68.0 ± 5.2 | 66.0 ± 5.0* | 67.5 ± 6.1* | 67.3 ± 5.2* | 71.6 ± 5.3* | 69.6 ± 4.1* |
| Control | 45.6 ± 12.1 | 63.3 ± 8.5* | 68.3 ± 6.0* | 67.9 ± 7.4* | 67.5 ± 7.2* | 65.6 ± 8.1* | 64.4 ± 10* | 66.9 ± 4.6* |

Mean ± S.D.
*P < 0.05 within Groups
+ P < 0.05 between Groups
Bonferroni's correction applied for multiple comparisons
Computer Group n = 7
Control Group n = 6
PeCO$_2$ = end expired CO$_2$
QS/QT = shunt fraction
VD/VT = dead space ventilation

TABLE VII

| Variable | Hypothermia | Rewarming |
|---|---|---|
| Temp °C. | | |
| Computer | 28.4 ± .3 | 35.6 ± .82* |
| Control | 28.0 ± .24 | 35.0 ± .91* |
| MAP (mm Hg) | | |
| Computer | 91 ± 26 | 93 ± 17 |
| Control | 81 ± 13 | 82 ± 10+ |
| CSFP (mm Hg) | | |
| Computer | 9.1 ± 3 | 14.6 ± 3.7* |
| Control | 8.2 ± 4.3 | 12.3 ± 4.1*+ |
| CPP (mm Hg) | | |
| Computer | 82 ± 26 | 80 ± 19 |
| Control | 72 ± 15 | 69 ± 11 |

Computer n = 6
Control n = 6
*p < 0.05 within groups
+p < 0.05 between groups

TABLE VIII

| Variable | Hypothermia | Rewarming |
|---|---|---|
| Hgb (g/dl) | | |
| Computer | 7.4 ± .7 | 8.1 ± .9 |
| Control | 7.7 ± 1.1 | 7.7 ± 1 |
| $PaCO_2$ (mm Hg) | | |
| Computer | 37 ± 2 | 36 ± 1 |
| Control | 38 ± 2 | 36 ± 6 |
| pH | | |
| Computer | 7.35 ± .01 | 7.35 ± .02 |
| Control | 7.33 ± .02 | 7.35 ± .08 |
| Cont Diff (Vol %) | | |
| Computer | 4.4 ± 1.2 | 4.3 ± 1.1 |
| Control | 3.6 ± 0.7 | 4.9 ± 1.1* |
| SSS $PO_2$ (mm Hg) | | |
| Computer | 44 ± 6 | 42 ± 7* |
| Control | 44 ± 3 | 38 ± 4*+ |
| SSS Sat (%) | | |
| Computer | 68 ± 11 | 67 ± 10 |
| Control | 69 ± 6 | 60 ± 7*+ |

Computer n = 6
Control n = 6
*p < 0.05 within groups
+p < 0.05 between groups

TABLE IX

| Variable | Hypothermia | Rewarming |
|---|---|---|
| tCBF (ml.g$^{-1}$.min$^{-1}$) | | |
| Computer | .18 ± .08 | .36 ± .07* |
| Control | .17 ± .06 | .33 ± .06* |
| hCBF (ml.g$^{-1}$.min$^{-1}$) | | |
| Computer | .17 ± .1 | .35 ± .08* |
| Control | .17 ± .06 | .32 ± .06* |
| bsCBF (ml.g$^{-1}$.min$^{-1}$) | | |
| Computer | .21 ± .11 | .41 ± .07* |
| Control | .20 ± .07 | .38 ± .08* |
| FLOW:METABOLISM | | |
| Computer | 23.1 ± 5.2 | 23.9 ± 5.0 |
| Control | 28.6 ± 5.6 | 22.3 ± 4.3* |
| $CMRO_2$ | | |
| Computer | .008 ± .004 | .016 ± .008* |
| Control | .006 ± .002 | .014 ± .002* |

Computer n = 6
Control n = 6
*p < 0.005 within groups
+p < 0.005 between groups

We claim:

1. A method of controlling flow of a biological fluid to an organ during controlled life support conditions, which comprises:

establishing a predetermined pattern of variations over time of instantaneous changes in flow of a biological fluid to an independently-functioning normal organ of a mammalian species, generating a variable control parameter for regulation of flow of said biological fluid to an organ during controlled life support conditions in accordance with said predetermined pattern, and controlling said flow of said biological fluid to said organ during controlled life support conditions in accordance with said variable control parameter.

2. A method of controlling flow of blood by a pump to a body during cardiopulmonary bypass, which comprises:

establishing a predetermined pattern of variation over time of instantaneous blood pressure and heart rate of an independently-functioning healthy heart of mammalian species, generating a signal corresponding in value to an individually-determined blood pressure for a period of time corresponding to the heart rate for the difference between said individually-determined blood pressure and the next individually-determined blood pressure of said predetermined pattern, generating a control voltage corresponding in magnitude to said signal, applying said control voltage to said pump to provide an output of blood from said pump to the body during said cardiopulmonary bypass of a pressure proportional to the magnitude of said signal for said period of time, and repeating said steps of generating a signal, generating a control voltage and applying said control voltage to said pump for each next individually-determined blood pressure of said predetermined pattern, whereby a pulsatile flow of blood from the pump during said cardiopulmonary bypass is provided to the body which mimics normal pulsatile blood flow from a healthy heart.

3. Apparatus for controlling the flow of a biological fluid to an organ, which comprises:

means for establishing a predetermined pattern of variations over time of instantaneous changes in flow of a biological fluid to an independently-functioning normal organ of a mammalian species, means for generating a variable control parameter for regulation of flow of the biological fluid to an organ during controlled life support conditions in accordance with the predetermined pattern, and means for controlling the flow of the biological fluid to the organ during controlled life support conditions in accordance with the variable control parameter.

4. The apparatus of claim 3 for use in controlling the flow of blood by a pump to a body during cardiopulmonary by-pass wherein said means for establishing a predetermined pattern comprises means for establishing a predetermined pattern of variation over time of instantaneous blood pressure and heart rate of an independently-functioning heart of a mammalian species; said means for generating a variable control parameter comprises means for generating a signal corresponding in value to an individually-determined blood pressure for a period of time corresponding to the heart rate for a difference between such individually-determined blood pressure and the next individually-determined blood pressure of said predetermined pattern and means for generating a control voltage corresponding in magnitude to said signal; and said means for controlling the flow of the biological fluid comprises means for applying said control voltage to said pump to provide an output of blood from said pump to the body during cardiopulmonary bypass of a pressure proportional to the magnitude of the signal for said period of time and means for repeating the steps of generating a signal, generating a control voltage and applying the control voltage to the pump for each next individually-determined blood pressure of said predetermined pattern.

* * * * *